US010655136B2

(12) United States Patent
Huang et al.

(10) Patent No.: US 10,655,136 B2
(45) Date of Patent: May 19, 2020

(54) METHODS AND COMPOSITIONS FOR INTRODUCING NUCLEIC ACIDS INTO PLANTS

(71) Applicant: MONSANTO TECHNOLOGY LLC, St. Louis, MO (US)

(72) Inventors: Shihshieh Huang, Woodland, CA (US); Alberto B. Iandolino, Davis, CA (US); Gregory J. Peel, Davis, CA (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 15/579,120

(22) PCT Filed: Jun. 2, 2016

(86) PCT No.: PCT/US2016/035500

§ 371 (c)(1),
(2) Date: Dec. 1, 2017

(87) PCT Pub. No.: WO2016/196782

PCT Pub. Date: Dec. 8, 2016

(65) Prior Publication Data

US 2018/0163219 A1 Jun. 14, 2018

Related U.S. Application Data

(60) Provisional application No. 62/170,447, filed on Jun. 3, 2015.

(51) Int. Cl.
*C12N 15/82* (2006.01)
*A01H 1/06* (2006.01)

(52) U.S. Cl.
CPC .......... *C12N 15/8218* (2013.01); *A01H 1/06* (2013.01); *C12N 15/8207* (2013.01); *C12N 15/8213* (2013.01); *C12N 15/8279* (2013.01)

(58) Field of Classification Search
CPC .......... C12N 15/8218
USPC .......... 800/279
See application file for complete search history.

(56) References Cited

U.S. PATENT DOCUMENTS 3,687,808 A 8/1972 Merigan et al.
3,791,932 A 2/1974 Schuurs et al.
3,839,153 A 10/1974 Schuurs et al.
3,850,578 A 11/1974 McConnell
3,850,752 A 11/1974 Schuurs et al.
3,853,987 A 12/1974 Dreyer
3,867,517 A 2/1975 Ling
3,879,262 A 4/1975 Schuurs et al.
3,901,654 A 8/1975 Gross
3,935,074 A 1/1976 Rubenstein et al.
3,984,533 A 10/1976 Uzgiris
3,996,345 A 12/1976 Ullman et al.
4,034,074 A 7/1977 Miles
4,098,876 A 7/1978 Piasio et al.
4,469,863 A 9/1984 Ts'o et al.
4,476,301 A 10/1984 Imbach et al.
4,535,060 A 8/1985 Comai
4,581,847 A 4/1986 Hibberd et al.
4,666,828 A 5/1987 Gusella
4,683,202 A 7/1987 Mullis
4,761,373 A 8/1988 Anderson et al.
4,769,061 A 9/1988 Comai
4,801,531 A 1/1989 Frossard
4,810,648 A 3/1989 Stalker
4,879,219 A 11/1989 Wands et al.
4,940,835 A 7/1990 Shah et al.
4,971,908 A 11/1990 Kishore et al.
5,004,863 A 4/1991 Umbeck
5,011,771 A 4/1991 Bellet et al.
5,013,659 A 5/1991 Bedbrook et al.
5,015,580 A 5/1991 Christou et al.
5,023,243 A 6/1991 Tullis
5,034,506 A 7/1991 Summerton et al.
5,094,945 A 3/1992 Comai
5,141,870 A 8/1992 Bedbrook et al.
5,145,783 A 9/1992 Kishore et al.
5,159,135 A 10/1992 Umbeck
5,166,315 A 11/1992 Summerton et al.
5,177,196 A 1/1993 Meyer, Jr. et al.
5,185,444 A 2/1993 Summerton et al.

(Continued)

FOREIGN PATENT DOCUMENTS

AU 2008258254 B2 7/2014
AU 2014262189 B2 11/2014

(Continued)

OTHER PUBLICATIONS

Cong et al., "Multiplex Genome Engineering Using CRISPR/Cas Systems," *Science*, 339:819-823 (2013).
Gao et al., "DNA-guided genome editing using the *Natronobacterium gregoryi* Argonaute," *Nature Biotechnology*, 34(7):768-773 (2016).
Horsch et al., "Inheritance of Functional Foreign Genes in Plants," *Science*, 223:496-498(1984).
Hsu et al., "DNA targeting specificity of RNA-guided Cas9 nucleases," *Nature Biotechnology*, 31:827-832 (2013).
International Search Report dated Oct. 13, 2016, in International Patent Application No. PCT/US2016/35500.

(Continued)

*Primary Examiner* — Li Zheng
(74) *Attorney, Agent, or Firm* — Amanda Carmany-Rampey; David R. Marsh; Arnold & Porter Kaye Scholer LLP

(57) ABSTRACT

The present disclosure provides compositions and methods for introducing nucleic acids into plants. More specifically, disclosed herein are methods and compositions for introducing a nucleic acid, such as a double-stranded RNA, for silencing a target gene in a plant. Also disclosed herein are plants exhibiting modification of a target gene, obtained through the use of such methods and compositions.

10 Claims, 2 Drawing Sheets

Specification includes a Sequence Listing.

(56) References Cited

U.S. PATENT DOCUMENTS 5,188,642 A 2/1993 Shah et al.
5,188,897 A 2/1993 Suhadolnik et al.
5,192,659 A 3/1993 Simons
5,214,134 A 5/1993 Weis et al.
5,216,141 A 6/1993 Benner
5,235,033 A 8/1993 Summerton et al.
5,264,423 A 11/1993 Cohen et al.
5,264,562 A 11/1993 Matteucci
5,264,564 A 11/1993 Matteucci
5,272,057 A 12/1993 Smulson et al.
5,276,019 A 1/1994 Cohen et al.
5,281,521 A 1/1994 Trojanowski et al.
5,286,634 A 2/1994 Stadler et al.
5,286,717 A 2/1994 Cohen et al.
5,304,732 A 4/1994 Anderson et al.
5,310,667 A 5/1994 Eichholtz et al.
5,312,910 A 5/1994 Kishore et al.
5,321,131 A 6/1994 Agrawal et al.
5,331,107 A 7/1994 Anderson et al.
5,339,107 A 8/1994 Henry et al.
5,346,107 A 9/1994 Bouix et al.
5,378,824 A 1/1995 Bedbrook et al.
5,384,253 A 1/1995 Krzyzek et al.
5,390,667 A 2/1995 Kumakura et al.
5,392,910 A 2/1995 Bell et al.
5,393,175 A 2/1995 Courville
5,399,676 A 3/1995 Froehler
5,405,938 A 4/1995 Summerton et al.
5,405,939 A 4/1995 Suhadolnik et al.
5,416,011 A 5/1995 Hinchee et al.
5,453,496 A 9/1995 Caruthers et al.
5,455,233 A 10/1995 Spielvogel et al.
5,459,127 A 10/1995 Felgner et al.
5,460,667 A 10/1995 Moriyuki et al.
5,462,910 A 10/1995 Ito et al.
5,463,174 A 10/1995 Moloney et al.
5,463,175 A 10/1995 Barry et al.
5,466,677 A 11/1995 Baxter et al.
5,470,967 A 11/1995 Huie et al.
5,476,925 A 12/1995 Letsinger et al.
5,489,520 A 2/1996 Adams et al.
5,489,677 A 2/1996 Sanghvi et al.
5,491,288 A 2/1996 Chaubet et al.
5,510,471 A 4/1996 Lebrun et al.
5,518,908 A 5/1996 Corbin et al.
5,519,126 A 5/1996 Hecht
5,536,821 A 7/1996 Agrawal et al.
5,538,880 A 7/1996 Lundquist et al.
5,541,306 A 7/1996 Agrawal et al.
5,541,307 A 7/1996 Cook et al.
5,550,111 A 8/1996 Suhadolnik et al.
5,550,318 A 8/1996 Adams et al.
5,550,398 A 8/1996 Kocian et al.
5,550,468 A 8/1996 Haäberlein et al.
5,558,071 A 9/1996 Ward et al.
5,561,225 A 10/1996 Maddry et al.
5,561,236 A 10/1996 Leemans et al.
5,563,253 A 10/1996 Agrawal et al.
5,569,834 A 10/1996 Hinchee et al.
5,571,799 A 11/1996 Tkachuk et al.
5,587,361 A 12/1996 Cook et al.
5,591,616 A 1/1997 Hiei et al.
5,593,874 A 1/1997 Brown et al.
5,596,086 A 1/1997 Matteucci et al.
5,597,717 A 1/1997 Guerineau et al.
5,602,240 A 2/1997 De Mesmaeker et al.
5,605,011 A 2/1997 Bedbrook et al.
5,608,046 A 3/1997 Cook et al.
5,610,289 A 3/1997 Cook et al.
5,618,704 A 4/1997 Sanghvi et al.
5,623,070 A 4/1997 Cook et al.
5,625,050 A 4/1997 Beaton et al.
5,627,061 A 5/1997 Barry et al.
5,633,360 A 5/1997 Bischofberger et al.
5,633,435 A 5/1997 Barry et al.
5,633,448 A 5/1997 Lebrun et al.
5,639,024 A 6/1997 Mueller et al.
5,646,024 A 7/1997 Leemans et al.
5,648,477 A 7/1997 Leemans et al.
5,663,312 A 9/1997 Chaturvedula
5,677,437 A 10/1997 Teng et al.
5,677,439 A 10/1997 Weis et al.
5,719,046 A 2/1998 Guerineau et al.
5,721,138 A 2/1998 Lawn
5,731,180 A 3/1998 Dietrich
5,739,180 A 4/1998 Taylor-Smith
5,746,180 A 5/1998 Jefferson et al.
5,767,361 A 6/1998 Dietrich
5,767,373 A 6/1998 Ward et al.
5,780,708 A 7/1998 Lundquist et al.
5,804,425 A 9/1998 Barry et al.
5,824,877 A 10/1998 Hinchee et al.
5,837,848 A 11/1998 Ely et al.
5,859,347 A 1/1999 Brown et al.
5,866,775 A 2/1999 Eichholtz et al.
5,874,265 A 2/1999 Adams et al.
5,879,903 A 3/1999 Strauch et al.
5,914,451 A 6/1999 Martinell et al.
5,919,675 A 7/1999 Adams et al.
5,928,937 A 7/1999 Kakefuda et al.
5,939,602 A 8/1999 Volrath et al.
5,969,213 A 10/1999 Adams et al.
5,981,840 A 11/1999 Zhao et al.
5,985,793 A 11/1999 Sandbrink et al.
RE36,449 E 12/1999 Lebrun et al.
6,040,497 A 3/2000 Spencer et al.
6,056,938 A 5/2000 Unger et al.
6,069,115 A 5/2000 Pallett et al.
6,084,089 A 7/2000 Mine et al.
6,084,155 A 7/2000 Volrath et al.
6,118,047 A 9/2000 Anderson et al.
6,121,513 A 9/2000 Zhang et al.
6,130,366 A 10/2000 Herrera-Estrella et al.
6,140,078 A 10/2000 Sanders et al.
6,153,812 A 11/2000 Fry et al.
6,160,208 A 12/2000 Lundquist et al.
6,177,616 B1 1/2001 Bartsch et al.
6,194,636 B1 2/2001 McElroy et al.
6,225,105 B1 5/2001 Sathasivan et al.
6,225,114 B1 5/2001 Eichholtz et al.
6,232,526 B1 5/2001 McElroy et al.
6,245,968 B1 6/2001 Boudec et al.
6,248,876 B1 6/2001 Barry et al.
6,252,138 B1 6/2001 Karimi et al.
RE37,287 E 7/2001 Lebrun et al.
6,268,549 B1 7/2001 Sailland et al.
6,271,359 B1 8/2001 Norris et al.
6,282,837 B1 9/2001 Ward et al.
6,288,306 B1 9/2001 Ward et al.
6,288,312 B1 9/2001 Christou et al.
6,294,714 B1 9/2001 Matsunaga et al.
6,326,193 B1 12/2001 Liu et al.
6,329,571 B1 12/2001 Hiei
6,348,185 B1 2/2002 Piwnica-Worms
6,365,807 B1 4/2002 Christou et al.
6,384,301 B1 5/2002 Martinell et al.
6,385,902 B1 5/2002 Schipper et al.
6,399,861 B1 6/2002 Anderson et al.
6,403,865 B1 6/2002 Koziel et al.
6,414,222 B1 7/2002 Gengenbach et al.
6,421,956 B1 7/2002 Boukens et al.
6,426,446 B1 7/2002 McElroy et al.
6,433,252 B1 8/2002 Kriz et al.
6,437,217 B1 8/2002 McElroy et al.
6,453,609 B1 9/2002 Soll et al.
6,479,291 B2 11/2002 Kumagai et al.
6,506,559 B1 1/2003 Fire et al.
6,642,435 B1 11/2003 Rafalski et al.
6,644,341 B1 11/2003 Chemo et al.
6,645,914 B1 11/2003 Woznica et al.
6,768,044 B1 7/2004 Boudec et al.
6,992,237 B1 1/2006 Habben et al.
7,022,896 B1 4/2006 Weeks et al.
7,026,528 B2 4/2006 Cheng et al.

(56) References Cited

U.S. PATENT DOCUMENTS

RE39,247 E 8/2006 Barry et al.
7,105,724 B2 9/2006 Weeks et al.
7,119,256 B2 10/2006 Shimizu et al.
7,138,564 B2 11/2006 Tian et al.
7,297,541 B2 11/2007 Moshiri et al.
7,304,209 B2 12/2007 Zink et al.
7,312,379 B2 12/2007 Andrews et al.
7,323,310 B2 1/2008 Peters et al.
7,371,927 B2 5/2008 Yao et al.
7,392,379 B2 6/2008 Le Pennec et al.
7,405,347 B2 7/2008 Hammer et al.
7,406,981 B2 8/2008 Hemo et al.
7,462,379 B2 12/2008 Fukuda et al.
7,485,777 B2 2/2009 Nakajima et al.
7,525,013 B2 4/2009 Hildebrand et al.
7,550,578 B2 6/2009 Budworth et al.
7,622,301 B2 11/2009 Ren et al.
7,657,299 B2 2/2010 Huizenga et al.
7,671,254 B2 3/2010 Tranel et al.
7,714,188 B2 5/2010 Castle et al.
7,738,626 B2 6/2010 Weese et al.
7,807,791 B2 10/2010 Sekar et al.
7,838,263 B2 11/2010 Dam et al.
7,838,733 B2 11/2010 Wright et al.
7,842,856 B2 11/2010 Tranel et al.
7,884,262 B2 2/2011 Clemente et al.
7,910,805 B2 3/2011 Duck et al.
7,935,869 B2 5/2011 Pallett et al.
7,943,819 B2 5/2011 Baum et al.
7,973,218 B2 7/2011 McCutchen et al.
8,090,164 B2 1/2012 Bullitt et al.
8,143,480 B2 3/2012 Axtell et al.
8,226,938 B1 7/2012 Meikle et al.
8,548,778 B1 10/2013 Hart et al.
8,554,490 B2 10/2013 Tang et al.
9,121,022 B2 9/2015 Sammons et al.
9,422,557 B2 8/2016 Ader
9,445,603 B2 9/2016 Baum et al.
9,777,288 B2 10/2017 Beattie et al.
9,850,496 B2 12/2017 Beattie et al.
9,856,495 B2 10/2018 Beattie et al.
2001/0006797 A1 7/2001 Kumagai et al.
2001/0042257 A1 11/2001 Connor-Ward et al.
2002/0069430 A1 6/2002 Kiaska et al.
2002/0114784 A1 8/2002 Li et al.
2003/0150017 A1 8/2003 Mesa et al.
2003/0154508 A1 8/2003 Stevens et al.
2003/0167537 A1 9/2003 Jiang
2004/0029275 A1 2/2004 Brown et al.
2004/0053289 A1 3/2004 Allen et al.
2004/0055041 A1 3/2004 Labate et al.
2004/0072692 A1 4/2004 Hoffman et al.
2004/0082475 A1 4/2004 Hoffman et al.
2004/0123347 A1 6/2004 Hinchey et al.
2004/0126845 A1 7/2004 Eenennaam et al.
2004/0133944 A1 7/2004 Hake et al.
2004/0147475 A1 7/2004 Li et al.
2004/0177399 A1 9/2004 Hammer et al.
2004/0216189 A1 10/2004 Houmard et al.
2004/0244075 A1 12/2004 Cai et al.
2004/0250310 A1 12/2004 Shukla et al.
2005/0005319 A1 1/2005 della-Cioppa et al.
2005/0044591 A1 2/2005 Yao et al.
2005/0215435 A1 9/2005 Menges et al.
2005/0223425 A1 10/2005 Clinton et al.
2005/0246784 A1 11/2005 Plesch et al.
2005/0250647 A1 11/2005 Hills et al.
2005/0289664 A1 12/2005 Moshiri et al.
2006/0009358 A1 1/2006 Kibler et al.
2006/0021087 A1 1/2006 Baum et al.
2006/0040826 A1 2/2006 Eaton et al.
2006/0111241 A1 5/2006 Gerwick, III et al.
2006/0130172 A1 6/2006 Whaley et al.
2006/0135758 A1 6/2006 Wu
2006/0200878 A1 9/2006 Lutfiyya et al.
2006/0223708 A1 10/2006 Hoffman et al.
2006/0223709 A1 10/2006 Helmke et al.
2006/0247197 A1 11/2006 Van De Craen et al.
2006/0272049 A1 11/2006 Waterhouse et al.
2006/0276339 A1 12/2006 Windsor et al.
2007/0011775 A1 1/2007 Allen et al.
2007/0021360 A1 1/2007 Nyce et al.
2007/0050863 A1 3/2007 Tranel et al.
2007/0124836 A1 5/2007 Baum et al.
2007/0199095 A1 8/2007 Allen et al.
2007/0250947 A1 10/2007 Boukharov et al.
2007/0259785 A1 11/2007 Heck et al.
2007/0269815 A1 11/2007 Rivory et al.
2007/0281900 A1 12/2007 Cui et al.
2007/0300329 A1 12/2007 Allen et al.
2008/0022423 A1 1/2008 Roberts et al.
2008/0050342 A1 2/2008 Fire et al.
2008/0092256 A1 4/2008 Kohn
2008/0113351 A1 5/2008 Naito et al.
2008/0155716 A1 6/2008 Sonnewald et al.
2008/0214443 A1 9/2008 Baum et al.
2009/0011934 A1 1/2009 Zawierucha et al.
2009/0018016 A1 1/2009 Duck et al.
2009/0036311 A1 2/2009 Witschel et al.
2009/0054240 A1 2/2009 Witschel et al.
2009/0075921 A1 3/2009 Ikegawa et al.
2009/0098614 A1 4/2009 Zamore et al.
2009/0118214 A1 5/2009 Paldi et al.
2009/0137395 A1 5/2009 Chicoine et al.
2009/0165153 A1 6/2009 Wang et al.
2009/0165166 A1 6/2009 Feng et al.
2009/0172838 A1 7/2009 Axtell et al.
2009/0188005 A1 7/2009 Boukharov et al.
2009/0205079 A1 8/2009 Kumar et al.
2009/0215628 A1 8/2009 Witschel et al.
2009/0285784 A1 11/2009 Raemaekers et al.
2009/0293148 A1 11/2009 Ren et al.
2009/0298787 A1 12/2009 Raemaekers et al.
2009/0306189 A1 12/2009 Raemaekers et al.
2009/0307803 A1 12/2009 Baum et al.
2010/0005551 A1 1/2010 Roberts et al.
2010/0048670 A1 2/2010 Biard et al.
2010/0068172 A1 3/2010 Van De Craen
2010/0071088 A1 3/2010 Sela et al.
2010/0099561 A1 4/2010 Selby et al.
2010/0100988 A1 4/2010 Tranel et al.
2010/0152443 A1 6/2010 Hirai et al.
2010/0154083 A1 6/2010 Ross et al.
2010/0192237 A1 7/2010 Ren et al.
2010/0247578 A1 9/2010 Salama
2010/0248373 A1 9/2010 Baba et al.
2011/0015084 A1 1/2011 Christian et al.
2011/0015284 A1 1/2011 Dees et al.
2011/0028412 A1 2/2011 Cappello et al.
2011/0035836 A1 2/2011 Endes et al.
2011/0041400 A1 2/2011 Trias Vila et al.
2011/0053226 A1 3/2011 Rohayem
2011/0098180 A1 4/2011 Michel et al.
2011/0105327 A1 5/2011 Nelson
2011/0105329 A1 5/2011 Song et al.
2011/0112570 A1 5/2011 Mannava et al.
2011/0126310 A1 5/2011 Feng et al.
2011/0126311 A1 5/2011 Velcheva et al.
2011/0152339 A1 6/2011 Brown et al.
2011/0152346 A1 6/2011 Karleson et al.
2011/0152353 A1 6/2011 Koizumi et al.
2011/0160082 A1 6/2011 Woo et al.
2011/0166022 A1 7/2011 Israels et al.
2011/0166023 A1 7/2011 Nettleton-Hammond et al.
2011/0171176 A1 7/2011 Baas et al.
2011/0171287 A1 7/2011 Saarma et al.
2011/0177949 A1 7/2011 Krapp et al.
2011/0185444 A1 7/2011 Li et al.
2011/0185445 A1 7/2011 Bogner et al.
2011/0191897 A1 8/2011 Poree et al.
2011/0201501 A1 8/2011 Song et al.
2011/0296555 A1 12/2011 Ivashuta et al.
2011/0296556 A1* 12/2011 Sammons .............. A01N 63/02
800/298

(56) References Cited

U.S. PATENT DOCUMENTS

2012/0036594 A1 2/2012 Cardoza et al.
2012/0107355 A1 5/2012 Harris et al.
2012/0108497 A1 5/2012 Paldi et al.
2012/0137387 A1 5/2012 Baum et al.
2012/0150048 A1 6/2012 Kang et al.
2012/0156784 A1 6/2012 Adams, Jr. et al.
2012/0157512 A1 6/2012 Ben-Chanoch et al.
2012/0164205 A1 6/2012 Baum et al.
2012/0174262 A1 7/2012 Azhakanandam et al.
2012/0185967 A1 7/2012 Sela et al.
2012/0198586 A1 8/2012 Narva et al.
2012/0230565 A1 9/2012 Steinberg et al.
2012/0258646 A1 10/2012 Sela et al.
2013/0003213 A1 1/2013 Kabelac et al.
2013/0041004 A1 2/2013 Drager et al.
2013/0047297 A1 2/2013 Sammons et al.
2013/0047298 A1 2/2013 Tang
2013/0060133 A1 3/2013 Kassab et al.
2013/0067618 A1 3/2013 Ader et al.
2013/0084243 A1 4/2013 Goetsch et al.
2013/0096073 A1 4/2013 Sidelman
2013/0097726 A1 4/2013 Ader et al.
2013/0212739 A1 8/2013 Giritch et al.
2013/0226003 A1 8/2013 Edic et al.
2013/0247247 A1 9/2013 Ader et al.
2013/0254940 A1 9/2013 Ader et al.
2013/0254941 A1 9/2013 Ader et al.
2013/0288895 A1 10/2013 Ader et al.
2013/0318657 A1 11/2013 Avniel et al.
2013/0318658 A1 11/2013 Ader et al.
2013/0324842 A1 12/2013 Mittal et al.
2013/0326731 A1 12/2013 Ader et al.
2014/0018241 A1 1/2014 Sammons et al.
2014/0057789 A1 2/2014 Sammons et al.
2014/0109258 A1 4/2014 Van De Craen et al.
2014/0230090 A1 8/2014 Avniel et al.
2014/0274712 A1 9/2014 Finnessy et al.
2014/0275208 A1 9/2014 Hu et al.
2014/0296503 A1 10/2014 Avniel et al.
2015/0096079 A1 4/2015 Avniel et al.
2015/0143580 A1 5/2015 Beattie et al.
2015/0159156 A1 6/2015 Inberg et al.
2015/0203867 A1 7/2015 Beattie et al.
2015/0240258 A1 8/2015 Beattie et al.
2016/0015035 A1 1/2016 Tao
2016/0029644 A1 2/2016 Tao

FOREIGN PATENT DOCUMENTS

CN 101279950 A 10/2008
CN 101279951 A 10/2008
CN 101892247 A 11/2010
CN 101914540 A 12/2010
CN 102154364 A 8/2011
CN 102481311 A 5/2012
CN 102822350 A 12/2012
CN 102906263 A 1/2013
DE 288618 A5 4/1991
DE 10000600 A1 7/2001
DE 10116399 A1 10/2002
DE 10256353 A1 6/2003
DE 10256354 A1 6/2003
DE 10256367 A1 6/2003
DE 10204951 A1 8/2003
DE 10234875 A1 2/2004
DE 10234876 A1 2/2004
DE 102004054666 A1 5/2006
DE 102005014638 A1 10/2006
DE 102005014906 A1 10/2006
DE 102007012168 A1 9/2008
DE 102010042866 A1 5/2011
EP 0 804 600 A1 11/1997
EP 1 155 615 A1 11/2001
EP 1 157 991 A2 11/2001
EP 1 238 586 A1 9/2002
EP 1 416 049 A1 5/2004
EP 1 496 123 A1 1/2005
EP 1 889 902 A1 2/2008
EP 1 964 919 A1 9/2008
EP 2 147 919 A1 1/2010
EP 2 160 098 B1 11/2010
EP 2 530 159 A1 3/2011
EP 2 305 813 A2 4/2011
EP 2 545 182 A1 1/2013
JP 2001253874 A 9/2001
JP 2002080454 A 3/2002
JP 2002138075 A 5/2002
JP 2002145707 A 5/2002
JP 2002220389 A 8/2002
JP 2003064059 A 3/2003
JP 2003096059 A 4/2003
JP 2004051628 A 2/2004
JP 2004107228 A 4/2004
JP 2005008583 A 1/2005
JP 2005239675 A 9/2005
JP 2005314407 A 11/2005
JP 2006232824 A 9/2006
JP 2006282552 A 10/2006
JP 2007153847 A 6/2007
JP 2007161701 A 6/2007
JP 2007182404 A 7/2007
JP 2008074840 A 4/2008
JP 2008074841 A 4/2008
JP 2008133207 A 6/2008
JP 2008133218 A 6/2008
JP 2008169121 A 7/2008
JP 2009-508481 A 3/2009
JP 2009067739 A 4/2009
JP 2009114128 A 5/2009
JP 2009126792 A 6/2009
JP 2009137851 A 6/2009
RU 2 291 613 C1 1/2007
RU 2 337 529 C1 11/2008
WO WO 89/11789 A1 12/1989
WO WO 95/34659 A1 12/1995
WO WO 95/34668 A2 12/1995
WO WO 96/005721 A1 2/1996
WO WO 96/033270 A1 10/1996
WO WO 96/038567 A2 12/1996
WO WO 96/040964 A2 12/1996
WO WO 97/49816 A1 12/1997
WO WO 99/14348 A1 3/1999
WO WO 99/024585 A1 5/1999
WO WO 99/26467 A1 6/1999
WO WO 99/27116 A2 6/1999
WO WO 99/32619 A1 7/1999
WO WO 99/61631 A1 12/1999
WO WO 99/67367 A1 12/1999
WO WO 00/32757 A2 6/2000
WO WO 00/044914 A1 8/2000
WO WO 01/07601 A2 2/2001
WO WO 2001/085970 A2 11/2001
WO WO 02/14472 A2 2/2002
WO WO 02/066660 A2 8/2002
WO WO 03/000679 A2 1/2003
WO WO 03/004649 A1 1/2003
WO WO 03/006422 A1 1/2003
WO WO 03/012052 A2 2/2003
WO WO 03/013247 A1 2/2003
WO WO 03/016308 A1 2/2003
WO WO 2003/014357 A1 2/2003
WO WO 03/020704 A1 3/2003
WO WO 03/022051 A1 3/2003
WO WO 03/022831 A1 3/2003
WO WO 03/022843 A1 3/2003
WO WO 03/029243 A2 4/2003
WO WO 03/037085 A1 5/2003
WO WO 03/037878 A1 5/2003
WO WO 03/045878 A2 6/2003
WO WO 03/050087 A2 6/2003
WO WO 03/051823 A1 6/2003
WO WO 03/051824 A1 6/2003
WO WO 03/051846 A2 6/2003
WO WO 03/064625 A2 8/2003

(56) References Cited

FOREIGN PATENT DOCUMENTS

WO WO 03/076409 A1 9/2003
WO WO 03/077648 A2 9/2003
WO WO 03/087067 A1 10/2003
WO WO 03/090539 A1 11/2003
WO WO 03/091217 A1 11/2003
WO WO 03/093269 A2 11/2003
WO WO 03/104206 A2 12/2003
WO WO 2004/002947 A1 1/2004
WO WO 2004/002981 A2 1/2004
WO WO 2004/005485 A2 1/2004
WO WO 2004/009761 A2 1/2004
WO WO 2004/011429 A1 2/2004
WO WO 2004/022771 A2 3/2004
WO WO 2004/029060 A1 4/2004
WO WO 2004/035545 A2 4/2004
WO WO 2004/035563 A1 4/2004
WO WO 2004/035564 A1 4/2004
WO WO 2004/037787 A1 5/2004
WO WO 2004/049806 A1 6/2004
WO WO 2004/062351 A2 7/2004
WO WO 2004/067518 A1 8/2004
WO WO 2004/067527 A1 8/2004
WO WO 2004/074443 A2 9/2004
WO WO 2004/077950 A1 9/2004
WO WO 2005/000824 A1 1/2005
WO WO 2005/003362 A2 1/2005
WO WO 2005/007627 A1 1/2005
WO WO 2005/007860 A1 1/2005
WO WO 2005/040152 A1 5/2005
WO WO 2005/047233 A1 5/2005
WO WO 2005/047281 A1 5/2005
WO WO 2005/061443 A2 7/2005
WO WO 2005/061464 A1 7/2005
WO WO 2005/068434 A1 7/2005
WO WO 2005/070889 A1 8/2005
WO WO 2005/089551 A1 9/2005
WO WO 2005/095335 A1 10/2005
WO WO 2005/107437 A2 11/2005
WO WO 2005/110068 A2 11/2005
WO WO 2006/006569 A1 1/2006
WO WO 2006/024820 A1 3/2006
WO WO 2006/029828 A1 3/2006
WO WO 2006/029829 A1 3/2006
WO WO 2006/037945 A1 4/2006
WO WO 2006/050803 A1 5/2006
WO WO 2006/074400 A2 7/2006
WO WO 2006/090792 A1 8/2006
WO WO 2006/123088 A2 11/2006
WO WO 2006/125687 A1 11/2006
WO WO 2006/125688 A1 11/2006
WO WO 2006/132270 A1 12/2006
WO WO 2006/138638 A1 12/2006
WO WO 2007/003294 A1 1/2007
WO WO 2007/007316 A1 1/2007
WO WO 2007/024783 3/2007
WO WO 2007/026834 A1 3/2007
WO WO 2007/035650 A2 3/2007
WO WO 2007/038788 A2 4/2007
WO WO 2007/039454 A1 4/2007
WO W0 2007/050715 A2 5/2007
WO WO 2007/051462 A2 5/2007
WO WO 2007/070389 A2 6/2007
WO WO 2007/071900 A1 6/2007
WO WO 2007/074405 A2 7/2007
WO WO 2007/077201 A1 7/2007
WO WO 2007/077247 A1 7/2007
WO WO 2007/080126 A2 7/2007
WO WO 2007/080127 A2 7/2007
WO WO 2007/083193 A2 7/2007
WO WO 2007/096576 A1 8/2007
WO WO 2007/051462 A3 10/2007
WO WO 2007/119434 A1 10/2007
WO WO 2007/134984 A1 11/2007
WO WO 2008/007100 A2 1/2008
WO WO 2008/009908 A1 1/2008
WO WO 2008/029084 A1 3/2008
WO WO 2008/042231 A2 4/2008
WO WO 2008/059948 A1 5/2008
WO WO 2008/063203 A2 5/2008
WO WO 2008/071918 A1 6/2008
WO WO 2008/074991 A1 6/2008
WO WO 2008/084073 A1 7/2008
WO WO 2008/100426 A2 8/2008
WO WO 2008/102908 A1 8/2008
WO WO 2008/148223 A1 12/2008
WO WO 2008/152072 A2 12/2008
WO WO 2008/152073 A2 12/2008
WO WO 2009/000757 A1 12/2008
WO WO 2009/005297 A2 1/2009
WO WO 2009/029690 A1 3/2009
WO WO 2009/035150 A2 3/2009
WO WO 2009/037329 A2 3/2009
WO WO 2009/046384 A1 4/2009
WO WO 2009/060429 A2 5/2009
WO WO 2009/063180 A1 5/2009
WO WO 2009/068170 A2 6/2009
WO WO 2009/068171 A2 6/2009
WO WO 2009/086041 A1 7/2009
WO WO 2009/090401 A2 7/2009
WO WO 2009/090402 A2 7/2009
WO WO 2009/115788 A1 9/2009
WO WO 2009/116558 A1 9/2009
WO WO 2009/125401 A2 10/2009
WO WO 2009/144079 A1 12/2009
WO WO 2009/152995 A1 12/2009
WO WO 2009/153607 A1 12/2009
WO WO 2009/158258 A1 12/2009
WO WO 2010/012649 A1 2/2010
WO WO 2010/026989 A1 3/2010
WO WO 2010/034153 A1 4/2010
WO WO 2010/049270 A1 5/2010
WO WO 2010/049369 A1 5/2010
WO WO 2010/049405 A1 5/2010
WO WO 2010/049414 A1 5/2010
WO WO 2010/056519 A1 5/2010
WO WO 2010/063422 A1 6/2010
WO WO 2010/069802 A1 6/2010
WO WO 2010/078906 A2 7/2010
WO WO 2010/078912 A1 7/2010
WO WO 2010/093788 A2 8/2010
WO WO 2010/104217 A1 9/2010
WO WO 2010/108611 A1 9/2010
WO WO 2010/112826 A2 10/2010
WO WO 2010/116122 A2 10/2010
WO WO 2010/119906 A1 10/2010
WO WO 2010/130970 A1 11/2010
WO WO 2011/001434 A1 1/2011
WO WO 2011/003776 A2 1/2011
WO WO 2011/035874 A1 3/2011
WO WO 2011/045796 A1 4/2011
WO WO 2011/065451 A1 6/2011
WO WO 2011/067745 A2 6/2011
WO WO 2011/075188 A1 6/2011
WO WO 2011/080674 A2 7/2011
WO WO 2011/112570 A1 9/2011
WO WO 2011/132127 A1 10/2011
WO WO 2012/001626 A1 1/2012
WO WO 2012/056401 A1 5/2012
WO WO 2012/092580 A2 7/2012
WO WO 2012/156342 A1 11/2012
WO WO 2012/164100 A2 12/2012
WO WO 2013/010691 A1 1/2013
WO WO 2013/025670 A1 2/2013
WO WO 2013/039990 A1 3/2013
WO WO 2013/040005 A1 3/2013
WO WO 2013/040021 A1 3/2013
WO WO 2013/040033 A1 3/2013
WO WO 2013/040049 A1 3/2013
WO WO 2013/040057 A1 3/2013
WO WO 2013/040116 A9 3/2013
WO WO 2013/040117 A9 3/2013
WO WO 2013/153553 A2 10/2013
WO WO 2013/175480 A1 11/2013
WO WO 2014/022739 A2 2/2014

(56) References Cited

FOREIGN PATENT DOCUMENTS

| | | |
|---|---|---|
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |
| WO | WO 2015/200539 A1 | 12/2015 |

OTHER PUBLICATIONS

Qi et al., "RNA processing enables predictable programming of gene expression," *Nature Biotechnology*, 30:1002-007 (2012).

Swarts et al., "DNA-guided DNA interference by a prokaryotic Argonaute," *Nature*, 507(7491):258-61 (2014).

Swarts et al., "Argonaute of the archaeon *Pyrococcus furiosus* is a DNA-guided nuclease that targets cognate DNA," *Nucleic Acid Res*., 43(10):5120-5129 (2015).

Townsend et al., "High frequency modification of plant genes using engineered zinc finger nucleases," *Nature*, 459:442-445 (2009).

Van der Meer et al., "Promoted analysis of the chalcone synthase (chs A) gene of *Petunia* hybrid: a 67 bp promoter region directs flower-specific expression," *Plant Mol. Biol*., 15:95-109 (1990).

Zipperian et al., "Silicon Carbide Abrasive Grinding," *Quality Matters Newsletter*, PACE Technologies 1(2):1-3 (2002).

Agricultural Chemical Usage 2006 Vegetables Summary, Agricultural Statistics Board, NASS, USDA, pp. 1-372 (2007).

Agrios, Plant Pathology (Second Edition), 2:466-470 (1978).

Alarcón-Reverte et al., "Resistance to ACCase-inhibiting herbicides in the weed *Lolium multiflorum*," Comm. Appl. Biol. Sci., 73(4):899-902 (2008).

Al-Kaff et al., "Plants rendered herbicide-susceptible by cauliflower mosaic virus—elicited suppression of a 35S promoter-regulated transgene," Nature Biotechnology, 18:995-999 (2000).

Amarzguioui et al., "An algorithm for selection of functional siRNA sequences," Biochemical and Biophysical Research Communications, 316:1050-1058 (2004).

Ambrus et al., "The Diverse Roles of RNA Helicases in RNAi," Cell Cycle, 8(21):3500-3505 (2009).

An et al., "Transient RNAi Induction against Endogenous Genes in Arabidopsis Protoplasts Using in Vitro-Prepared Double-Stranded RNA," Biosci Biotechnol Biochem, 69(2):415-418 (2005).

Andersen et al., "Delivery of siRNA from lyophilized polymeric surfaces,"Biomaterials, 29:506-512 (2008).

Andersson et al., "A novel selection system for potato transformation using a mutated AHAS gene," Plant Cell Reports, 22(4):261-267 (2003).

Anonymous, "Resistant Weeds Spur Research Into New Technologies," Grains Research & Development Corporation, 2013.

Anonymous, "A handbook for high-level expression and purification of 6xHis-tagged proteins," The QiaExpressionist, (2003).

Anonymous, "Agronomy Facts 37: Adjuvants for enhancing herbicide performance," pp., 1-8, (Jan. 26, 2000), Web, (Jan 21, 2014).

Anonymous, "Devgen, The mini-Monsanto," KBC Securities (2006).

Anonymous, "Do Monsanto have the next big thing?," Austalian Herbicide Resistance Initiative (AHRI), (Apr. 23, 2013) Web. (Jan. 19, 2015).

Aoki et al., "In Vivo Transfer Efficiency of Antisense Oligonucleotides into the Myocardium Using HVJ-Liposome Method," Biochem Biophys Res Commun, 231:540-545 (1997).

Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).

Artymovich, "Using RNA interference to increase crop yield and decrease pest damage," MMG 445 Basic Biotech., 5(1):7-12 (2009).

Asad et al., "Silicon Carbide Whisker-mediated Plant Transformation," Properties and Applicants of Silicon Carbide, pp. 345-358 (2011).

Ascencio-Ibanez et al., "DNA abrasion onto plants is an effective method for geminivirus infection and virus-induced gene silencing," Journal of Virological Methods, 142:198-203 (2007).

Axtell et al., "A Two-Hit Trigger for siRNA Biogenesis in Plants," Cell, 127:565-577 (2006).

Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).

Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).

Bai et al., "Naturally Occurring Broad-Spectrum Powdery Mildew Resistance in a Central American Tomato Accession Is Caused by Loss of Mlo Function," MPMI, 21(1):30-39 (2008).

Baker, "Chlorophyll Fluorescence: A Probe of Photosynthesis In Vivo," Annu. Rev. Plant Biol., 59:89-113 (2008).

Balibrea et al., "Extracellular Invertase is an Essential Component of Cytokinin-Mediated Delay of Senescence," The Plant Cell, 16(5):1276-1287.

Bannerjee et al., "Efficient production of transgenic potato (*S. tuberosum* L. ssp. *andigena*) plants via *Agrobacterium tumefaciens*-mediated transformation," Plant Sci., 170:732 738 (2006).

Bart et al., "A novel system for gene silencing using siRNAs in rice leaf and stem-derived protoplasts," Plant Methods, 2(13):1-9 (2006).

Basu et al., "Weed genomics: new tools to understand weed biology," Trends in Plant Science, 9(8):391-398 (2004).

Bauer et al., "The major protein import receptor of plastids is essential for chloroplast biogenesis," Nature, 403:203-207 (2000).

Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).

Baulcombe, "RNA silencing in plants," Nature, 431:356-363 (2004).

Baum et al., "Progress Towards RNAi-Mediated Insect Pest Management" Advances in Insect Physiology, 47:249-295 (2014).

Bayer et al., "Programmable ligand-controlled riboregulators of eukaryotic gene expression," Nature Biotechnol., 23(3):337-343 (2005).

Beal, et al., "Second Structural Motif for Recognition of DNA by Oligonucleotide-Directed Triple-Helix Formation," Science, 251:1360-1363 (1992).

Becker et al., "Fertile transgenic wheat from microprojectile bombardment of scutellar tissue," The Plant Journal, 5(2):299-307 (1994).

Bedell et al., "Sorghum Genome Sequencing by Methylation Filtration," PLOS Biology, 3(1):E13/104-115 (2005).

Belhadj et al., "Methyl Jasmonate Induces Defense Responses in Grapevine and Triggers Protection against Erysiphe necator," J. Agric Food Chem., 54:9119-9125 (2006).

Bhargava et al., "Long double-stranded RNA-mediated RNA interference as a tool to achieve site-specific silencing of hypothalamic neuropeptides," Brain Research Protocols, 13:115-125 (2004).

Boletta et al., "High Efficient Non-Viral Gene Delivery to the Rat Kidney by Novel Polycationic Vectors," J. Am Soc. Nephrol., 7:1728 (1996).

Bolognesi et al., "Characterizing the Mechanism of Action of Double-Stranded RNA Activity against Western Corn Rootworm(*Diabrotica virgifera virgifera* LeConte)," PLoS One 7(10):e47534 (2012).

Bolter et al., "A chloroplastic inner envelope membrane protease is essential for plant development," FEBS Letters, 580:789-794 (2006).

Bourgeois et al., "Field and producer survey of ACCase resistant wild oat in Manitoba," Canadian Journal of Plant Science, 709-715 (1997).

Breaker et al., "A DNA enzyme with Mg2+-dependent RNA phosphoesterase activity," Chemistry and Biology, 2:655-660 (1995).

Brodersen et al., "The diversity of RNA silencing pathways in plants," Trends in Genetics, 22(5):268-280 (2006).

Brugière et al., "Glutamine Synthetase in the Phloem Plays a Major Role in Controlling Proline Production," The Plant Cell, 11:1995-2011 (1999).

Burgos et al., "Review: Confirmation of Resistance to Herbicides and Evaluation of Resistance Levels," Weed Science, 61 (1):4-20 (2013).

(56) References Cited

OTHER PUBLICATIONS

Burleigh, "Relative quantitative RT-PCR to study the expression of plant nutrient transporters in arbuscular mycorrhizas," Plant Science, 160:899-904 (2001).
Busch et al., "RNAi for discovery of novel crop protection products," Pflanzenschutz-Nachrichten Bayer, 58(1):34-50 (2005).
Busi et al., "Gene flow increases the initial frequency of herbicide resistance alleles in unselectedpopulations," Agriculture, Ecosystems and Environments, Elsevier, Amsterdam, NL, 142(3):403-409 (2011).
Butler et al., "Priming and re-drying improve the survival of mature seeds of *Digitalis purpurea* during storage," Annals of Botany, 103:1261-1270 (2009).
Bytebier et al., "T-DNA organization in tumor cultures and transgenic plants of the monocotyledon *Asparagus officinalis*," Proc. Natl. Acad. Sci. U.S.A., 84:5345-5349 (1987).
Campbell et al., "Gene-knockdown in the honey bee mite *Varroa destructor* by a non-invasive approach: studies on a glutathione 5-transferase," Parasites & Vectors, 3(1):73, pp. 1-10 (2010).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Dual-target gene silencing by using long, syntheic siRNA duplexes without triggering antiviral responses, " Molecules and Cells, 27(6)689-695 (2009).
Chang et al., "Cellular Internalization of Fluorescent Proteins via Arginine-rich Intracellular Delivery Peptide in Plant Cells," Plant Cell Physiol., 46(3):482-488 (2005).
Chee et al., "Transformation of Soybean (*Glycine max*) by Infecting Germinating Seeds with Agrobacterium tumefaciens," Plant Physiol., 91:1212- 1218 (1989).
Chen et al., "Exploring MicroRNA-Like Small RNAs in the Filamentous Fungus *Fusarium oxysporum*," PLOS One, 9(8):e104956:1-10 (2014).
Chen et al., "In Vivo Analysis of the Role of atTic20 in Protein Import into Chloroplasts," The Plant Cell, 14:641-654 (2002) .
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Cheng et al., "Transient Expression of Minimum Linear Gene Cassettes in Onion Epidermal Cells Via Direct Transformation," Appl Biochem Biotechnol, 159:739-749 (2009).
Cheng et al., "Production of fertile transgenic peanut (Arachis hypogaea L.) plants using Agrobacterium tumefaciens," Plant Cell Reports, 15:653-657 (1996) Hererwith.
Chi et al., "The Function of RH22, a Dead RNA Helicase, in the Biogenesis of the 50S Ribosomal Subunits of Arabidopsis Chloroplasts," Plant Physiology, 158:693-707 (2012).
Christiaens et al., "The challenge of RNAi-mediated control of hemipterans," Current Opinion in Insect Science, 6:15-21 (2014).
Chupp et al., "Chapter 8: White Rusk" Vegetable Diseases and Their Control, The Ronald Press Company, New York, pp. 267-269 (1960).
Clough et al., "Floral dip: a simplified method for Agrobacterium-mediated transformation of *Arabidopsis thaliana*," The Plant Journal, 16(6):735-743.
CN101914540 Patent Disclosure, "Introduction of RNA into plant by interference," (2010).
Colbourne et al., "The Ecoresponsive Genome of Daphnia Pulex," Science, 331(6017):555-561 (2011).
Colliver et al., "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Communication Pursuant to Article 94(3) EPC dated Sep. 5, 2018, in European Patent Application No. 17152830.0.
Concise Descriptions of Relevance filed by a third party on Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cooney et al., "Site-Specific Oligonucleotide Binding Represses Transcription of the Human c-myc Gene in Vitro," Science ,241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," Breast Cancer Res. Treat, 115:545-560 (2009).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* Is Required for Posttranscriptional Gene Silencing Mediated by a Transgene but Not by a Virus," Cell, 101:543-553 (2000).
Danka et al., "Field Test of Resistance to Acarapis woodi (Acari: Tarsonemidae) and of Colony Production by Four Stocks of Honey Bees (Hymenoptera: Apidae)" Journal of Economic Entomology, 88(3):584-591 (1995).
Database EMBL XP-002781749(BG442539) dated Mar. 20, 2001.
Davidson et al., "Engineering regulatory RNAs," Trends in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Della-Cioppa et al., "Import of a precursor protein into chloroplasts is inhibited by the herbicide glyphosate," The EMBO Journal, 7(5):1299-1305 (1988).
Delye et al., "PCR-based detection of resistance to acetyl-CoA carboxylase-inhibiting herbicides in black-grass (*Alopecurus myosuroides* Huds) and ryegrass (*Lolium rigidum* Gaud)," Pest Management Science, 58:474-478 (2002).
Delye et al., "Variation in the gene encoding acetolactate-synthase in *Lolium* species and proactive detection of mutant, herbicide-resistant alleles," Weed Research, 49:326-336 (2009).

(56) References Cited

OTHER PUBLICATIONS

Desai et al., "Reduction in deformed wing virus infection in larval and adult honey bees (*Apis mellifera* L.) by double-stranded RNA ingestion," Insect Molecular Biology, 21(4):446-455 (2012).
Desveaux et al., "PBF-2 Is a Novel Single-Stranded DNA Binding Factor Implicated in PR-10a Gene Activation in Potato," The Plant Cell, 12:1477-1489 (2000).
Di Stilio et al., "Virus-Induced Gene Silencing as a Tool for Comparative Functional Studies in Thalictrum," PLoS One, 5(8):e12064 (2010).
Diallo et al., "Long Endogenous dsRNAs Can Induce Complete Gene Silencing in Mammalian Cells and Primary Cultures," Oligonucleotides, 13:381-392 (2003).
Dietemann et al., "Varroa destructor: research avenues towards sustainable control," Journal of Apicultural Research, 51(1):125-132 (2012).
Dietzgen et al., "Transgenic gene silencing strategies for virus control," Australasian Plant Pathology, 35:605-618 (2006).
Dilpreet et al., "Glyphosate Resistance in a Johnsongrass (*Sorghum halepense*) Biotype from Arkansas," Weed Science, 59(3):299-304 (2011).
Downey et al., "Single and dual parasitic mite infestations on the honey bee, *Apis mellifera* L.," Insectes Sociaux, 47(2):171-176 (2000).
Du et al., "A systematic analysis of the silencing effects of an active siRNA at all single-nucleotide mismatched target sites," Nucleic Acids Research, 33(5):1671-1677 (2005).
Duhoux et al., "Reference Genes to Study Herbicide Stress Response in *Lolium* sp.: Up-Regulation of P3450 Genes in Plants Resistant to Acetolactate-Synthase Inhibitors," PLOS One, 8(5):e63576 (2013).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Egli et al., "A Maize Acetyl-Coenzyme A Carboxylase cDNA Sequence," Plant Physiol., 108: 1299-1300 (1995).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report dated Sep. 7, 2017, in European Patent Application No. 17152830.0.
Examination Report dated Mar. 1, 2018, in Australian Patent Application No. 2013264742.
Extended European Search Report dated Dec. 19, 2018, in European Patent Application No. 16804395.8.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated Nov. 16, 2018, in European Patent Application No. 18182238.8.
Extended European Search Report dated Nov. 21, 2018, in European Patent Application No. 18175809.5.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 28, 2018, in European Patent Application No. 16740770.9.
Extended European Search Report dated Sep. 29, 2016, in European Patent Application No. 14778840.0.
Extended European Search Report dated Apr. 13, 2018, in European Patent Application No. 15812530.0.
Extended European Search Report dated Mar. 15, 2018, in European Patent Application No. 17181861.0.
Farooq et al., "Rice seed priming," IPRN, 30(2):45-48 (2005).
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).

(56) References Cited

OTHER PUBLICATIONS

Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Fukunaga et al., "dsRNA with 5' overhangs v contributes to endogenous and antiviral RNA silencing pathways in plants," The EMBO Journal, 28(5):545-555 (2009).
Funke et al., "Molecular basis for herbicide resistance in Roundup Ready crops," PNAS, 103:13010-13015 (2006).
Further Examination Report dated May 16, 2014, in New Zealand Patent Application No. 601784.
Gaines et al., "Gene amplification confers glyphosate resistance in Amaranthus palmeri," Proc. Natl. Acad. Sci. USA, 107(3):1029-1034 (2010).
Gallie et al., "Identification of the motifs within the tobacco mosaic virus 5'-leader responsible for enhancing translation," Nucleic Acids Res., 20(17):4631-4638 (1992).
Gan et al., "Bacterially expressed dsRNA protects maize against SCMV infection," Plant Cell Rep, 29(11):1261-1268 (2010).
Gan et al "Inhibition of Leaf Senescence by Autoregulated Production of Cytokinin," Science, 270:1986-1988 (1995).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1-9:e1003035 (2012).
Gaskin et al., "Novel organosillicone adjuvants to reduce agrochemical spray volumes on row crops," New Zealand Plant Protection, 53:350-354 (2000).
Gasser et al., "Structure, Expression, and Evolution of the 5-Enolpyruvylshikimate-3-phosphate Synthase Genes of Petunia and Tomato," J. Biol. Chem., 263: 4280-4287 (1988).
Ge et al., "Rapid vacuolar sequestration: the horseweed glyphosate resistance mechanism," Pest Management Sci., 66:345-348 (2010).
GenBank Accession No. AY545657.1 (2004).
GenBank Accession No. CB377464, "CmaEl_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EF143582 (2007).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. FJ972198, "Solanum lycopersicum cultivar Ailsa Craig dihydropterin pyrophosphokinase-dihydropteroate synthase (HPPK-DhHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
GenEmbl Accession No. FJ861243 (2010).
Gilmer et al., "Latent Viruses of Apple I. Detection with Woody Indicators," Plant Pathology, 1(10):1-9 (1971).
Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).
Gong et al., "Silencing of Rieske iron-sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," Pest Manag Sci, 65(7):723-731 (2009).
Gudkov, "Minireview: The L7/L12 ribosomal domain of the ribosome: structural and functional studies," FEBS Letters, 407:253-256 (1997).
Gutensohn et al., "Functional analysis of the two *Arabidopsis* homologues of Toc34, a component of the chloroplast protein import apparatus," The Plant Journal, 23(6):771-783 (2000).
Guttieri et al., "DNA Sequence Variation in Domain A of the Acetolactate Synthase Genes of Herbicide-Resistant and -Susceptible Weed Biotypes," Weed Science, 40:670-679 (1992).
Hagio, "Chapter 25: Direct Gene Transfer into Plant Mature Seeds via Electroporation After Vacuum Treatment," Electroporation and Sonoporation in Developmental Biology, pp. 285-293 (2009).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," Journal of Experimental Botany, 51:439-445 (2000).
Hamilton et al., "Guidelines for the Identification and Characterization of Plant Viruses," J. gen. Virol., 54:223-241 (1981).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature,481:244-251 (2002).
Hardegree, "Drying and storage effects on germination of primed grass seeds," Journal of Range Management, 47(3):196-199 (1994).
Harrison et al., "Does Lowering Glutamine Synthetase Activity in Nodules Modigy Nitrogen Metabolism and Growth of Lotus japonicus?," Plant Physiology, 133:253-262 (2003).
Heffer et al., "Rapid isolation of gene homologs across taxa: Efficient identification and isolation of gene orthologs from non-model organism genomes, a technical report," EvoDevo Journal, 2(7):1-5 (2011).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).

(56) References Cited

OTHER PUBLICATIONS

Himber et al., "Transitivity-dependant and -independent cell-to-cell movement of RNA silencing," The EMBO Journal, 22(17):4523-4533 (2003).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," Plant Physiol., 107(2):469-477 (1995).
Holtra et al., "Assessment of the Physiological Condition of *Salvinia natans* L. Exposed to Copper(II) Ions," Environ. Protect. Eng., 41:147-158 (2015).
Hörmann et al., "Tic32, as Essential Component in Chloroplast Biogenesis," The Journal of Biological Chemistry, 279(33):34756-34762 (2004).
Hsieh et al., "A library of siRNA duplexes targeting the phosphoinositide 3-kinase pathway: determinants of gene silencing for use in cell-based screens," Nucleic Acids Res., 32(3):893-901 (2004).
Hu et al., "High efficiency transport of quantum dots into plant roots with the aid of silwet L-77," Plant Physiology and Biochemistry, 48:703-709 (2010).
Huang et al., "In Vivo Analyses of the Roles of Essential Omp85-Related Proteins in the Chloroplast Outer Envelope Membrane," Plant Physiol., 157:147-159 (2011).
Huesken et al., "Design of a genome-wide siRNA library using an artificial neural network," Nature Biotechnology, 23(8): 995-1001 (2005).
Huggett et al., "Real-time RT-PCR normalisation; strategies and considerations," Genes and Immunity, 6:279-284 (2005).
Hunter et al., "RNA Interference Strategy to suppress Psyllids & Leafhoppers," International Plant and Animal Genome XIX, 15-19 (2011).
Ichihara et al., "Thermodynamic instability of siRNA duplex is a prerequisite for dependable prediction of siRNA activities," Nucleic Acids Res., 35(18):e123 (2007).
Inaba et al., "*Arabidopsis* Tic110 Is Essential for the Assembly and Function of the Protein Import Machinery of Plastids," The Plant Cell, 17:1482-1496 (2005).
International Preliminary Report on Patentability (Chapter II) dated Jul. 24, 2015, in International Application No. PCT/US2014/047204.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Jarvis et al, "An *Arabidopsis* mutant defective in the plastid general protein import apparatus," Science, 282:100-103 (1998).
Ji et al., "Regulation of small RNA stability: methylation and beyond," Cell Research, 22:624-636 (2012).
Jiang et al., Chapter III Seeds and Seedlings, Botany, Northwest A&F University Press, pp. 87-92 (2009).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jofre-Garfias et al., "Agrobacterium-mediated transformation of Amaranthus hypochondriacus: light- and tissue-specific expression of a pea chlorophyll a/b-binding protein promoter," Plant Cell Reports, 16:847-852 (1997).
Jones-Rhoades et al., "MicroRNAs and Their Regulatory Roles in Plants," Annu. Rev. Plant Biol., 57:19-53 (2006).
Josse et al., "A DELLA in Disguise: SPATULA Restrains the Growth of the Developing *Arabidopsis* Seedling," Plant Cell, 23:1337-1351 (2011).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kam et al., "Nanotube Molecular Transporters: Internalization of Carbon Nanotube-Protein Conjugates into Mammalian Cells," J. Am. Chem. Soc., 126(22):6850-6851 (2004).

(56) References Cited

OTHER PUBLICATIONS

Kambiranda et al., "Relationship Between Acid Invertase Activity and Sugar Content in Grape Species," Journal of Food Biochemistry, 35:1646-1652 (2011).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," J. Amer. Soc. Hort. Sci., 117(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kikkert et al., "Stable Transformation of Plant Cells by Particle Bombardment/Biolistics," Methods in Molecular Biology, 286:61-78 (2005).
Kim et al., "Optimization of Conditions for Transient Agrobacterium-Mediated Hererwith Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Kirkwood, "Herbicides and Plants," Botanical Journal of Scotland, 46(3):447-462 (1993).
Kirkwood, "Recent developments in our understanding of the plant cuticle as a barrier to the foliar uptake of pesticides," *Pestic Sci*, 55:69-77 (1999).
Kirkwood, "Use and Mode of Action of Adjuvants for Herbicides: A Review of some Current Work," Pestic Sci., 38:93-102 (1993).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Knudsen, "Promoter2.0: for the recognition of PolI promoter sequences," Bioniformatics, 15(5):356-361 (1999).
Kovacheva et al., "Further in vivo studies on the role of the molecular chaperone, Hsp93, in plastid protein import," The Plant Journal, 50:364-379 (2007).
Kovacheva et al., "In vivo studies on the roles of Tic100, Tic40 and Hsp93 during chloroplast protein import," The Plant Journal, 41:412-428 (2005).
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Kumar et al., "Sequencing, De Novo Assembly and Annotation of the Colorado Potato Beetle, *Leptinotarsa decemlineata*, Transcriptome," PLoS One, 9(1):e86012 (2014).
Kusaba et al., "Low glutelin content1: A Dominant Mutation That Suppresses The Glutelin Multigene Family via RNA Silencing ni Rice," The Plant Cell, 15(6):1455-1467 (2003).
Kusaba, "RNA interference in crop plants," Curr Opin Biotechnol, 15(2):139-143 (2004).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Lein et al., "Target-based discovery of novel herbicides," Current Opinion in Plant Biology, 7:219-225 (2004).
Leopold et al., "Chapter 4: Moisture as a Regulator of Physiological Reaction in Seeds," Seed Moisture, CSSA Special Publication No. 14, pp. 51-69 (1989).
Lermontova et al., "Reduced activity of plastid protoporphyrinogen oxidase causes attenuated photodynamic damage during high-light compared to low-light exposure," The Plant Journal, 48(4):499-510 (2006).
Lesnik et al., "Prediction of rho-independent transcriptional terminators in *Escherichia coli*," Nucleic Acids Research, 29(17):3583-3594 (2001).
Li et al., "A Simplified Seed Transformation Method for Obtaining Transgenic *Brassica napus* Plants," Agricultural Sciences in China, 8(6):658-663 (2009).
Li et al., "Establishment of a highly efficient transformation system for pepper (*Capsicum annuum* L.)," Plant Cell Reports, 21: 785-788 (2003).
Li et al., "The FAST technique: a simplified Agrobacterium-based transformation method for transient gene expression analysis in seedlings of *Arabidopsis* and other plant species," Plant Methods, 5(6):1-15 (2009).
Li et at., "Long dsRNA but not siRNA initiates RNAi in western corn rootworm larvae and adults," Journal of Applied Entomology, 139(6):432-445 (2015).
Liu et al, "The Helicase and RNaseIIIa Domains of *Arabidopsis* Dicer-Like1 Modulate Catalytic Parameters during MicroRNA Biogenesis," Plant Physiology, 159:748-758 (2012).
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films," Bioelectrochemistry, 70:301-307 (2007).
Liu et al., "DNAzyme-mediated recovery of small recombinant RNAs from a 5S rRNA-derived chimera expressed in *Escherichia coli*," BMC Biotechnology, 10:85 (2010).
Liu et al., "Identification and Application of a Rice Senescence-Associated Promoter," Plant Physiology, 153:1239-1249 (2010).
Liu, "Calmodulin and Cell Cycle," Foreign Medical Sciences Section of Pathophysiology and Clinical Medicine, 18(4):322-324 (1998).
Liu, "Confocal laser scanning microscopy—an attractive tool for studying the uptake of xenobiotics into plant foliage," Journal of Microscopy, 213(Pt 2):87-93 (2004).
Liu, "Influence of Sugars on the Foliar Uptake of Bentazone and Glyphosate," New Zealand Plant Protection, 55:159-162 (2002).
Liu, "The Transformation of Nucleic Acid Degradants in Plants," China Organic Fertilizers, Agriculture Press, ISBN: 7-1091634 (1991) (with English translation).
Llave et al., "Endogenous and Silencing-Associated Small RNAs in Plants," The Plant Cell, 14:1605-1619 (2002).
Lodish et al., Molecular Cell Biology, Fourth Edition, p. 210 (2000).
Lu et al., "OligoWalk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Lucas et al., "Plasmodesmata—bridging the gap between neighboring plant cells," Trends in Cell Biology, 19:495-503 (2009).
Luft, "Making sense out of antisense oligodeoxynucleotide delivery: getting there is half the fun," J Mol Med, 76:75-76 (1998).
Luque et al., "Water Permeability of Isolated Cuticular Membranes: A Structural Analysis," Archives of Biochemistry and Biophysics, 317(2):417- 422 (1995).
Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167-2170 (1990).
Maher III et al., "Inhibition of DNA binding proteins by oligonucleotide-directed triple helix formation," Science, 245(4919):725-730 (1989).
Makkouk et al., "Virus Diseases of Peas, Beans, and Faba Bean in the Mediterranean region," Adv Virus Res, 84:367-402 (2012).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).

(56) References Cited

OTHER PUBLICATIONS

Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Maori et al., "IAPV, a bee-affecting virus associated with Colony Collapse Disorder can be silenced by dsRNA ingestion," Insect Molecular Biology, 18(1):55-60 (2009).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," Transgenic Research, 5:313-323 (1996).
Matveeva et al., "Prediction of antisense oligonucleotide efficacy by in vitro methods," Nature Biotechnology, 16:1374-1375 (1998).
McGinnis, "RNAi for functional genomics in plants," Brief Funct Genomics, 9(2):111-7 (2010).
Meinke, et al., "Identifying essential genes in *Arabidopsis thaliana*," Trends Plant Sci., 13(9):483-491 (2008).
Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (1994).
Misawa et al., "Functional expression of the Erwinia uredovora carotenoid biosynthesis gene crtl in transgenic plants showing an increase of β-carotene biosynthesis activity and resistance to the bleaching herbicide norflurazon," The Plant Journal, 4(5):833-840 (1993).
Miura et al., "The Balance between Protein Synthesis and Degradation in Chloroplasts Determines Leaf Variegation in Arabidopsis yellow variegated Mutants," The Plant Cell, 19:1313-1328 (2007).
Molina et al., "Inhibition of protoporphyrinogen oxidase expression in *Arabidopsis* causes a lesion-mimic phenotype that induces systemic acquired resistance," The Plant Journal, 17(6):667-678 (1999).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants Are Mobile and Direct Epigenetic Modification in Recipient Cells," Science, 328:872-875 (2010).
Mora et al., "How Many Species Are There on Earth and in the Ocean?," PLOS Biol., 9(8):e100127, p. 1-8 (2011).
Moriyama et al., "Double-stranded RNA in rice: A novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Morrissey et al., "Potent and persistent in vivo anti-HBV activity of chemically modified siRNAs," Nat Biotechnol. 23(8):1002-1007 (2005).
Moser et al., "Sequence-Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505- 1528 (2009).
Nemeth, "Virus, mycoplasma and rickettsia diseases of fruit trees," Martinus Nijhoff Publishers, 197-204 (1986).
Non-Final Office Action dated Apr. 11, 2013, in U.S. Appl. No. 13/042,856.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.

(56) References Cited

OTHER PUBLICATIONS

Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
Nowak et al., "A new and efficient method for inhibition of RNA viruses by DNA interference," The FEBS Journal, 276:4372-4380 (2009).
N-TER Nanoparticle siRNA, Sigma Aldrich TM website, Web. Nov. 20, 2018 <https://www.sigmaaldrich.com/life-science/custom-oligos/sirna-oligos/n-ter-nanoparticle.html>.
Office Action dated Apr. 13, 2016, in Chinese Patent Application No. 201280053985.3.
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Aug. 9, 2018, in Canadian Patent Application No. 2,848,371.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. 1 2014 03849.
Office Action dated Dec. 27, 2016, in Ukrainian Patent Application No. a 2012 11548.
Office Action dated Dec. 5, 2017, in Japanese Patent Application No. 2016-502033.
Office Action dated Feb. 17, 2014, in Mexican Patent Application No. MX/a/2012/010479.
Office Action dated Feb. 21, 2018, in Mexican Patent Application No. MX/a/2015/012632 (with English translation).
Office Action dated Feb. 24, 2014, in Eurasian Patent Application No. 201201264.
Office Action dated Jul. 11, 2017, in Mexican Patent Application No. MX/a/2015/013118 (with English translation).
Office Action dated Jul. 18, 2016, in Indonesian Patent Application No. W00201203610.
Office Action dated Jul. 23, 2015, in Ukrainian Patent Application No. 201211548.
Office Action dated Jul. 3, 2017, in Mexican Patent Application No. MX/a/2015/012632 (with English translation).
Office Action dated Jul. 30, 2018, in Canadian Patent Application No. 2,848,576.
Office Action dated Jul. 6, 2017, in Mexican Patent Application No. MX/a/2015/013103 (with English translation).
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated Mar. 8, 2018 (with English translation), in Chilean Patent Application No. 201403192.
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 20, 2018, in Chilean Patent Application No. 201601440 (with English translation).
Office Action dated Sep. 5, 2016, in Ukrainian Patent Application No. a 2014 03846.
Office Action dated Sep. 6, 2017, in Chinese Patent Application No. 2014800154012 (with English translation).
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Paddison et al., "Stable suppression of gene expression by RNAi in mammalian cells," Proc. Natl Acad. Sci. USA, 99(3):1443-1448 (2002).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Jun. 29, 2018, in European Patent Application No. 18157745.3.
Partial European Search Report dated Dec. 6, 2017, in European Patent Application No. 17181861.0.
Partial Supplementary European Search Report dated Jan. 11, 2018, in European Patent Application No. 15812530.2.
Partial Supplementary European Search Report dated Mar. 2, 2015, in European Patent Application No. 12 831 494.5.
Partial Supplementary European Search Report dated Jan. 11, 2018, in European Patent Application No. 15812530.0.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308660.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).
Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).

(56) References Cited

OTHER PUBLICATIONS

Pratt et al., "Sorghum Expressed Sequence Tags Identify Signature Genes for Drought, Pathogenesis, and Skotomorphogenesis from a Milestone Set of 16,801 Unique Transcripts," Plant Physiology, 139:869-884 (2005).
Pratt et al., "Amaranthus rudis and A. tuberculatus, One Species or Two?," Journal of the Torrey Botanical Society, 128(3):282-296 (2001).
Preston et al., "Multiple effects of a naturally occuring proline to threonine substitution within acetolactate synthase in two herbicide-resistant populations of Lactuca serriola," Pesticide Biochem. Physiol., 84(3):227-235 (2006).
Promoter Prediction for SEQ ID No: 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Qi et al., "RNA processing enables predictable programming of gene expression," *Nature Biotechnology*, 30:1002-1007 (2012).
Qiwei,"Advance in DNA interference," Progress in Veterinary Medicine, 30(1):71-75 (2009).
Rajur et al., "Covalent Protein—Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).
Reddy et al "Organosilicone Adjuvants Increased the Efficacy of Glyphosate for Control of Weeds in Citrus (*Citrus* spp.)" HortScience 27(9):1003-1005 (1992).
Reddy et al., "Aminomethylphosphonic Acid Accumulation in Plant Species Treated with Glyphosate," J. Agric. Food Chem., 56(6):2125-2130 (2008).
Regalado, "The Next Great GMO Debate," MIT Technology Review,pp. 1-19 (2015) <https://www.technologyreview.com/s/540136/the-next-great-gmo- debate/>.
Reither et al., "Specificity of DNA triple helix formation analyzed by a FRET assay," BMC Biochemistry, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 13, 2016, in U.S. Appl. No. 14/206,707.
Restriction Requirement dated Oct. 2, 2012, in U.S. Appl. No. 13/042,856.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Reverdatto et al., "A Multisubunit Acetyl Coenzyme A Carboxylase from Soybean," Plant Physiol., 119: 961-978 (1999).
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Ruan et al., "Suppression of Sucrose Synthase Gene Expression Represses Cotton Fiber Cell Initiation, Elongation, and Seed Development," The Plant Cell, 15:952-964 (2003).
Ryabov et al., "Cell-to-Cell, but Not Long-Distance, Spread of RNA Silencing That Is Induced in Individual Epidermal Cells," Journal of Virology, 78(6):3149-3154 (2004).
Ryan, "Human endogenous retroviruses in health and disease: a symbiotic perspective," Journal of the Royal Society of Medicine, 97:560-565 (2004).
Salanenka et al., "Seedcoat Permeability: Uptake and Post-germination Transport of Applied Model Tracer Compounds," HortScience, 46(4):622-626 (2011).
Sammataro et al., "Some Volatile Plant Oils as Potential Control Agents for Varroa Mites (Acari: Varroidae) in Honey Bee Colonies (Hymenoptera: Apidae)," American Bee Journal, 138(9):681-685 (1998).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," NucleicAcids Research, 18(8):2188-2193 (1990).
Schönherr et al., "Size selectivity of aqueous pores in astomatous cuticular membranes isolated from Populus canescens (Aiton) Sm. Leaves," Planta, 219:405-411 (2004).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Schwember et al., "Drying Rates following Priming Affect Temperature Sensitivity of Germination and Longevity of Lettuce Seeds," HortScience, 40(3):778-781 (2005).
Scott et al., Botanical Insecticides for Controlling Agricultural Pests: Piperamides and the Colorado Potato Beetle *Leptinotarsa*

(56) References Cited

OTHER PUBLICATIONS

*decemlineata* Say (Coleoptera: Chrysomelidae), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A systematic study to determine the extent of gene silencing in *Nicotiana benthamiana* and other *Solanaceae* species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al. "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Simeoni et al., "Insight into the mechanism of the peptide-based gene delivery system MPG: implications for delivery of siRNA into mammalian cells," Nucleic Acids Research, 31(11):2717-2724 (2003).
Singh et al., "Absorption and translocation of glyphosate with conventional and organosilicone adjuvants," Weed Biology and Management, 8:104-111 (2008).
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Song et al., "Herbicide," New Heterocyclic Pesticide, Chemical Industry Press, 354-356 (2011).
Statement of Grounds and Particulars dated Sep. 1, 2017, in Australian Patent No. 2014262189.
Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—Silwet® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, pp. 24(1):27-34 (1994).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street, "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.
Sun et al., "A Highly efficient Transformation Protocol for Micro-Tom, a Model Cultivar for Tomato Functional Genomics," Plant Cell Physiol., 47(3):426-431 (2006).
Sun et al., "Antisense oligodeoxynucleotide inhibition as a potent strategy in plant biology: identification of SUSIBA2 as a transcriptional activator in plant sugar signalling," The Plant Journal, 44:128-138 (2005).
Sun et al., "Sweet delivery—sugar translocators as ports of entry for antisense oligodeoxynucleotides in plant cells," The Plant Journal, 52:1192-1198 (2007).
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Sutton et al., "Activity of mesotrione on resistant weeds in maize," Pest Manag. Sci., 58:981-984 (2002).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Temple et al., "Down-regulation of specific members of the glutamine synthetase gene family in Alfalfa by antisense RNA technology," Plant Molecular Biology, 37:535-547 (1998).
Templeton et al., "Improved DNA: liposome complexes for increased systemic delivery and gene expression," Nature Biotechnology, 15:647-652 (1997).
Teng et al., "Tic21 Is an Essential Translocon Component for Protein Translocation across the Chloroplast Inner Envelope Membrane," The Plant Cell, 18:2247-2257 (2006).
Tenllado et al., "Crude extracts of bacterially expressed dsRNA can be used to protect plants against virus infection," BMC Biotechnology, 3(3):1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856
Thomas et al., "Size constraints for targeting post-transcriptional gene silencing and for RNA-directed methylation in Nicotiana benthamiana using a potato virus X vector," The Plant Journal, 25(4):417-425 (2001).
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Tice, "Selecting the right compounds for screening: does Lipinski's Rule of 5 for pharmaceuticals apply to agrochemicals?" Pest Management Science, 57(1):3-16 (2001).
Timmons et al., "Specific interference by ingested dsRNA," Nature, 395:854 (1998).
Tomari et al., "Perspective: machines for RNAi," Genes & Dev., 19:517-529 (2005).

(56) References Cited

OTHER PUBLICATIONS

Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany, 55(406):2291-2303 (2004).
Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," Bio/Technology, 6:1072-1074 (1988).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
Trucco et al., "Amaranthus hybridus can be pollinated frequently by A. tuberculatus under filed conditions," Heredity, 94:64-70 (2005).
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Ulrich et al., "Large scale RNAi screen in Tribolium reveals novel target genes for pest control and the proteasome as prime target," BMC genomics, 16(1):671 (2015).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination In Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Urayama et al., "Knock-down of OsDCL2 in Rice Negatively Affects Maintenance of the Endogenous dsRNA Virus, *Oryza sativa* Endornavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).
Wan et al., "Generation of Large Numbers Of Independently Transformed Fertile Barley Plants," Plant Physiol., 104:37-48 (1994).
Wang et al., "Foliar uptake of pesticides—Present status and future challenge," ScienceDirect, 87:1-8 (2007).
Wang et al., "Principle and technology of genetic engineering in plants," in Plant genetic engineering principles and techniques, Beijing: Science Press, pp. 313-315 (1998).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Watson et al., "RNA silencing platforms in plants," FEBS Letters, 579:5982-5987 (2005).
Welch et al., "Expression of ribozymes in gene transfer systems to modulate target RNA levels," Curr Opin Biotechnol. 9(5):486-496 (1998).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot Noxious Weed Control Board (NWCB) of Washington State (2010) <www.nwcb.wa.gov/detail.asp?weed=46>.
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Wool et al., "Structure and evolution of mammalian ribosomal proteins," Biochem. Cell Biol., 73:933-947 (1995).
Written Opinion dated Apr. 7, 2016, in Singapore Patent Application No. 201206152-9.
Written Opinion dated Mar. 6, 2017, in Singaporean Patent Application No. 2012061529.
Written Opinion dated May 8, 2014, in International Application No. PCT/IL2013/050447.
Written Opinion dated Sep. 1, 2014, in Singapore Patent Application No. 201206152-9.
Xu et al., "Characterization and Functional Analysis of the Calmodulin-Binding Domain of Rac1 GTPase," PLoS One, 7(8):e42975 (2012).
Yan et al., Seed Science, China Agriculture Press, pp. 101-103, Tables 2-37 (2001).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Yu et al., "Diversity of Acetyl-Coenzyme A Carboxylase Mutations in Resistant Lolium Populations: Evaluation Using Clethodim," Plant Physiology, 145:547-558 (2007).
Yu et al., "Glyphosate, paraquat and ACCase multiple herbicide resistance evolved in a Lolium rigidum biotype," Planta, 225:499-513 (2007).
Zabkiewicz, "Adjuvants and herbicidal efficacy—present status and future prospects," Weed Research, 40:139-149 (2000).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).

(56) References Cited

OTHER PUBLICATIONS

Zhang et al., "Progress in research of honey bee mite *Varro destructor*," Journal of Environmental Entomology, 34(3):345-353 (2012).
Zhang et al., "A novel rice gene, NRR responds to macronutrient deficiency and regulates root growth," Mol Plant, 5(1):63-72 (2012).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhao et al., "Ps0rl, a potential target for RNA interference-based pest management," Insect Molecular Biology, 20(1):97-104 (2011).
Zhao et al., "Phyllotreta striolata (Coleoptera: Chrysomelidae): Arginine kinase cloning and RNAi-based pest control," European Journal of Entomology, 105(5):815-822 (2008).
Zhao et al., "Vegetable Statdardized Production Technology," Hangzhou: Zhejiang Science and Technology Press, p. 19 (2008).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Zhong et al., "A pea antisense gene for the chloroplast stromal processing peptidase yields seedling lethals in *Arabidopsis*: survivors show defective GFP import in vivo," The Plant Journal, 34:802-812 (2003).
Zhu et al., "Ingested RNA interference for managing the populations of the Colorado potato beetle, *Leptinotarsa decemlineata*," Pest Manag Sci, 67:175-182 (2010).
Zotti et al., "RNAi technology for insect management and protection of beneficial insects from diseases: lessons, challenges and risk assessments," Neotropical Entomology, 44(3):197-213 (2015).

* cited by examiner

SEQUENCE LISTING

<160> NUMBER OF SEQ ID NOS: 32

<210> SEQ ID NO 1
<211> LENGTH: 50
<212> TYPE: RNA
<213> ORGANISM: artificial sequence
<220> FEATURE:
<223> OTHER INFORMATION: synthetic construct

<400> SEQUENCE: 1
gaauugggac aacuccagug aaaaguucuu cuccuuuacu gaauucggcc 50

<210> SEQ ID NO 2
<211> LENGTH: 78
<212> TYPE: RNA
<213> ORGANISM: artificial sequence
<220> FEATURE:
<223> OTHER INFORMATION: synthetic construct

<400> SEQUENCE: 2
guacccauua acaucaccau cuaauucaac aagaauuggg acaacuccag ugaaaaguuc 60
uucuccuuua cugaauuc 78

<210> SEQ ID NO 3
<211> LENGTH: 124
<212> TYPE: RNA
<213> ORGANISM: artificial sequence
<220> FEATURE:
<223> OTHER INFORMATION: synthetic construct

<400> SEQUENCE: 3
guauguugca ucaccuucac ccucuccacu gacagaaaau uuguacccau uaacaucacc 60
aucuaauuca acaagaauug ggacaacucc agugaaaagu ucuucuccuu uacugaauuc 120
ggcc 124

<210> SEQ ID NO 4
<211> LENGTH: 125
<212> TYPE: RNA
<213> ORGANISM: artificial sequence
<220> FEATURE:
<223> OTHER INFORMATION: synthetic construct

<400> SEQUENCE: 4
gucuuguagu ucccgucguc cuugaagaag augguccucu ccugcacgua ucccucaggc 60
auggcgcucu ugaagaaguc gugccgcuuc auaugaucug gguaucuuga aaagcauuga 120
acacc 125

<210> SEQ ID NO 5
<211> LENGTH: 249
<212> TYPE: RNA
<213> ORGANISM: artificial sequence
<220> FEATURE:
<223> OTHER INFORMATION: synthetic construct

<400> SEQUENCE: 5
guugugggag uuguaguugu auuccaacuu guggccgagg auguuuccgu ccuccuugaa 60
aucgauuccc uuaagcucga uccuguugac gagggugucu cccucaaacu ugacuucagc 120
acgugucuug uaguucccgu cguccuugaa gaagaugguc cucuccugca cguaucccuc 180
aggcauggcg cucuugaaga agucgugccg cuucauauga ucuggguauc uugaaaagca 240
uugaacacc 249

<210> SEQ ID NO 6
<211> LENGTH: 258
<212> TYPE: RNA
<213> ORGANISM: artificial sequence
<220> FEATURE:
<223> OTHER INFORMATION: synthetic construct

<400> SEQUENCE: 6
guuccuucca cugcaaccga ucguuaaucc cuaguucucc aaacagguuc ugcauauuug 60
gguaagcccc aaagaauaug ugcaacccag ucucguacca aucuccauca ucaucuuucc 120
augcagcuac cuuuccaccu aggacaucuc uugccuccag caauaucggu uugugaccag 180
caucugccag auauuuugcu guagacaagc cacccaaacc ugcaccagca auaacaaucu 240
ccaaugguuu uguugggc 258

<210> SEQ ID NO 7
<211> LENGTH: 300
<212> TYPE: RNA
<213> ORGANISM: artificial sequence
<220> FEATURE:
<223> OTHER INFORMATION: synthetic construct

<400> SEQUENCE: 7
ggaaucucca ucaucaucuu uccaugcagc uaccuuucca ccuaggacau cucuugccuc 60
cagcaauauc gguuugugac cagcaucugc cagauauuuu gcuguagaca agccacccaa 120
accugcacca gcaauaacaa ucuccaaugg caaauaaauu uaaggguaag uuuuccguau 180
guugcaucac cuucacccuc uccacugaca gaaaauuugu acccauuaac aucaccaucu 240
aauucaacaa gaauugggac aacuccagug aaaaguucuu cuccuuuacu gaauucggcc 300

<210> SEQ ID NO 8
<211> LENGTH: 355
<212> TYPE: RNA
<213> ORGANISM: artificial sequence
<220> FEATURE:
<223> OTHER INFORMATION: synthetic construct

<400> SEQUENCE: 8
cgcuuucgcu ugcguuucuu ggcccugcug guguugaccg guccgaacgg gggcagaucg 60
augcuuuggg uuugaagacg gcucaaaacc aucuucauga agggucguuc cgaagggcug 120
guuccgcugc ucguucaugg uucccacuau ccuaucucau cauguguaua uauguaaucc 180
augggggagg guuucucucg ucuuugagau aggcuugugg uuugcaugac cgaggagcug 240
caccgccccc uugcuggccg cucuugaagu uggcuuugau gccgucaucc ugauccaccc 300
cuccauuuuu uuugcuuguu guguccuucc ugggaccuga gaucugaggc ucgug 355

<210> SEQ ID NO 9
<211> LENGTH: 7985
<212> TYPE: DNA
<213> ORGANISM: artificial sequence
<220> FEATURE:
<223> OTHER INFORMATION: synthetic construct

<400> SEQUENCE: 9
atccatcaca ctggcggccg ctcgagcatg catctagagg gcccaattcg ccctatagtg 60
agtcgtatta caattcactg gccgtcgttt tacaacgtcg tgactgggaa aaccctggcg 120
ttacccaact taatcgcctt gcagcacatc ccccttttcgc cagctggcgt aatagcgaag 180

```
aggcccgcac cgatcgccct tcccaacagt tgcgcagcct gaatggcgaa tgggacgcgc    240
cctgtagcgg cgcattaagc gcggcgggtg tggtggttac gcgcagcgtg accgctacac    300
ttgccagcgc cctagcgccc gctcctttcg ctttcttccc ttcctttctc gccacgttcg    360
ccggctttcc ccgtcaagct ctaaatcggg ggctcccttt agggttccga tttagagctt    420
tacggcacct cgaccgcaaa aaacttgatt tgggtgatgg ttcacgtagt gggccatcgc    480
cctgatagac ggtttttcgc cctttgacgt tggagtccac gttctttaat agtggactct    540
tgttccaaac tggaacaaca ctcaacccta tcgcggtcta ttcttttgat ttataaggga    600
ttttgccgat ttcggcctat tggttaaaaa atgagctgat ttaacaaatt cagggcgcaa    660
gggctgctaa aggaaccgga acacgtagaa agccagtccg cagaaacggt gctgaccccg    720
gatgaatgtc agctactggg ctatctggac aagggaaaac gcaagcgcaa agagaaagca    780
ggtagcttgc agtgggctta catggcgata gctagactgg gcggttttat ggacagcaag    840
cgaaccggaa ttgccagctg gggcgccctc tggtaaggtt gggaagccct gcaaagtaaa    900
ctggatggct ttcttgccgc caaggatctg atggcgcagg ggatcaagat ctgatcaaga    960
gacaggatga ggatcgtttc gcatgattga acaagatgga ttgcacgcag gttctccggc   1020
cgcttgggtg gagaggctat tcggctatga ctgggcacaa cagacaatcg gctgctctga   1080
tgccgccgtg ttccggctgt cagcgcaggg gcgcccggtt ctttttgtca agaccgacct   1140
gtccggtgcc ctgaatgaac tgcaggacga ggcagcgcgg ctatcgtggc tggccacgac   1200
gggcgttcct tgcgcagctg tgctcgacgt tgtcactgaa gcgggaaggg actggctgct   1260
attgggcgaa gtgccggggc aggatctcct gtcatctcgc cttgctcctg ccgagaaagt   1320
atccatcatg gctgatgcaa tgcggcggct gcatacgctt gatccggcta cctgcccatt   1380
cgaccaccaa gcgaaacatc gcatcgagcg agcacgtact cggatggaag ccggtcttgt   1440
cgatcaggat gatctggacg aagagcatca ggggctcgcg ccagccgaac tgttcgccag   1500
gctcaaggcg cgcatgcccg acggcgagga tctcgtcgtg atccatggcg atgcctgctt   1560
gccgaatatc atggtggaaa atggccgctt ttctggattc aacgactgtg gccggctggg   1620
tgtggcggac cgctatcagg acatagcgtt ggatacccgt gatattgctg aagagcttgg   1680
cggcgaatgg gctgaccgct tcctcgtgct ttacggtatc gccgctcccg attcgcagcg   1740
catcgccttc tatcgccttc ttgacgagtt cttctgaatt gaaaaaggaa gagtatgagt   1800
attcaacatt tccgtgtcgc ccttattccc ttttttgcgg cattttgcct tcctgttttt   1860
gctcacccag aaacgctggt gaaagtaaaa gatgctgaag atcagttggg tgcacgagtg   1920
ggttacatcg aactggatct caacagcggt aagatccttg agagttttcg ccccgaagaa   1980
cgttttccaa tgatgagcac ttttaaagtt ctgctatgtc atacactatt atcccgtatt   2040
gacgccgggc aagagcaact cggtcgccgg gcgcggtatt ctcagaatga cttggttgag   2100
tactcaccag tcacagaaaa gcatcttacg gatggcatga cagtaagaga attatgcagt   2160
gctgccataa ccatgagtga taacactgcg gccaacttac ttctgacaac gatcggagga   2220
ccgaaggagc taaccgcttt tttgcacaac atgggggatc atgtaactcg ccttgatcgt   2280
tgggaaccgg agctgaatga agccatacca aacgacgaga gtgacaccac gatgcctgta   2340
gcaatgccaa caacgttgcg caaactatta actggcgaac tacttactct agcttcccgg   2400
caacaattaa tagactggat ggaggcggat aaagttgcag gaccacttct gcgctcggcc   2460
cttccggctg gctggtttat tgctgataaa tctggagccg gtgagcgtgg gtctcgcggt   2520
atcattgcag cactggggcc agatggtaag ccctcccgta tcgtagttat ctacacgacg   2580
```

-continued

```
gggagtcagg caactatgga tgaacgaaat agacagatcg ctgagatagg tgcctcactg   2640
attaagcatt ggtaactgtc agaccaagtt tactcatata tactttagat tgatttaaaa   2700
cttcattttt aatttaaaag gatctaggtg aagatccttt ttgataatct catgaccaaa   2760
atcccttaac gtgagttttc gttccactga gcgtcagacc ccgtagaaaa gatcaaagga   2820
tcttcttgag atcctttttt tctgcgcgta atctgctgct tgcaaacaaa aaaaccaccg   2880
ctaccagcgg tggtttgttt gccggatcaa gagctaccaa ctctttttcc gaaggtaact   2940
ggcttcagca gagcgcagat accaaatact gtccttctag tgtagccgta gttaggccac   3000
cacttcaaga actctgtagc accgcctaca tacctcgctc tgctaatcct gttaccagtg   3060
gctgctgcca gtggcgataa gtcgtgtctt accgggttgg actcaagacg atagttaccg   3120
gataaggcgc agcggtcggg ctgaacgggg ggttcgtgca cacagcccag cttggagcga   3180
acgacctaca ccgaactgag atacctacag cgtgagcatt gagaaagcgc cacgcttccc   3240
gaagggagaa aggcggacag gtatccggta agcggcaggg tcggaacagg agagcgcacg   3300
agggagcttc caggggggaaa cgcctggtat ctttatagtc ctgtcgggtt tcgccacctc   3360
tgacttgagc gtcgattttt gtgatgctcg tcaggggggc ggagcctatg gaaaaacgcc   3420
agcaacgcgg cctttttacg gttcctggcc ttttgctggc cttttgctca catgttcttt   3480
cctgcgttat cccctgattc tgtggataac cgtattaccg cctttgagtg agctgatacc   3540
gctcgccgca gccgaacgac cgagcgcagc gagtcagtga gcgaggaagc ggaagagcgc   3600
ccaatacgca aaccgcctct ccccgcgcgt tggccgattc attaatgcag ctggcacgac   3660
aggtttcccg actggaaagc gggcagtgag cgcaacgcaa ttaatgtgag ttagctcact   3720
cattaggcac cccaggcttt acactttatg cttccggctc gtatgttgtg tggaattgtg   3780
agcggataac aatttcacac aggaaacagc tatgaccatg attacgccaa gcttggtacc   3840
gagctcggat cccctcgagt ggaggagctt ggtcgagtgg aagctagcgg taccaagctt   3900
tcctcacgtt gtggttgaac ctgatctgca cgtggtatat cctgatgttc gtgtatagga   3960
gatcctctac gttgtatatc ttgaaataga ggggatttgg aacatcccaa ataaaaacgc   4020
cattccctgc ttgatgagca gtgatgggtt cccctgtgcg tgaatccatt attggcgcag   4080
ttgatgtgca cgtatattga acagccgcag tccaagtcta tacgttttcg acgtattccc   4140
tttcgttttg caatcctgtg tttaggtttg atagaggggg gcgtcgagga agacgaattt   4200
tgcattgtga agtgtccacg ccttgagatg tgagttttcc tgtttgtcga ggtagtattt   4260
atagctagcc ccctcaccag gattgcatag cacgattgat ggaatgccac ctttaatttg   4320
aatgggtttc ccgtatttac agttggtctg ccagtctgtc tgggccccaa tgagctcttt   4380
ccagtgtttc atctttagat aatgcggtgg tacgtcatca atgacgttgt acataacatt   4440
atttgagtaa accctagaat tgaaatctag atgaccactc agataattat gaattcctaa   4500
tgaacgagcc cacattgttt ttccagttct tgaatcacct tcgatgataa tactgatagg   4560
tcttaaagtc cgcgcagcgg caccatttcc aaaataatca tcagcccatg tctgtaactc   4620
ctctggcacg ttattaaatg aggaaagtgg aaatggagga acccacggtt ctggagcctt   4680
tgaaaatatc ttctcaaggt tacccttgag attgtgaaaa tctttaacaa aatccctagg   4740
ttgttcttcc tttaaaattt ggagtgcttc ttgcactcca actgcgttaa gcgcctttgc   4800
atatgaatcg tttgcagtct gctggcctcc cctagcagat ctgccgtcga tttggaattc   4860
tccccattcg agggtatctc catctttgtc gatgtatgat ttgacgtcgg aactagattt   4920
```

-continued

```
agctccctga atgttcggat ggaaatatgc tgacctggtt ggggatacca ggtcgaactg   4980
tcgttcgttg gtgatctgga ctttcccttc aagttggata agggcatgga tatgaggttc   5040
cccattctcg tgaagctctc tgcaaatctt gatataacgt ttattcgaag ttagttgtat   5100
tgactgtaat tgctctaacg cttcatcttt tgtgagcgag catagtgggt atgttaggaa   5160
gatatttttg gcttgaagtc tgaaacgtct tggtagtggc atatttgtaa attaagggtg   5220
tactccaatt gagctcctca aaacttggtg aaacaattgg agtattggag tacaatttat   5280
actaaaacct cagatagcgc ttggagacac gtggcggcca tccgtttata atattaccgg   5340
atggccgcgc gatttttttac ccgatccggg cccattaatg aattaatgtt gggtcatgca   5400
atgatggtaa atatgactgt ccaatcacat gacgtctgct tggtctaatt agtggtcctt   5460
ggtagacaag aatggacccg gatatctata aatattaaag tgaatcccac tattgtatat   5520
ctttaatttg aaatgacgcg tcttaagacc ggtaggaaga gcttcaggaa aatcaaagcg   5580
gctgaactcc cctggcttgt taggcatcgc aaatatcatt gaatgttcct tccactgcaa   5640
ccgatcatca atccctagtt ctccaaacag gttctgcata tttgggtaag ccccaaagaa   5700
tatgtgcaac ccagtctcgt accaatctcc atcatcatct ttccatgcag ctaccttccc   5760
acctaggaca tctcttgcct ccagcaatat cggtttgtga ccagcatctg ccagatattt   5820
tgctgtagac aaaccaccca aacctgcacc agcaataaca atctccaatg gtttagttgg   5880
gcgtgaggaa gtacgaaacg atgatgataa taacgccgcc tccaaatagt taactgtatt   5940
gtctagctct ggtcttggat aatcaatgca gactaccttt aaaggattaa agtcctttgt   6000
caatcttcgg gtcgtggcac ttggagtacg aatccttaac ttatgcccca tggagtcgct   6060
actaccaaaa cataacaaat tcctttgcaa gcaaacatct tgactttcag ttcccaacga   6120
agacctcgag ctccaaagat aagctgaatt accgcgggtc gacacgcgtt aattaataaa   6180
ttttgaattt tattgaatgt ctttctaata cgtgatttac atatggttta tctgttgcga   6240
agcgaacagc acgaatgaca ttattaagtg aaataacacc taatctatct aagtacaata   6300
aaactaaact cctaaaccga ttcaaataag tcgtcccaga agccgtcagg gatgtcgtcc   6360
agacttggaa atttaggtat gccttgtgta gatccaaagc tttcctcacg ttgtggttga   6420
acctgatctg cacgtggtat atcctgatgt tcgtgtatag gagatcctct acgttgtata   6480
tcttgaaata gaggggattt ggaacatccc aaataaaaac gccattccct gcttgatgag   6540
cagtgatggg ttcccctgtg cgtgaatcca ttattggcgc agttgatgtg cacgtatatt   6600
gaacagccgc agtccaagtc tatacgtttt cgacgtattc cctttcgttt tgcaatcctg   6660
tgtttaggtt tgatagaggg gggcgtcgag gaagacgaat tttgcattgt gaagtgtcca   6720
cgccttgaga tgtgagtttt cctgtttgtc gaggtagtat ttatagctag ccccctcacc   6780
aggattgcat agcacgattg atggaatgcc acctttaatt tgaatgggtt tcccgtattt   6840
acagttggtc tgccagtctg tctgggcccc aatgagctct ttccagtgtt tcatctttag   6900
ataatgcggt ggtacgtcat caatgacgtt gtacataaca ttatttgagt aaaccctaga   6960
attgaaatct agatgaccac tcagataatt atgaattcct aatgaacgag cccacattgt   7020
ttttccagtt cttgaatcac cttcgatgat aatactgata ggtcttaaag tccgcgcagc   7080
ggcaccattt ccaaaataat catcagccca tgtctgtaac tcctctggca cgttattaaa   7140
tgaggaaagt ggaaatggag gaacccacgg ttctggagcc tttgaaaata tcttctcaag   7200
gttacccttg agattgtgaa aatctttaac aaaatcccta ggttgttctt cctttaaaat   7260
ttggagtgct tcttgcactc caactgcgtt aagcgccttt gcatatgaat cgtttgcagt   7320
```

```
ctgctggcct cccctagcag atctgccgtc gatttggaat tctccccatt cgagggtatc   7380

tccatctttg tcgatgtatg atttgacgtc ggaactagat ttagctccct gaatgttcgg   7440

atggaaatat gctgacctgg ttggggatac caggtcgaac tgtcgttcgt tggtgatctg   7500

gactttccct tcaagttgga taagggcatg gatatgaggt tccccattct cgtgaagctc   7560

tctgcaaatc ttgatataac gtttattcga agttagttgt attgactgta attgctctaa   7620

cgcttcatct tttgtgagcg agcatagtgg gtatgttagg aagatatttt tggcttgaag   7680

tctgaaacgt cttggtagtg gcatatttgt aaattaaggg tgtactccaa ttgagctcct   7740

caaaacttgg tgaaacaatt ggagtattgg agtacaattt atactaaaac ctcagatagc   7800

gcttggagac acgtggcggc catccgttta taatattacc ggatggccgc gcgatttttt   7860

acccgatccg ggcccattaa tgaattaatg ttgggtcatg caatgatggt aaatatgact   7920

gtccaatcac atgacgtctg cttggtctaa ttagtggtcc ttggtagaca agaatggacc   7980

cggat                                                               7985
```

```
<210> SEQ ID NO 10
<211> LENGTH: 7984
<212> TYPE: DNA
<213> ORGANISM: artificial sequence
<220> FEATURE:
<223> OTHER INFORMATION: synthetic construct

<400> SEQUENCE: 10
```

```
atccatcaca ctggcggccg ctcgagcatg catctagagg gcccaattcg ccctatagtg     60

agtcgtatta caattcactg gccgtcgttt tacaacgtcg tgactgggaa aaccctggcg    120

ttacccaact taatcgcctt gcagcacatc ccccttcgc cagctggcgt aatagcgaag    180

aggcccgcac cgatcgccct tcccaacagt tgcgcagcct gaatggcgaa tgggacgcgc    240

cctgtagcgg cgcattaagc gcggcgggtg tggtggttac gcgcagcgtg accgctacac    300

ttgccagcgc cctagcgccc gctcctttcg ctttcttccc ttcctttctc gccacgttcg    360

ccggctttcc ccgtcaagct ctaaatcggg ggctcccttt agggttccga tttagagctt    420

tacggcacct cgaccgcaaa aaacttgatt tgggtgatgg ttcacgtagt gggccatcgc    480

cctgatagac ggtttttcgc cctttgacgt tggagtccac gttctttaat agtggactct    540

tgttccaaac tggaacaaca ctcaacccta tcgcggtcta ttcttttgat ttataaggga    600

ttttgccgat ttcggcctat tggttaaaaa atgagctgat ttaacaaatt cagggcgcaa    660

gggctgctaa aggaaccgga acacgtagaa agccagtccg cagaaacggt gctgaccccg    720

gatgaatgtc agctactggg ctatctggac aagggaaaac gcaagcgcaa agagaaagca    780

ggtagcttgc agtgggctta catggcgata gctagactgg gcggttttat ggacagcaag    840

cgaaccggaa ttgccagctg gggcgccctc tggtaaggtt gggaagccct gcaaagtaaa    900

ctggatggct ttcttgccgc caaggatctg atggcgcagg ggatcaagat ctgatcaaga    960

gacaggatga ggatcgtttc gcatgattga acaagatgga ttgcacgcag gttctccggc   1020

cgcttgggtg gagaggctat tcggctatga ctgggcacaa cagacaatcg gctgctctga   1080

tgccgccgtg ttccggctgt cagcgcaggg gcgcccggtt ctttttgtca agaccgacct   1140

gtccggtgcc ctgaatgaac tgcaggacga ggcagcgcgg ctatcgtggc tggccacgac   1200

gggcgttcct tgcgcagctg tgctcgacgt tgtcactgaa gcgggaaggg actggctgct   1260

attgggcgaa gtgccggggc aggatctcct gtcatctcgc cttgctcctg ccgagaaagt   1320
```

-continued

```
atccatcatg gctgatgcaa tgcggcggct gcatacgctt gatccggcta cctgcccatt   1380
cgaccaccaa gcgaaacatc gcatcgagcg agcacgtact cggatggaag ccggtcttgt   1440
cgatcaggat gatctggacg aagagcatca ggggctcgcg ccagccgaac tgttcgccag   1500
gctcaaggcg cgcatgcccg acggcgagga tctcgtcgtg atccatggcg atgcctgctt   1560
gccgaatatc atggtggaaa atggccgctt ttctggattc aacgactgtg gccggctggg   1620
tgtggcggac cgctatcagg acatagcgtt ggatacccgt gatattgctg aagagcttgg   1680
cggcgaatgg gctgaccgct tcctcgtgct ttacggtatc gccgctcccg attcgcagcg   1740
catcgccttc tatcgccttc ttgacgagtt cttctgaatt gaaaaaggaa gagtatgagt   1800
attcaacatt tccgtgtcgc ccttattccc ttttttgcgg cattttgcct tcctgttttt   1860
gctcacccag aaacgctggt gaaagtaaaa gatgctgaag atcagttggg tgcacgagtg   1920
ggttacatcg aactggatct caacagcggt aagatccttg agagttttcg ccccgaagaa   1980
cgttttccaa tgatgagcac ttttaaagtt ctgctatgtc atacactatt atcccgtatt   2040
gacgccgggc aagagcaact cggtcgccgg gcgcggtatt ctcagaatga cttggttgag   2100
tactcaccag tcacagaaaa gcatcttacg gatggcatga cagtaagaga attatgcagt   2160
gctgccataa ccatgagtga taacactgcg gccaacttac ttctgacaac gatcggagga   2220
ccgaaggagc taaccgcttt tttgcacaac atgggggatc atgtaactcg ccttgatcgt   2280
tgggaaccgg agctgaatga agccatacca aacgacgaga gtgacaccac gatgcctgta   2340
gcaatgccaa caacgttgcg caaactatta actggcgaac tacttactct agcttcccgg   2400
caacaattaa tagactggat ggaggcggat aaagttgcag gaccacttct gcgctcggcc   2460
cttccggctg gctggtttat tgctgataaa tctggagccg gtgagcgtgg gtctcgcggt   2520
atcattgcag cactggggcc agatggtaag ccctcccgta tcgtagttat ctacacgacg   2580
gggagtcagg caactatgga tgaacgaaat agacagatcg ctgagatagg tgcctcactg   2640
attaagcatt ggtaactgtc agaccaagtt tactcatata tactttagat tgatttaaaa   2700
cttcattttt aatttaaaag gatctaggtg aagatccttt ttgataatct catgaccaaa   2760
atcccttaac gtgagttttc gttccactga gcgtcagacc ccgtagaaaa gatcaaagga   2820
tcttcttgag atcctttttt tctgcgcgta atctgctgct tgcaaacaaa aaaaccaccg   2880
ctaccagcgg tggtttgttt gccggatcaa gagctaccaa ctctttttcc gaaggtaact   2940
ggcttcagca gagcgcagat accaaatact gtccttctag tgtagccgta gttaggccac   3000
cacttcaaga actctgtagc accgcctaca tacctcgctc tgctaatcct gttaccagtg   3060
gctgctgcca gtggcgataa gtcgtgtctt accgggttgg actcaagacg atagttaccg   3120
gataaggcgc agcggtcggg ctgaacgggg ggttcgtgca cacagcccag cttggagcga   3180
acgacctaca ccgaactgag atacctacag cgtgagcatt gagaaagcgc cacgcttccc   3240
gaagggagaa aggcggacag gtatccggta agcggcaggg tcggaacagg agagcgcacg   3300
agggagcttc cagggggaaa cgcctggtat ctttatagtc ctgtcgggtt tcgccacctc   3360
tgacttgagc gtcgattttt gtgatgctcg tcaggggggc ggagcctatg gaaaaacgcc   3420
agcaacgcgg cctttttacg gttcctggcc ttttgctggc cttttgctca catgttcttt   3480
cctgcgttat cccctgattc tgtggataac cgtattaccg cctttgagtg agctgatacc   3540
gctcgccgca gccgaacgac cgagcgcagc gagtcagtga gcgaggaagc ggaagagcgc   3600
ccaatacgca aaccgcctct ccccgcgcgt tggccgattc attaatgcag ctggcacgac   3660
aggtttcccg actggaaagc gggcagtgag cgcaacgcaa ttaatgtgag ttagctcact   3720
```

```
cattaggcac cccaggcttt acactttatg cttccggctc gtatgttgtg tggaattgtg   3780
agcggataac aatttcacac aggaaacagc tatgaccatg attacgccaa gcttggtacc   3840
gagctcggat cccctcgagt ggaggagctt ggtcgagtgg aagctagcgg taccaagctt   3900
tcctcacgtt gtggttgaac ctgatctgca cgtggtatat cctgatgttc gtgtatagga   3960
gatcctctac gttgtatatc ttgaaataga ggggatttgg aacatcccaa ataaaaacgc   4020
cattccctgc ttgatgagca gtgatgggtt cccctgtgcg tgaatccatt attggcgcag   4080
ttgatgtgca cgtatattga acagccgcag tccaagtcta tacgttttcg acgtattccc   4140
tttcgttttg caatcctgtg tttaggtttg atagaggggg gcgtcgagga agacgaattt   4200
tgcattgtga agtgtccacg ccttgagatg tgagttttcc tgtttgtcga ggtagtattt   4260
atagctagcc ccctcaccag gattgcatag cacgattgat ggaatgccac ctttaatttg   4320
aatgggtttc ccgtatttac agttggtctg ccagtctgtc tgggccccaa tgagctcttt   4380
ccagtgtttc atctttagat aatgcggtgg tacgtcatca atgacgttgt acataacatt   4440
atttgagtaa accctagaat tgaaatctag atgaccactc agataattat gaattcctaa   4500
tgaacgagcc cacattgttt ttccagttct tgaatcacct tcgatgataa tactgatagg   4560
tcttaaagtc cgcgcagcgg caccatttcc aaaataatca tcagcccatg tctgtaactc   4620
ctctggcacg ttattaaatg aggaaagtgg aaatggagga acccacggtt ctggagcctt   4680
tgaaaatatc ttctcaaggt tacccttgag attgtgaaaa tctttaacaa aatccctagg   4740
ttgttcttcc tttaaaattt ggagtgcttc ttgcactcca actgcgttaa gcgcctttgc   4800
atatgaatcg tttgcagtct gctggcctcc cctagcagat ctgccgtcga tttggaattc   4860
tccccattcg agggtatctc catctttgtc gatgtatgat ttgacgtcgg aactagattt   4920
agctccctga atgttcggat ggaaatatgc tgacctggtt ggggatacca ggtcgaactg   4980
tcgttcgttg gtgatctgga ctttcccttc aagttggata agggcatgga tatgaggttc   5040
cccattctcg tgaagctctc tgcaaatctt gatataacgt ttattcgaag ttagttgtat   5100
tgactgtaat tgctctaacg cttcatcttt tgtgagcgag catagtgggt atgttaggaa   5160
gatatttttg gcttgaagtc tgaaacgtct tggtagtggc atatttgtaa attaagggtg   5220
tactccaatt gagctcctca aaacttggtg aaacaattgg agtattggag tacaatttat   5280
actaaaacct cagatagcgc ttggagacac gtggcggcca tccgtttata atattaccgg   5340
atggccgcgc gattttttac ccgatccggg cccattaatg aattaatgtt gggtcatgca   5400
atgatggtaa atatgactgt ccaatcacat gacgtctgct tggtctaatt agtggtcctt   5460
ggtagacaag aatggacccg gatatctata aatattaaag tgaatcccac tattgtatat   5520
ctttaatttg aaatgacgcg tcttaagacc ggttgtctgg taaaaggaca gggccatcgc   5580
caattggagt attttgttga taatgatcag cgagttgcac gccgccgtct tcgatgttgt   5640
ggcgggtctt gaagttggct ttgatgccgt tcttttgctt gtcggccatg atgtatacgt   5700
tgtgggagtt gtagttgtat tccaacttgt ggccgaggat gtttccgtcc tccttgaaat   5760
cgattccctt aagctcgatc ctgttgacga gggtgtctcc ctcaaacttg acttcagcac   5820
gtgtcttgta gttcccgtcg tccttgaaga agatggtcct ctcctgcacg tatccctcag   5880
gcatggcgct cttgaagaag tcgtgccgct tcatatgatc tgggtatctt gaaaagcatt   5940
gaacaccata agagaaagta gtgacaagtg ttggccatgg aacaggtagt tttccagtag   6000
tgcaaataaa tttaagggta agttttccgt atgttgcatc accttcaccc tctccactga   6060
```

```
cagaaaattt gtacccatta acatcaccat ctaattcaac aagaattggg acaactccag   6120
tgaaaagttc ttctccttta ctgaattcgg ccgcgggtcg acacgcgtta attaataaat   6180
tttgaatttt attgaatgtc tttctaatac gtgatttaca tatggtttat ctgttgcgaa   6240
gcgaacagca cgaatgacat tattaagtga aataacacct aatctatcta agtacaataa   6300
aactaaactc ctaaaccgat tcaaataagt cgtcccagaa gccgtcaggg atgtcgtcca   6360
gacttggaaa tttaggtatg ccttgtgtag atccaaagct ttcctcacgt tgtggttgaa   6420
cctgatctgc acgtggtata tcctgatgtt cgtgtatagg agatcctcta cgttgtatat   6480
cttgaaatag aggggatttg gaacatccca aataaaaacg ccattccctg cttgatgagc   6540
agtgatgggt tcccctgtgc gtgaatccat tattggcgca gttgatgtgc acgtatattg   6600
aacagccgca gtccaagtct atacgttttc gacgtattcc ctttcgtttt gcaatcctgt   6660
gtttaggttt gatagagggg ggcgtcgagg aagacgaatt ttgcattgtg aagtgtccac   6720
gccttgagat gtgagttttc ctgtttgtcg aggtagtatt tatagctagc cccctcacca   6780
ggattgcata gcacgattga tggaatgcca cctttaattt gaatgggttt cccgtattta   6840
cagttggtct gccagtctgt ctgggcccca atgagctctt tccagtgttt catctttaga   6900
taatgcggtg gtacgtcatc aatgacgttg tacataacat tatttgagta aaccctagaa   6960
ttgaaatcta gatgaccact cagataatta tgaattccta atgaacgagc ccacattgtt   7020
tttccagttc ttgaatcacc ttcgatgata atactgatag gtcttaaagt ccgcgcagcg   7080
gcaccatttc caaaataatc atcagcccat gtctgtaact cctctggcac gttattaaat   7140
gaggaaagtg gaaatggagg aacccacggt tctggagcct ttgaaaatat cttctcaagg   7200
ttacccttga gattgtgaaa atctttaaca aaatccctag gttgttcttc ctttaaaatt   7260
tggagtgctt cttgcactcc aactgcgtta agcgcctttg catatgaatc gtttgcagtc   7320
tgctggcctc ccctagcaga tctgccgtcg atttggaatt ctccccattc gagggtatct   7380
ccatctttgt cgatgtatga tttgacgtcg gaactagatt tagctccctg aatgttcgga   7440
tggaaatatg ctgacctggt tggggatacc aggtcgaact gtcgttcgtt ggtgatctgg   7500
actttccctt caagttggat aagggcatgg atatgaggtt ccccattctc gtgaagctct   7560
ctgcaaatct tgatataacg tttattcgaa gttagttgta ttgactgtaa ttgctctaac   7620
gcttcatctt ttgtgagcga gcatagtggg tatgttagga agatattttt ggcttgaagt   7680
ctgaaacgtc ttggtagtgg catatttgta aattaagggt gtactccaat tgagctcctc   7740
aaaacttggt gaaacaattg gagtattgga gtacaattta tactaaaacc tcagatagcg   7800
cttggagaca cgtggcggcc atccgtttat aatattaccg gatggccgcg cgattttta    7860
cccgatccgg gcccattaat gaattaatgt tgggtcatgc aatgatggta aatatgactg   7920
tccaatcaca tgacgtctgc ttggtctaat tagtggtcct tggtagacaa gaatggaccc   7980
ggat                                                                7984
```

<210> SEQ ID NO 11
<211> LENGTH: 7808
<212> TYPE: DNA
<213> ORGANISM: artificial sequence
<220> FEATURE:
<223> OTHER INFORMATION: synthetic construct

<400> SEQUENCE: 11

```
gaattcactg gccgtcgttt tacaacgtcg tgactgggaa aaccctggcg ttacccaact     60
taatcgcctt gcagcacatc cccctttcgc cagctggcgt aatagcgaag aggcccgcac    120
```

-continued

```
cgatcgccct tcccaacagt tgcgcagcct gaatggcgaa tggcgcctga tgcggtattt    180
tctccttacg catctgtgcg gtatttcaca ccgcatatgg tgcactctca gtacaatctg    240
ctctgatgcc gcatagttaa gccagccccg acacccgcca acacccgctg acgcgccctg    300
acgggcttgt ctgctcccgg catccgctta cagacaagct gtgaccgtct ccgggagctg    360
catgtgtcag aggttttcac cgtcatcacc gaaacgcgcg agacgaaagg gcctcgtgat    420
acgcctattt ttataggtta atgtcatgat aataatggtt tcttagacgt caggtggcac    480
ttttcgggga aatgtgcgcg gaacccctat ttgtttattt ttctaaatac attcaaatat    540
gtatccgctc atgagacaat aaccctgata aatgcttcaa taatattgaa aaaggaagag    600
tatgagtatt caacatttcc gtgtcgccct tattcccttt tttgcggcat tttgccttcc    660
tgtttttgct cacccagaaa cgctggtgaa agtaaaagat gctgaagatc agttgggtgc    720
acgagtgggt tacatcgaac tggatctcaa cagcggtaag atccttgaga gttttcgccc    780
cgaagaacgt tttccaatga tgagcacttt taaagttctg ctatgtggcg cggtattatc    840
ccgtattgac gccgggcaag agcaactcgg tcgccgcata cactattctc agaatgactt    900
ggttgagtac tcaccagtca cagaaaagca tcttacggat ggcatgacag taagagaatt    960
atgcagtgct gccataacca tgagtgataa cactgcggcc aacttacttc tgacaacgat   1020
cggaggaccg aaggagctaa ccgctttttt gcacaacatg ggggatcatg taactcgcct   1080
tgatcgttgg gaaccggagc tgaatgaagc cataccaaac gacgagcgtg acaccacgat   1140
gcctgtagca atggcaacaa cgttgcgcaa actattaact ggcgaactac ttactctagc   1200
ttcccggcaa caattaatag actggatgga ggcggataaa gttgcaggac cacttctgcg   1260
ctcggccctt ccggctggct ggtttattgc tgataaatct ggagccggtg agcgtgggtc   1320
tcgcggtatc attgcagcac tggggccaga tggtaagccc tcccgtatcg tagttatcta   1380
cacgacgggg agtcaggcaa ctatggatga acgaaataga cagatcgctg agataggtgc   1440
ctcactgatt aagcattggt aactgtcaga ccaagtttac tcatatatac tttagattga   1500
tttaaaactt catttttaat ttaaaaggat ctaggtgaag atcctttttg ataatctcat   1560
gaccaaaatc ccttaacgtg agttttcgtt ccactgagcg tcagaccccg tagaaaagat   1620
caaaggatct tcttgagatc cttttttttct gcgcgtaatc tgctgcttgc aaacaaaaaa   1680
accaccgcta ccagcggtgg tttgtttgcc ggatcaagag ctaccaactc tttttccgaa   1740
ggtaactggc ttcagcagag cgcagatacc aaatactgtt cttctagtgt agccgtagtt   1800
aggccaccac ttcaagaact ctgtagcacc gcctacatac ctcgctctgc taatcctgtt   1860
accagtggct gctgccagtg gcgataagtc gtgtcttacc gggttggact caagacgata   1920
gttaccggat aaggcgcagc ggtcgggctg aacggggggt tcgtgcacac agcccagctt   1980
ggagcgaacg acctacaccg aactgagata cctacagcgt gagctatgag aaagcgccac   2040
gcttcccgaa gggagaaagg cggacaggta tccggtaagc ggcagggtcg gaacaggaga   2100
gcgcacgagg gagcttccag ggggaaacgc ctggtatctt tatagtcctg tcgggtttcg   2160
ccacctctga cttgagcgtc gatttttgtg atgctcgtca ggggggcgga gcctatggaa   2220
aaacgccagc aacgcggcct ttttacggtt cctggccttt tgctggcctt ttgctcacat   2280
gttctttcct gcgttatccc ctgattctgt ggataaccgt attaccgcct ttgagtgagc   2340
tgataccgct cgccgcagcc gaacgaccga gcgcagcgag tcagtgagcg aggaagcgga   2400
agagcgccca atacgcaaac cgcctctccc cgcgcgttgg ccgattcatt aatgcagctg   2460
```

```
gcacgacagg tttcccgact ggaaagcggg cagtgagcgc aacgcaatta atgtgagtta   2520
gctcactcat taggcacccc aggctttaca ctttatgctt ccggctcgta tgttgtgtgg   2580
aattgtgagc ggataacaat ttcacacagg aaacagctat gaccatgatt acgccaagct   2640
tgcatgcctg caggtcgact ctagaggatc cccgggtacc gagctcaatt ggagtacacc   2700
cattaattac aaatatgcca ctaccaagaa gttctctcac tacaactcgg gaatgaacac   2760
tcattgttta gattaaacac aaatatttat aaatagacat atgcatatct ataccagaca   2820
cgcaattctt cttaaaaaag ctcttcatta gctgccttat catctcttcc gcatagataa   2880
ttttctgtaa gggtgccgct gcgcggactt atttttaata tatggattct cagttagtta   2940
atcctcctaa cgcattcaat tacatagagt ctcaccgaga cgagtatcag ctttctcatg   3000
acttaactga gataataatg caattcccgt cgacggcatc acagttaaca gctagactta   3060
gccggagctg catgaagatc gaccattgcg tcatagaata caggcaacag gttccgatta   3120
acgccacggg ttcagtgata gtggagatcc acgacaaaag aatgacagac aacgaatctc   3180
tacaatcatc atggactttc ccaatcagat gcaacataga tctccattat ttctcggctt   3240
cgtttttctc attgaaggac ccgattccat ggaaactgta ttacagagtt tgtgatacaa   3300
atgtgcacca gagaactcac ttcgcgaagt tcaaagggaa actgaagctc tcgacggcga   3360
aacactcagt ggatatcccc ttccgggcac caacggtaaa gatattatcc aaacagttca   3420
ctgataaaga tgtggacttt tcacatgtcg actatgggaa atgggaacgg aagcccatca   3480
gatgcgcatc catgtcgaga cttgggctta gaggcccaat tgaaataagg ccaggtgaat   3540
catgggcttc tagaagtaca ttgggtaatg ggctttcaga tgcagactcc gaagagcaga   3600
acgagataca tccatacagg cacctaaaca gactaggaac aacaatatta gacacaggag   3660
agtctgcatc agttgtagga gcacagaaag cggattccaa catcacaatg acaatgggcc   3720
aattaaacga attagttagg actacggtac acgagtgtat aaacagtaat tgtaaggctt   3780
cacagcccaa gtcattaaaa taaatatcat tattggttat ttcattaata gattattcaa   3840
tatatggaat acatattaaa ttttattact catccaacat aatctagatc aaatgataca   3900
aatgtagatg ccttagatat cgtatctgac atccaacaat aataaactaa cagcgcgttc   3960
ttgctaatat tgccataaac accattacat gaatcatggt caatatcttt aaaggtagac   4020
caacaattga aacgcctgtt agagagcatt gtcgagcctt ccaagtcaac cattgttgta   4080
tctttctcca cagacaatac acgtttgaac acgtgtctta tgtagaaacg gtctttcaac   4140
gaaggggtta tactgaggtt accatggctg tggatcctag caccgaatag ttcgtcgaac   4200
gtatgaaggc acccagttgc acccaagtgg ggtttgcgat ccacgactat aacaagagag   4260
aaaactccct caaccttagg gggagaaccg tccatgttca tatcaggctg aacacgctca   4320
atcttcaccg ttcccttgaa acgtagacgt ttcaacttaa tgtaggatct actccggttc   4380
ggttgagtct tacctaaact tggataactg ataaacgtag atatggctga attatgggcc   4440
aatacgaaat ctggtccata ttgatgttca cggatccgtt gggcctccac tttgggctca   4500
tcatgggcct tccagacaaa tgaatgatga cgtttcccat taacccgttt aacaattgat   4560
gaacgcttga cagcattata acgtgcatat ggatgtcttt gagtaaagga ggacccacgt   4620
ctatgtctaa tagcatacat attatacagt agagtcaaat agcattagac aatatatata   4680
tgatataaca cagatgactt cactatgtca tccaacttga ataaaacgga tctttaaaca   4740
ccattatata gacgaccttc ctagacacat atcttaagta gactcatcgt tatggcttat   4800
aaatatccac gtctttcgtt agtcaataca cgattgtaaa cgacacacgt acccagtcaa   4860
```

```
tttctacatt ataatttaac acatagaaag acgtgccact aaatctcagc gcccacacac   4920
agtgggtcat ttattcaaat tttaaattaa agttcaacat ctagaaagac gtgccactaa   4980
atttcagggt catcatacaa agtgccacgt atttcaatga aggtaccacg aaagtgggct   5040
attaagtgcg aaacagctgt cacgataaaa agagaaaaag agggcggggt catttttac    5100
agggccgggt cgggtaaaaa atcgcgcggc catccggtaa tattataaac ggatggccgc   5160
cacgtgtctc caagcgctat ctgaggtttt agtataaatt gtactccaat actccaattg   5220
attcaccaag tttgagagga gctcgagctc aattggagta cacccattaa ttacaaatat   5280
gccactacca agaagttctc tcactacaac tcgggaatga acactcattg tttagattaa   5340
acacaaatat ttataaatag acatatgcat atctatacca gacacgcaat tcttcttaaa   5400
aaagctcttc attagctgcc ttatcatctc ttccgcatag ataattttct gtaagggtgc   5460
cgctgcgcgg acttattttt aatatatgga ttctcagtta gttaatcctc ctaacgcatt   5520
caattacata gagtctcacc gagacgagta tcagctttct catgacttaa ctgagataat   5580
aatgcaattc ccgtcgacgg catcacagtt aacagctaga cttagccgga gctgcatgaa   5640
gatcgaccat tgcgtcatag aatacaggca acaggttccg attaacgcca cgggttcagt   5700
gatagtggag atccacgaca aaagaatgac agacaacgaa tctctacaat catcatggac   5760
tttcccaatc agatgcaaca tagatctcca ttatttctcg gcttcgtttt tctcattgaa   5820
ggacccgatt ccatggaaac tgtattacag agtttgtgat acaaatgtgc accagagaac   5880
tcacttcgcg aagttcaaag ggaaactgaa gctctcgacg gcgaaacact cagtggatat   5940
ccccttccgg gcaccaacgg taaagatatt atccaaacag ttcactgata aagatgtgga   6000
cttttcacat gtcgactatg ggaaatggga acggaagccc atcagatgcg catccatgtc   6060
gagacttggg cttagaggcc caattgaaat aaggccaggt gaatcatggg cttctagaag   6120
tacattgggt aatgggcttt cagatgcaga ctccgaagag cagaacgaga tacatcccata  6180
caggcaccta aacagactag gaacaacaat attagacaca ggagagtctg catcagttgt   6240
aggagcacag aaagcggatt ccaacatcac aatgacaatg ggccaattaa acgaattagt   6300
taggactacg gtacacgagt gtataaacag taattgtaag gcttcacagc ccaagtcatt   6360
aaaataaata tcattattgg ttatttcatt aatagattat tcaatatatg gaatacatat   6420
taaattttat tactcatcca acataatcta gatcaaatga tacaaatgta gatgccttag   6480
atatcgtatc tgacatccaa caataataaa ctaacagcgc gttcttgcta atattgccat   6540
aaacaccatt acatgaatca tggtcaatat ctttaaaggt agaccaacaa ttgaaacgcc   6600
tgttagagag cattgtcgag ccttccaagt caaccattgt tgtatctttc tccacagaca   6660
atacacgttt gaacacgtgt cttatgtaga aacggtcttt caacgaaggg gttatactga   6720
ggttaccatg gctgtggatc ctagcaccga atagttcgtc gaacgtatga aggcacccag   6780
ttgcacccaa gtggggtttg cgatccacga ctataacaag agagaaaact ccctcaacct   6840
tagggggaga accgtccatg ttcatatcag gctgaacacg ctcaatcttc accgttccct   6900
tgaaacgtag acgtttcaac ttaatgtagg atctactccg gttcggttga gtcttaccta   6960
aacttggata actgataaac gtagatatgg ctgaattatg ggccaatacg aaatctggtc   7020
catattgatg ttcacggatc cgttgggcct ccactttggg ctcatcatgg gccttccaga   7080
caaatgaatg atgacgtttc ccattaaccc gtttaacaat tgatgaacgc ttgacagcat   7140
tataacgtgc atatggatgt ctttgagtaa aggaggaccc acgtctatgt ctaatagcat   7200
```

```
acatattata cagtagagtc aaatagcatt agacaatata tatatgatat aacacagatg   7260

acttcactat gtcatccaac ttgaataaaa cggatcttta aacaccatta tatagacgac   7320

cttcctagac acatatctta agtagactca tcgttatggc ttataaatat ccacgtcttt   7380

cgttagtcaa tacacgattg taaacgacac acgtacccag tcaatttcta cattataatt   7440

taacacatag aaagacgtgc cactaaatct cagcgcccac acacagtggg tcatttattc   7500

aaattttaaa ttaaagttca acatctagaa agacgtgcca ctaaatttca gggtcatcat   7560

acaaagtgcc acgtatttca atgaaggtac cacgaaagtg ggctattaag tgcgaaacag   7620

ctgtcacgat aaaaagagaa aaagagggcg gggtcatttt ttacagggcc gggtcgggta   7680

aaaaatcgcg cggccatccg gtaatattat aaacggatgg ccgccacgtg tctccaagcg   7740

ctatctgagg ttttagtata aattgtactc caatactcca attgattcac caagtttgag   7800

aggagctc                                                            7808


<210> SEQ ID NO 12
<211> LENGTH: 103
<212> TYPE: RNA
<213> ORGANISM: artificial sequence
<220> FEATURE:
<223> OTHER INFORMATION: synthetic construct

<400> SEQUENCE: 12

gagaggccug ugggcauuca gucuggaucg cgaaaacugu ggaauugauc agcguuggug     60

ggaaagcgcg uuacaagaaa gccgggcaau ugcugugcca ggc                      103


<210> SEQ ID NO 13
<211> LENGTH: 122
<212> TYPE: RNA
<213> ORGANISM: artificial sequence
<220> FEATURE:
<223> OTHER INFORMATION: synthetic construct

<400> SEQUENCE: 13

gagggugoga aggcuuucga gccuggucuu cuugcuaaag cuaacagagg aauacuuuau     60

gucgaugagg uuaaucuuuu ggaugaccau uuaguagaug uucuuuugga uucugcagca    120

uc                                                                   122


<210> SEQ ID NO 14
<211> LENGTH: 22
<212> TYPE: RNA
<213> ORGANISM: artificial sequence
<220> FEATURE:
<223> OTHER INFORMATION: synthetic construct

<400> SEQUENCE: 14

uugaaguugg cuuugaugcc gu                                              22


<210> SEQ ID NO 15
<211> LENGTH: 121
<212> TYPE: RNA
<213> ORGANISM: artificial sequence
<220> FEATURE:
<223> OTHER INFORMATION: synthetic construct

<400> SEQUENCE: 15

ggacacaagc uggaguacaa cuacaacucc cacaacguau acaucacggc cgacaagcag     60

aagaacggca ucaaggcuaa cuucaagauc aggcacaaca ucgaagaugg aagcgugcaa    120

c                                                                    121
```

<210> SEQ ID NO 16
<211> LENGTH: 76
<212> TYPE: RNA
<213> ORGANISM: artificial sequence
<220> FEATURE:
<223> OTHER INFORMATION: synthetic construct

<400> SEQUENCE: 16
gaggguguga aggcuuucga gccuggucuu cuugcuaaag cuaacagagg aauacuuuau 60
gucgaugagg uuaauc 76

<210> SEQ ID NO 17
<211> LENGTH: 22
<212> TYPE: RNA
<213> ORGANISM: artificial sequence
<220> FEATURE:
<223> OTHER INFORMATION: synthetic construct

<400> SEQUENCE: 17
ucugcaucuc ucacggucce ca 22

<210> SEQ ID NO 18
<211> LENGTH: 122
<212> TYPE: RNA
<213> ORGANISM: artificial sequence
<220> FEATURE:
<223> OTHER INFORMATION: synthetic construct

<400> SEQUENCE: 18
guguucucuc caaaugaaau gaacuucccuu auauagagga agggucuugc gaaggauagu 60
gggauugugc gucaucccuu acgucagugg agauaucaca ucaauccacu ugcuuugaag 120
ac 122

<210> SEQ ID NO 19
<211> LENGTH: 127
<212> TYPE: RNA
<213> ORGANISM: artificial sequence
<220> FEATURE:
<223> OTHER INFORMATION: synthetic construct

<400> SEQUENCE: 19
gugguuggaa cgucuucuuu uuccacgaug cuccucgugg gugggggucc aucuuuggga 60
ccacugucgg cagaggcauc uucaacgaug gccuuuccuu uaucgcaaug auggcauuug 120
uaggagc 127

<210> SEQ ID NO 20
<211> LENGTH: 125
<212> TYPE: RNA
<213> ORGANISM: artificial sequence
<220> FEATURE:
<223> OTHER INFORMATION: synthetic construct

<400> SEQUENCE: 20
gagccaccuu ccuuuuccac uaucuucaca auaaagugac agauagcugg gcaauggaau 60
ccgaggaggu uuccggauau uacccuuugu ugaaaagucu caauugcccu uuggucuucu 120
gagac 125

<210> SEQ ID NO 21
<211> LENGTH: 298
<212> TYPE: RNA

```
<213> ORGANISM: artificial sequence
<220> FEATURE:
<223> OTHER INFORMATION: synthetic construct

<400> SEQUENCE: 21

gcgcucaucu uuuugaucug gucaagguuu uccagacaaa aagucuugaa guugaaugcu      60

accagauucu gaucuuaaca ucaccaucua auucaacaag aauugggaca acuccaguga     120

aaaguucuuc uccuuuacug aauucggccg aggauaauga uaggagaagu gaaaagauga     180

gaaagagaaa aagauuaguc uucauuguua uaucuccuug gauuccucaa acucaagguc     240

uuugccuugu gucaacaaag caacaaugcu uuccuuagug agcuuaaccu uagacauc       298


<210> SEQ ID NO 22
<211> LENGTH: 298
<212> TYPE: RNA
<213> ORGANISM: artificial sequence
<220> FEATURE:
<223> OTHER INFORMATION: synthetic construct

<400> SEQUENCE: 22

guaacaucac caucuaauuc aacaagaauu gggacaacuc cagugaaaag uucuucuccu      60

uuacugaauu cggcccgcuc aucuuuuuga ucuggucaag guuuuccaga caaaaagucu     120

ugaaguugaa ugcuaccaga uucugaucuu ccucaaacuc aaggucuuug ccuuguguca     180

acaaagcaac aaugcuuucc uuagugagcu uaaccuuaga caugaggaua augauaggag     240

aagugaaaag augagaaaga gaaaaagauu agucuucauu guuauaucuc cuuggauc       298


<210> SEQ ID NO 23
<211> LENGTH: 141
<212> TYPE: RNA
<213> ORGANISM: artificial sequence
<220> FEATURE:
<223> OTHER INFORMATION: synthetic construct

<400> SEQUENCE: 23

gaucuaauuc aacaagaauu gggacaacuc cagugaaaag uucuucuccu uuacugaauu      60

cggccgagga uaaugauagg agaagugaaa agaugagaaa gagaaaaaga uuagucuuca     120

uuguuauauc uccuuggauc c                                               141


<210> SEQ ID NO 24
<211> LENGTH: 258
<212> TYPE: RNA
<213> ORGANISM: artificial sequence
<220> FEATURE:
<223> OTHER INFORMATION: synthetic construct

<400> SEQUENCE: 24

uuccuguuca aagcugaugc uagaggugac agaaaucaua ugcaagaacg ucaaggccau      60

ucauuuuggu ucaacagauu gaugaaaaau cuaagagccu uugaucuuga gaaguaggua     120

accauuaauu uguguugaag guuugcuacg aaaauaaaaa ggaugucacg ugccaucaag     180

uuauagcuac acgugauuac uaucuaccau ucuccuuuag gguucucgua uaaauacucu     240

acaaucccca ugcaaacc                                                   258


<210> SEQ ID NO 25
<211> LENGTH: 76
<212> TYPE: RNA
<213> ORGANISM: artificial sequence
<220> FEATURE:
<223> OTHER INFORMATION: synthetic construct
```

<400> SEQUENCE: 25
guuuuagagc uagaaauagc aaguuaaaau aaggcuaguc cguuaucaac uugaaaaagu 60
ggcaccgagu cggugc 76

<210> SEQ ID NO 26
<211> LENGTH: 44
<212> TYPE: DNA
<213> ORGANISM: artificial sequence
<220> FEATURE:
<223> OTHER INFORMATION: synthetic construct

<400> SEQUENCE: 26
ggtcaagtgg ccaggagaat gattggtacc gatgcatttc agga 44

<210> SEQ ID NO 27
<211> LENGTH: 45
<212> TYPE: DNA
<213> ORGANISM: artificial sequence
<220> FEATURE:
<223> OTHER INFORMATION: synthetic construct

<400> SEQUENCE: 27
cacttgggaa tggttgtaca actcgaggat cgattctata aggct 45

<210> SEQ ID NO 28
<211> LENGTH: 45
<212> TYPE: DNA
<213> ORGANISM: artificial sequence
<220> FEATURE:
<223> OTHER INFORMATION: synthetic construct

<400> SEQUENCE: 28
gttctaccta tgattcctac cggaggggct ttcaaagacg tcatc 45

<210> SEQ ID NO 29
<211> LENGTH: 127
<212> TYPE: RNA
<213> ORGANISM: artificial sequence
<220> FEATURE:
<223> OTHER INFORMATION: synthetic construct

<400> SEQUENCE: 29
gugguuggaa cgucuucuuu uuccacgaug cuccucgugg gugggggucc aucuuuggga 60
ccacugucgg cagaggcauc uucaacgaug gccuuuccuu uaucgcaaug auggcauuug 120
uaggagc 127

<210> SEQ ID NO 30
<211> LENGTH: 311
<212> TYPE: RNA
<213> ORGANISM: artificial sequence
<220> FEATURE:
<223> OTHER INFORMATION: synthetic construct

<400> SEQUENCE: 30
gaggaagggu cuugcgaagg auagugggau ugugcgucau cccuuacguc aguggagaua 60
ucacaucaau ccacuugcuu ugaagacgug guuggaacgu cuucuuuuuc cacgaugcuc 120
cucgugggug ggggguccauc uuugggacca cugucggcag aggcaucuuc aacgauggcc 180
uuuccuuuau cgcaaugaug gcauuuguag gagccaccuu ccuuuuccac uaucuucaca 240 auaaaagugac agauagcugg gcaauggaau ccgaggaggu uuccggauau uacccuuugu 300

-continued

```
ugaaaagucu c                                                        311


<210> SEQ ID NO 31
<211> LENGTH: 36
<212> TYPE: RNA
<213> ORGANISM: artificial sequence
<220> FEATURE:
<223> OTHER INFORMATION: synthetic construct

<400> SEQUENCE: 31

ucuccuauca uuauccucgg guuuuagagc uaugcu                             36


<210> SEQ ID NO 32
<211> LENGTH: 67
<212> TYPE: RNA
<213> ORGANISM: artificial sequence
<220> FEATURE:
<223> OTHER INFORMATION: synthetic construct

<400> SEQUENCE: 32

agcauagcaa guuaaaauaa ggcuaguccg uuaucaacuu gaaaaagugg caccgagucg    60

gugcuuu                                                             67
```

METHODS AND COMPOSITIONS FOR INTRODUCING NUCLEIC ACIDS INTO PLANTS

CROSS-REFERENCE TO RELATED APPLICATIONS AND INCORPORATION OF SEQUENCE LISTINGS

This application is a U.S. National Stage of International Application No. PCT/US2016/035500, filed Jun. 2, 2016, which claims priority to U.S. Provisional Application No. 62/170,447, filed Jun. 3, 2015, both of which are incorporated by reference in their entirety herein. A sequence listing contained in the file named "P34448US01_SEQ.txt" which is 41,888 bytes in size (measured in MS-Windows®) and created on Dec. 1, 2017, is filed electronically herewith and incorporated by reference in its entirety.

FIELD

Disclosed herein are methods and compositions for introducing nucleic acids into plants. More specifically, disclosed herein are methods and compositions for introducing a nucleic acid, such as a double-stranded RNA, for silencing a target gene in a plant. Also disclosed herein are plants exhibiting modification of a target gene, obtained through the use of such methods and compositions.

BACKGROUND

There is a need for introducing nucleic acids, such as DNA or RNA for silencing a target gene, into plants, where the methods are scalable so as to be practical for use in multiple plants, such as plants in a greenhouse or growing in a field. Most methods of introducing a nucleic acid for gene suppression are cumbersome and therefore generally of practical use only on individual plants in the laboratory or other small-scale environments. For example, "gene gun" or "biolistic" methods use gold or tungsten particles typically of 0.5 to 2 micrometers in size and coated with DNA or RNA that has been precipitated onto the particles; the particles are discharged using a "gene gun" powered by a gas at high pressure (typically hundreds to thousands pounds per square inch) onto a plant held in an evacuated chamber. More recent biolistic methods using equipment such as the Helios® gene gun (Bio-Rad Laboratories, Inc.) use lower pressures (in the hundreds pounds per square inch) but still require the use of helium gas as a propellant and use of gold or tungsten particles typically of 0.5 to less than 2 micrometers in size that must be pre-coated with a nucleic acid; furthermore, each plant must be treated individually and individual "cartridges" containing the particles must be prepared for each treatment. These limitations make the gene gun approaches inconvenient for true scalability for treating large numbers of plants such as in greenhouse and field use.

The present disclosure is related to various methods and compositions for introducing nucleic acids into a plant, where the methods are scalable and adaptable for use in multiple plants, and even for agricultural use in plants growing in a field.

SUMMARY

Several embodiments are related to a method for silencing a target gene in a plant, including, in any order, the steps of: (a) abrading a surface of a plant with a particulate of a size greater than about 2.5 micrometers; (b) applying an RNA to the surface of the plant, wherein the RNA comprises at least 19 consecutive nucleotides having a sequence that is complementary or identical to the sequence of a target gene in the plant; whereby the target gene is silenced. Several embodiments are also related to a single-step method, wherein a surface of a plant is abraded with a composition including a particulate of a size greater than about 2.5 micrometers and an RNA that includes at least 19 consecutive nucleotides having a sequence that is complementary or identical to the sequence of a target gene in the plant; whereby the target gene is silenced.

Several embodiments are related to a spray apparatus for spraying multiple plants or multiple rows of plants, including a propellant source, at least one spray nozzle, and a reservoir containing a composition including a particulate and a nucleic acid that includes at least 19 consecutive nucleotides having a sequence that is complementary or identical to the sequence of a target gene in the plants. In various embodiments, the nucleic acid is DNA or RNA, single- or double-stranded, or is provided as a synthetic nucleic acid or in a microbial cell or as a microbial fermentation product. In some embodiments, the nucleic acid is an siRNA or a microRNA or a microRNA precursor.

Several embodiments are related to an apparatus for introducing a nucleic acid into a whole plant, including: (a) a matrix supporting an abrasive, and (b) a nucleic acid. In embodiments, the apparatus can be used in single-step methods, e. g., when the nucleic acid is complexed with or otherwise attached or bonded to the abrasive. In some embodiments, the apparatus can be used in multi-step methods, e. g., when the nucleic acid is applied before and/or after the plant or plant part is contacted by the abrasive.

Several embodiments are related to a method for introducing a nucleic acid into a plant, including: (a) applying a composition including a nucleic acid to a surface of a plant, and (b) contacting a matrix supporting an abrasive with the surface; whereby the nucleic acid is introduced into the plant.

Several embodiments are related to a method for introducing a nucleic acid into a whole plant, including: (a) applying a composition including an abrasive and a nucleic acid to a surface of a whole plant, and (b) applying pressure to the surface; whereby the nucleic acid is introduced into the whole plant.

Several embodiments are related to a method for introducing a nucleic acid into a whole plant including, in any order, the steps of: (a) mechanical penetration of a surface of a whole plant with a non-particulate microstructure, and (b) contacting the surface of a whole plant with a nucleic acid. Embodiments include those where the non-particulate microstructure is a matrix on which is supported at least one selected from the group consisting of micro- or nano-needles, -whiskers, -fibers, and -wires. In embodiments, the non-particulate microstructure is removed after penetration of the plant surface, leaving the nucleic acid in the plant.

Several embodiments include a plant or a field of plants treated by a method, composition, or apparatus described herein, wherein the plant exhibits a desirable phenotype (such as improved yield, improved tolerance of biotic or abiotic stress, improved resistance to disease, improved herbicide susceptibility, improved herbicide resistance, and modified nutrient content) resulting from the treatment and when compared to an untreated plant. Several embodiments include progeny seed or propagatable plant part of such plants, and commodity products produced from such plants. Several embodiments include a method for providing a plant exhibiting modification of a target gene in the plant, comprising directly regenerating a plant from a source plant treated by a method, composition, or apparatus described herein, wherein the modification of the target gene is non-heritable silencing of the target gene, or heritable or epigenetic silencing of the target gene, or a change in the nucleotide sequence of the target gene; embodiments include the directly regenerated plant exhibiting modification of the target gene and plants of subsequent generations grown from the directly regenerated plant and exhibiting modification of the target gene. Other aspects and specific embodiments are disclosed in the following detailed description and Examples.

DETAILED DESCRIPTION

Figure 1:
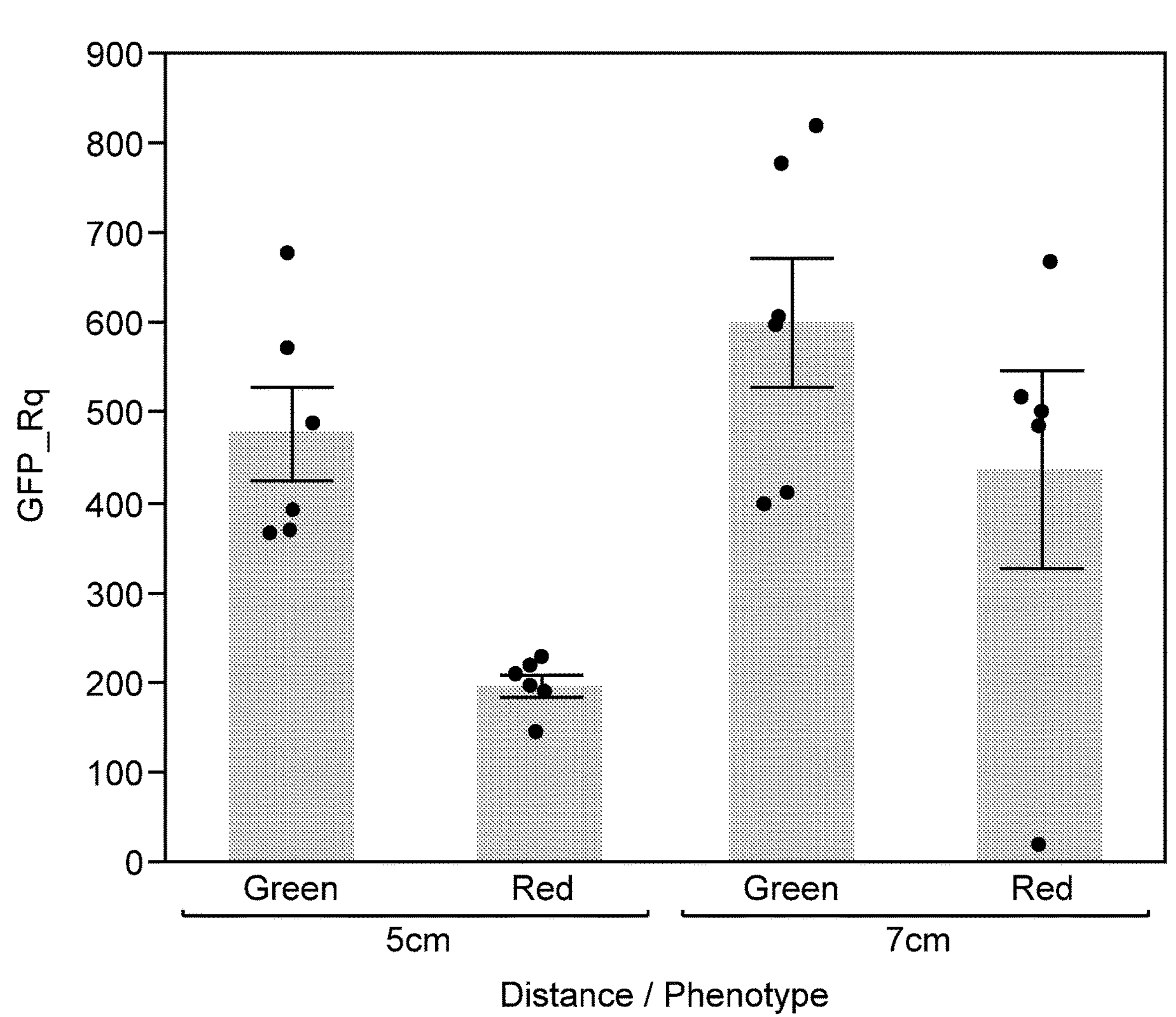
FIG. 1 depicts qPCR measurements of relative abundance of GFP mRNA, correlated to visual phenotype (see Example 7).

Unless defined otherwise, all technical and scientific terms used have the same meaning as commonly understood by one of ordinary skill in the art in the field. Generally, the nomenclature used and the manufacturing or laboratory procedures described below are well known and commonly employed in the art. Conventional methods are used for these procedures, such as those provided in the art and various general references. Where a term is provided in the singular, aspects described by the plural of that term are also contemplated. Where there are discrepancies in terms and definitions used in references that are incorporated by reference, the terms used in this application shall have the definitions given. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" ($6^{th}$ edition, 2002, McGraw-Hill, New York), or the "Oxford Dictionary of Biology" ($6^{th}$ edition, 2008, Oxford University Press, Oxford and New York). No limitation to a mechanism or mode of action is intended by this disclosure. Reference thereto is provided for illustrative purposes only.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotides of the DNA with uracil (U) nucleotides. Thus, providing a specific DNA sequence is understood to define the exact RNA equivalent. A given first polynucleotide sequence, whether DNA or RNA, further defines the sequence of its exact complement (which can be DNA or RNA), i. e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

The term "polynucleotide" commonly refers to a DNA or RNA molecule containing multiple nucleotides and generally refers both to "oligonucleotides" (a polynucleotide molecule of 18-25 nucleotides in length) and longer polynucleotides of 26 or more nucleotides. Polynucleotides also include molecules containing multiple nucleotides including non-canonical nucleotides or chemically modified nucleotides as commonly practiced in the art; see, e. g., chemical modifications disclosed in the technical manual "RNA Interference (RNAi) and DsiRNAs", 2011 (Integrated DNA Technologies Coralville, Iowa). Generally, polynucleotides or triggers described herein, whether DNA or RNA or both, and whether single- or double-stranded, include at least one segment of 18 or more contiguous nucleotides (or, in the case of double-stranded polynucleotides, at least 18 contiguous base-pairs) that are essentially identical or complementary to a fragment of equivalent size of the DNA of a target gene or the target gene's RNA transcript. Throughout this disclosure, "at least 18 contiguous" means "from about 18 to about 10,000, including every whole number point in between". Thus, embodiments include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, such as the dsRNA triggers described in the working Examples, its length can be similarly described in terms of base pairs. Double-stranded polynucleotides, such as the dsRNA triggers described in the working examples, can further be described in terms of one or more of the single-stranded components.

The polynucleotides or triggers described herein are generally designed to suppress or silence one or more genes ("target genes"). The term "gene" refers to any portion of a nucleic acid that provides for expression of a transcript or encodes a transcript. A "gene" can include, but is not limited to, a promoter region, 5' untranslated regions, transcript encoding regions that can include intronic regions, 3' untranslated regions, or combinations of these regions. In embodiments, the target genes can include coding or non-coding sequence or both. In other embodiments, the target gene has a sequence identical to or complementary to a messenger RNA, e. g., in embodiments the target gene is a cDNA.

In embodiments, the target gene is an endogenous gene of the plant or a transgene expressed in the plant. In embodiments the target gene is not expressed by the plant itself but by a pathogen or parasite in or on the plant. In some embodiments, the target gene in the plant is a gene of a parasitic plant, fungus, or bacterium that is a pathogen or parasite of the plant; in other embodiments, the target gene in the plant is a gene of a virus that is a pathogen of the plant. In embodiments, the target gene is multiple target genes; the multiple target genes can be from a single species or can be from more than one species.

In embodiments, the methods, compositions, and apparatuses described herein are useful for obtaining a phenotype (e. g., improved yield, improved resistance temperature, water, or nutrient stress, improved resistance to pathogens, improved herbicide susceptibility, improved herbicide resistance, and modified nutrient content or appearance) in a plant directly treated by a method as described herein. In other embodiments, the effect of treatment by a method of this disclosure is passed on to subsequent generations, for example in an epigenetic effect. In many embodiments the DNA or RNA employed in the methods is designed to silence a target gene. In related applications the methods can be used to deliver any nucleic acid of interest, including nucleic acids designed for gene editing, e. g., using a CRISPR or Cas9 system.

In contrast to plant transformation techniques using a gene gun, the methods and compositions described herein use particulates made of materials less expensive than gold or tungsten and of a size range greater than that of the particles used in gene gun transformation, typically use lower pressures, do not require treatment of the plant in a vacuum, and can be carried out in a whole plant or multiple plants. The methods and compositions are scalable so as to be useful in treating multiple plants at one time.

In general the methods described herein use mechanical disruption of a surface of the plant to assist in delivery of the nucleic acid to the plant, for example by contacting a surface of a plant with an abrasive such as a loose particulate or a particulate supported on a matrix, or by contacting a surface of a plant with a non-particulate microstructure. Generally the abrasion used in the methods superficially disrupts cells in the cuticle or epidermis or both cuticle and epidermis of the plant, but does not damage cells in deeper tissues of the plant.

In embodiments, the target gene silencing resulting from treatment of a surface of the plant is systemic, i. e., the silencing phenotype is observed in parts of the plant other than the treated parts. In embodiments, the target gene silencing resulting from treatment of a surface of the plant is local, i. e., the silencing phenotype is observed in parts treated by the methods and compositions described herein.

The methods described herein can additionally combine mechanical disruption of the plant surface with other treatments, for example with sequential or concomitant use of a surfactant, nuclease inhibitors, photoprotectants, rainfastness agents, and the like.

In embodiments, the methods and compositions described herein are useful for obtaining a phenotype (e. g., improved yield, improved resistance to temperature, water, or nutrient stress, improved resistance to pathogens, improved herbicide susceptibility, improved herbicide resistance, and modified nutrient content or appearance) in a plant directly treated by a methods or composition described herein. In other embodiments, the effect of treatment by a method or composition as described herein is passed on to subsequent generations, for example in an epigenetic effect. In many embodiments the DNA or RNA employed in the methods is designed to silence a target gene. In other applications the methods can be used to deliver any nucleic acid of interest, including nucleic acids designed for gene editing, e. g., using a CRISPR or Cas9 system.

Also described herein are compositions and apparatuses useful in delivering a nucleic acid into a plant, as well as plants treated by a method or composition as described herein. In embodiments, DNA- or RNA-coated aluminum oxide or silicon carbide particles are delivered into a plant using a pressurized gas. For example, RNA molecules (e. g., synthetic dsRNA, or a dsRNA produced in a bacterial system) or DNA molecules (e. g., a VIGS vector or a plasmid) are coated onto aluminum oxide ($Al_2O_3$) or silicon carbide (SiC, "carborundum") particles and allowed to dry; these nucleic-acid-coated particles are sprayed onto leaves of a plant using pressurized air or other gas and cause silencing of the gene targeted by the nucleic acid. An airbrush (e. g., Master Airbrush Model G78 Single-Action Gravity Feed Air Abrasive Etching Airbrush Gun as used in the experiments described herein) using compressed air is one convenient means of applying the particulates to the plant. Pressurized gas can be provided by any convenient means, such as an air compressor or a compressed gas cylinder; when used with a dry powder composition, preferably a low-humidity pressurized gas is used.

Examples of blunt-ended dsRNA triggers designed to silence green fluorescent protein (GFP) are provided in Table 1.

TABLE 1

| SEQ ID NO:* | size (base pairs) |
|---|---|
| 1 | 50 |
| 2 | 78 |
| 3 | 124 |
| 4 | 125 |
| 5 | 249 |
| 6 | 258 |

*sequence of anti-sense strand, 5'→3'

Examples of particulate abrasives useful in the methods and compositions described herein are provided in Table 2.

TABLE 2

| Abrasive | Composition | Median Size (micrometers) |
|---|---|---|
| 280 mesh SiC | silicon carbide | 33.0-36.0 |
| 320 mesh SiC | silicon carbide | 26.3-29.2 |
| 360 mesh SiC | silicon carbide | 20.1-23.1 |
| 400 mesh SiC | silicon carbide | 15.5-17.5 |
| 500 mesh SiC | silicon carbide | 11.3-13.3 |
| 600 mesh SiC | silicon carbide | 8.0-10.0 |
| CELITE 560 | diatomaceous silica | 95.7 |
| CELITE 545 | diatomaceous silica | 46.5 |
| CELITE 503 | diatomaceous silica | 33.9 |
| CELITE 512 | diatomaceous silica | 23.9 |
| CELITE 577 | diatomaceous silica | 20.8 |
| CELITE S | diatomaceous silica | 7.3 |
| glass microsphere | soda lime glass | 10-22 |
| glass microsphere | soda lime glass | 22-27 |
| glass microsphere | soda lime glass | 27-32 |
| glass microsphere | soda lime glass | 32-38 |
| glass microsphere | soda lime glass | 38-45 |
| glass microsphere | soda lime glass | 45-53 |
| glass microsphere | soda lime glass | 53-63 |
| 240 mesh $AlO_3$ | aluminum oxide | >37 |
| 280 mesh $AlO_3$ | aluminum oxide | 33-36 |
| 320 mesh $AlO_3$ | aluminum oxide | <37 |
| 360 mesh $AlO_3$ | aluminum oxide | 20.1-23.1 |
| 400 mesh $AlO_3$ | aluminum oxide | 15.5-17.5 |
| 500 mesh $AlO_3$ | aluminum oxide | 11.3-13.3 |
| 600 mesh $AlO_3$ | aluminum oxide | 8.0-10.0 |
| 800 mesh $AlO_3$ | aluminum oxide | 5.3-.73 |

Methods For Silencing A Target Gene In A Plant Using Abrasives

A first aspect provides a method for silencing a target gene in a plant, including, in any order, the steps of: (a) abrading a surface of a plant with a particulate of a size greater than about 2.5 micrometers; (b) applying an RNA to the surface of the plant, wherein the RNA includes at least 19 consecutive nucleotides having a sequence that is complementary or identical to the sequence of a target gene in the plant; whereby the target gene is silenced.

In embodiments, step (a) is followed by step (b). In other embodiments, step (b) is followed by step (a). In embodiments where the RNA is applied prior to the abrasion step, the RNA can be allowed to dry on the plant surface prior to abrasion. Additional treatments of the plant (for example, treatment with a surfactant, an RNase inhibitor, a photoprotectant, or a rainfastness agent) are optionally performed, subsequent to either abrasion or application of RNA, or concomitant with either or both steps.

The RNA applied to the plant surface can be single-stranded RNA (ssRNA), double-stranded RNA (dsRNA), or a combination of ssRNA and dsRNA. "Double-stranded" refers to the base-pairing that occurs between sufficiently complementary, anti-parallel nucleic acid strands to form a double-stranded or duplexed nucleic acid structure, generally under physiologically relevant conditions. In embodiments, the RNA is a dsRNA including two strands that are perfectly complementary and form a blunt-ended RNA duplex. In other embodiments, RNA is a dsRNA that is not perfectly complementary, for example, a dsRNA that has additional nucleotides at one or both ends so as to form an overhang, or a dsRNA that includes non-base-paired mismatches within the otherwise base-paired duplex. In embodiments, the dsRNA has an overhang at one or both ends (termini); the overhang can be a single nucleotide or 2, 3, 4, 5, 6, or more nucleotides, and can be located on the 5' end or on the 3' end of a strand. The RNA can be provided as a single nucleotide sequence (as a single molecule) or multiple nucleotide sequences (as multiple molecules, or as multiple strands of RNA). The RNA can be chemically synthesized, or can be produced by expression in a microorganism, by expression in a plant cell, or by microbial fermentation. The RNA can be chemically modified, e. g., to improve stability or efficacy.

The RNA includes at least 19 consecutive nucleotides having a sequence that is complementary or identical to the sequence of a target gene in the plant. The RNA can further include nucleotides having a sequence unrelated to the sequence of the target gene or genes to be suppressed; for example, the RNA can include flanking or intervening "filler" or "spacer" segments of consecutive nucleotides, wherein the segments have a sequence unrelated to the sequence of the target gene or genes to be suppressed. In embodiments, the RNA includes 19-500 nucleotides (or base pairs, where the RNA is dsRNA). In embodiments, the RNA includes 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides (or base pairs). For reasons of economy, the RNA can be relatively short, of about 300 nucleotides or base pairs in length. Nonetheless, in embodiments, the RNA has a length greater than about 300 nucleotides (or base pairs), e. g., between about 300 to about 400, between about 400 to about 500, between about 500 to about 600, between about 600 to about 700, between about 700 to about 800, between about 800 to about 900, between about 900 to about 1000, between about 300 to about 500, between about 300 to about 600, between about 300 to about 700, between about 300 to about 800, between about 300 to about 900, or about 1000 nucleotides (or base pairs) in length, or even greater than about 1000 nucleotides (or base pairs) in length, for example up to the entire length of a target gene or genes including coding or non-coding or both coding and non-coding portions of the target gene or genes).

In embodiments, the RNA is ssRNA or dsRNA designed to silence a single target gene. In embodiments, the RNA is ssRNA or dsRNA including multiple repeating segments for targeting a single target gene. Multiple target genes (which can be target genes of the plant, or of a pathogen or parasite of the plant, or a combination of both), or multiple regions of a single target gene, can be targeted by a chimeric RNA. In an example, the RNA is a dsRNA including segments corresponding to different regions of the target gene, or multiple copies of a segment. In an example, the RNA is a chimeric dsRNA including dsRNA segments targeting a gene expressed in the plant and dsRNA segments targeting a gene of a pathogen or parasite of the plant.

In embodiments, the RNA includes a miRNA precursor or a small RNA such as an siRNA or a mature miRNA known to have gene silencing functionality in a cell. In embodiments, the RNA is a 21-mer or 22-mer. The RNA is non-transcribable, and is not self-replicating. In embodiments, the RNA is not contained in a viral vector nor encoded by a plasmid.

In embodiments of the method, the RNA is in a solution, e. g., a sprayable solution. Alternatively, the RNA can be provided in a powder, emulsion, or suspension. Solution, powders, emulsions, or suspensions can conveniently further include one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. Specific embodiments include an RNA solution (or powder, emulsion, or suspension) including one or more components selected from the group consisting of sucrose, mannitol, 2-(N-morpholino)ethanesulfonic acid, and Silwet L77.

In embodiments, the abrasion step includes application of the particulate in a spray. Embodiments include those wherein the spray is applied by an airbrush, by a compressed-gas sprayer, or by a canister sprayer, a track sprayer, or a boom sprayer.

The abrasion step can be accomplished by means other than by spraying. In embodiments, the particulate is supported by, attached to, or embedded in a matrix. The matrix can include a fibrous, porous, non-porous, or adhesive support. An example is a particulate abrasive that is permanently bonded to paper, such as sandpaper.

Particulates useful in the methods include a particulate abrasive selected from the group consisting of a mineral abrasive, a metal abrasive, a synthetic abrasive, and an organic abrasive. Embodiments include particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell particles.

Particulate size is selected according to factors such as compatibility with a given formulation, suitability for use in a given apparatus (such as a spray nozzle), efficiency in delivering the RNA, or for minimizing damage to the treated plants. In embodiments, the particulate is of an average size range from about 2.5 micrometers to about 50 micrometers. In various embodiments, the particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers. The working Examples further illustrate embodiments of useful particulate size ranges.

In embodiments of the method, the particulate, the RNA, or both, are further applied with at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the particulate, the RNA, or both, are further applied with at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the particulate, the RNA, or both, are further applied with at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the particulate, the RNA, or both, are further applied with at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myo-inositol (inositol). Alternatively, any of these additional components or combinations thereof can be applied separately from the application of the particulate or of the RNA.

The abrasion used in these two-step methods preferably does minimal damage to the plant. In embodiments, the particulate disrupts cells only in the cuticle, or only in the cuticle and epidermis of the plant. In embodiments, cells deeper than the epidermis are essentially not damaged by the particulate abrasive. In embodiments, the silencing is systemic and the target gene is silenced in at least one location of the plant that is not the location of abrasion.

In embodiments, these methods are useful for obtaining a phenotype (e. g., improved yield, improved resistance temperature, water, or nutrient stress, improved resistance to pathogens, improved herbicide susceptibility, improved herbicide resistance, and modified nutrient content or appearance) resulting from silencing of a target gene in a plant directly treated by these methods. In a related method, the effect of treatment is passed on to subsequent generations, for example where the RNA is designed to target non-coding sequence such as 5' untranslated sequence or a promoter of the target gene, and thereby causing an epigenetic effect. For example, use of a silencing RNA targeting the promoter region of an endogenous phytoene desaturase (PDS) gene in a plant results in bleaching not only of the treated plant but in progeny plants that have not themselves been treated directly with the silencing RNA.

In many embodiments the RNA employed in the methods is designed to silence a target gene. However, in related applications similar methods can be used to deliver any nucleic acid of interest, including nucleic acids designed for gene editing, e. g., using a CRISPR or Cas9 system. In one aspect, a polynucleotide provided herein comprises a nucleic acid sequence encoding one or more elements of a NgAgo-gDNA system. In some embodiments, the polynucleotide encodes a prokaryotic Argonaute. In some embodiments, the polynucleotide encodes a guide sequence used by a prokaryotic Argonaute. In some embodiments, the prokaryotic Argonaute is from *Natronobacterium gregoryi* (NgAgo), *Thermus thermophiles* (TtAgo), or *Pyrococcus furiosus* (PfAgo). See, e.g., Gao et al., Nat. Biotechnol., May 2, 2016, published online; Swarts et al., Nature, 2014, 507(7491): 258-61; and Swarts et al., Nucleic Acid Res., 2015, 43(10): 5120-5129. Similar to Cas9, endonucleases from the Argonaute protein family also use oligonucleotides as guides to degrade invasive genomes. For example, the *Natronobacterium gregoryi* Argonaute (NgAgo) was found to be a DNA-guided endonuclease suitable for genome editing. NgAgo binds 5' phosphorylated single-stranded guide DNA (gDNA) of about 24 nucleotides, efficiently creates site-specific DNA double-strand breaks when loaded with the gDNA. The NgAgo-gDNA system does not require a protospacer-adjacent motif (PAM), as does Cas9, and it has been suggested that it has a low tolerance to guide-target mismatches and high efficiency in editing (G+C)-rich genomic targets. Gao et al., Nat. Biotechnol., May 2, 2016.

SINGLE-STEP METHODS FOR SILENCING A TARGET GENE IN A PLANT USING ABRASIVES

Another aspect provides a single-step method for silencing a target gene in a plant, including: abrading a surface of a plant with a composition including a particulate of a size greater than about 2.5 micrometers and an RNA that includes at least 19 consecutive nucleotides having a sequence that is complementary or identical to the sequence of a target gene in the plant; whereby the target gene is silenced.

In embodiments, the composition is a solid or a dry composition, such as a powder. In embodiments, the composition is a suspension of the particulate and the RNA in a liquid or a gel. In embodiments, the composition is an emulsion. In embodiments the RNA is physically closely associated with or in contact with the particulate, e. g., simply by drying the RNA onto the particulate, or by bonding the RNA to the particulate by ionic or electrostatic attraction, direct covalent bonding, covalent bonding using a linker, or by means of an adhesive or other affixing agent.

The composition is applied to the plant using any convenient application method, which may involve the use of positive or negative pressure to achieve abrasion of the plant surface. Dry compositions, such as powders, can be applied by dusting or dry spraying. Liquids, including suspensions or emulsions, can be applied with a brush, roller, sprayer, or other apparatus. In embodiments, the abrasion is achieved by applying the composition by spraying, e. g., by application using an airbrush, by a compressed-gas sprayer, or by a canister sprayer, a track sprayer, or a boom sprayer.

In embodiments, the composition includes "loose" (non-affixed) or discrete particulates, e. g., a loose powder or dust. An embodiment includes a composition where a loose particulate abrasive is mixed with a solution of RNA and the mixture dried to form a dry powder which is then applied in a single step to a plant. In other embodiments, the composition includes a particulate supported by, attached to, or embedded in a matrix, such as a fibrous, porous, non-porous, or adhesive support. An embodiment includes a composition where a loose particulate abrasive is mixed with a solution of RNA, the resulting mixture is affixed to a matrix, and the matrix including the particulate and RNA is then applied to a plant. Another embodiment includes a composition where the RNA is added to a particulate already affixed to a matrix and the whole then applied to a plant; an example is sandpaper or other particulate-abrasive-bearing material to which RNA is added.

In embodiments, the composition includes a particulate selected from the group consisting of a mineral abrasive, a metal abrasive, a synthetic abrasive, and an organic abrasive. In embodiments, the composition includes particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell par In embodiments, the particulate used in the composition is of an average size range from about 2.5 micrometers to about 50 micrometers. In various embodiments, the particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers, as further illustrated in the working Examples.

In embodiments, the composition further includes one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. Specific embodiments of the composition include one or more components selected from the group consisting of sucrose, mannitol, 2-(N-morpholino)ethanesulfonic acid, and Silwet L77.

In embodiments, the composition further includes at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the composition further includes at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the composition further includes at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myo-inositol (inositol). Alternatively, any of these additional components or combinations thereof can be applied separately from the particulate-RNA composition. Thus, additional treatments of the plant (for example, treatment with a surfactant, an RNase inhibitor, a photoprotectant, or a rainfastness agent) are optionally performed, subsequent to or following application of the particulate-RNA composition.

The abrasion used in these single-step methods preferably does minimal damage to the plant. In embodiments, the particulate disrupts cells only in the cuticle, or only in the cuticle and epidermis of the plant. In embodiments, cells deeper than the epidermis are essentially not damaged by the particulate abrasive. In embodiments, the silencing is systemic and the target gene is silenced in at least one location of the plant that is not the location of abrasion.

Other details of the single-step method are similar to those described above for the two-step method for silencing a target gene in a plant, as described above under the heading "METHODS FOR SILENCING A TARGET GENE IN A PLANT USING ABRASIVES".

In embodiments, these methods are useful for obtaining a phenotype (e. g., improved yield, improved resistance temperature, water, or nutrient stress, improved resistance to pathogens, improved herbicide susceptibility, improved herbicide resistance, and modified nutrient content or appearance) resulting from silencing of a target gene in a plant directly treated by these methods. In a related method, the effect of treatment is passed on to subsequent generations, for example where the RNA is designed to target non-coding sequence such as 5' untranslated sequence or a promoter of the target gene, and thereby causing an epigenetic effect. For example, use of a silencing RNA targeting the promoter region of an endogenous phytoene desaturase (PDS) gene in a plant results in bleaching not only of the treated plant but in progeny plants that have not themselves been treated directly with the silencing RNA.

In many embodiments the RNA employed in the methods is designed to silence a target gene. However, in related applications similar methods can be used to deliver any nucleic acid of interest, including nucleic acids designed for gene editing, e. g., using a CRISPR or Cas9 system.

A Spray Apparatus For Applying A Composition For Silencing A Target Gene In A Plant Another aspect provides a spray apparatus for spraying multiple plants or multiple rows of plants, including a propellant source, at least one spray nozzle, and a reservoir containing a composition including a particulate and a nucleic acid that includes at least 19 consecutive nucleotides having a sequence that is complementary or identical to the sequence of a target gene in the plants. Generally, spraying by means of the spray apparatus results in abrading of the plants by the particulate and delivery of the nucleic acid to the plant.

In embodiments of the spray apparatus, the propellant includes a compressed gas, such as compressed air or nitrogen or other inert gas. In other embodiments, the propellant includes a compressed liquid. Embodiments of the spray apparatus include a canister sprayer, a track sprayer, or a boom sprayer. In embodiments, the spray apparatus is mounted on a vehicle or on other mechanical device to enable movement of the sprayer over the plants or rows of plants.

In embodiments of the spray apparatus, the nucleic acid is DNA or RNA or a mixture of both. In embodiments, the nucleic acid is synthetic. In embodiments, the nucleic acid is provided in a microbial cell or as a microbial fermentation product. Embodiments of the spray apparatus include those where the nucleic acid is single-stranded DNA or double-stranded DNA. Embodiments include those wherein the DNA includes coding sequence of the target gene, non-coding sequence of the target gene, or both. Embodiments include those wherein the DNA is contained in a plasmid, or in a viral vector. In embodiments, the DNA is non-transcribable, and is not self-replicating. Embodiments of the spray apparatus include those where the nucleic acid is RNA. Embodiments include those wherein the RNA includes single-stranded RNA (ssRNA), double-stranded RNA (dsRNA), or a combination of ssRNA and dsRNA. Other details relevant to nucleic acids of use in the spray apparatus are similar to those described above for the two-step method for silencing a target gene in a plant, as described above under the heading "Methods For Silencing A Target Gene In A PlantUSING ABRASIVES".

Embodiments of the spray apparatus include those where the composition further includes one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. Specific embodiments of the composition include one or more components selected from the group consisting of sucrose, mannitol, 2-(N-morpholino)ethanesulfonic acid, and Silwet L77.

Embodiments of the spray apparatus include those where the composition further includes at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the composition further includes at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the composition further includes at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myo-inositol (inositol). Alternatively, any of these additional components or combinations thereof can be applied separately from the particulate-RNA composition; in such instances the spray apparatus can include one or more additional reservoirs containing such components.

Embodiments of the spray apparatus include those where the composition includes a particulate selected from the group consisting of a mineral abrasive, a metal abrasive, a synthetic abrasive, and an organic abrasive. In embodiments, the composition includes particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell par In embodiments, the particulate used in the composition is of an average size range from about 2.5 micrometers to about 50 micrometers. In various embodiments, the particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers, as further illustrated in the working Examples.

The abrasion achieved by use of the spray apparatus preferably does minimal damage to the plant. In embodiments, use of the spray apparatus results in disruption of cells only in the cuticle, or only in the cuticle and epidermis of the plant. In embodiments, cells deeper than the epidermis are essentially not damaged by the particulate abrasive. In embodiments, use of the spray apparatus results in systemic silencing, wherein the target gene is silenced in at least one location of the plant that is not the location of abrasion.

Other details relevant to the spray apparatus or to its use are similar to those described above for the two-step method for silencing a target gene in a plant, as described above under the heading "Methods For Silencing A Target Gene In A Plant Using Abrasives".

An Apparatus For Introducing A Nucleic Acid Into A Whole Plant

Another aspect provides an apparatus for introducing a nucleic acid into a whole plant, including: (a) a matrix supporting an abrasive, and (b) a nucleic acid.

In embodiments of the apparatus, the matrix and abrasive are permanently bonded to each other. In other embodiments, the matrix and abrasive are not permanently bonded to each other. Embodiments include those wherein the matrix includes a fibrous, porous, non-porous, or adhesive support, and the abrasive includes discrete particles. In embodiments, the matrix includes cotton fiber or other natural fiber. In embodiments, the matrix supporting an abrasive is sandpaper or other solid material incorporating a particulate abrasive permanently bonded to the matrix. In embodiments, the nucleic acid is carried by or affixed to a particulate abrasive. An example of the apparatus includes a matrix including the particulate and RNA, prepared by mixing a loose particulate abrasive with a solution of RNA, drying the resulting mixture, and affixing the dried mixture to a matrix such as a fibrous, porous, non-porous, or adhesive matrix. Another embodiment of the apparatus includes a particulate already affixed to a matrix, to which the RNA is added and the whole then applied to a plant; an example is sandpaper or other particulate-abrasive-bearing material to which RNA is added.

In embodiments of the apparatus, the nucleic acid is DNA or RNA or a mixture of both. In embodiments, the nucleic acid is synthetic. In embodiments the nucleic acid includes at least 19 consecutive nucleotides having a sequence that is complementary or identical to the sequence of a target gene in the plant. In embodiments the nucleic acid includes at least 19 consecutive nucleotides having a sequence that is complementary or identical to the sequence of a target gene of a pathogen or parasite of the plant. In embodiments, the nucleic acid is provided in a microbial cell or as a microbial fermentation product. Embodiments of the apparatus include those where the nucleic acid is single-stranded DNA or double-stranded DNA. Embodiments include those wherein the DNA includes coding sequence of the target gene, non-coding sequence of the target gene, or both. Embodiments include those wherein the DNA is contained in a plasmid, or in a viral vector. In embodiments, the DNA is non-transcribable, and is not self-replicating. Embodiments of the apparatus include those where the nucleic acid is RNA. Embodiments include those wherein the RNA includes single-stranded RNA (ssRNA), double-stranded RNA (dsRNA), or a combination of ssRNA and dsRNA. Other details relevant to RNAs of use in the apparatus are similar to those described above for RNAs used in the two-step method for silencing a target gene in a plant, as described above under the heading "Methods For Silencing A Target Gene In A Plant Using Abrasives".

Embodiments of the apparatus include those where the apparatus further includes one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. Specific embodiments of the apparatus include one or more components selected from the group consisting of sucrose, mannitol, 2-(N-morpholino)ethanesulfonic acid, and Silwet L77.

Embodiments of those where the apparatus further includes at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the apparatus further includes at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the apparatus further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the apparatus further includes at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myo-inositol (inositol). Alternatively, any of these additional components or combinations thereof can be applied in a separate step.

Embodiments include those where the abrasive includes a particulate selected from the group consisting of a mineral abrasive, a metal abrasive, a synthetic abrasive, and an organic abrasive. In embodiments, the apparatus includes particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell par In embodiments, the particulate used in the apparatus is of an average size range from about 2.5 micrometers to about 50 micrometers. In various embodiments, the particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers, as further illustrated in the working Examples.

The abrasion achieved by use of the apparatus preferably does minimal damage to the plant. In embodiments, use of the apparatus results in disruption of cells only in the cuticle, or only in the cuticle and epidermis of the plant. In embodiments, cells deeper than the epidermis are essentially not damaged by the abrasive. In embodiments, use of the apparatus results in systemic silencing, wherein the target gene is silenced in at least one location of the plant that is not the location of abrasion.

Other details relevant to the apparatus or to its use are similar to those described above for the two-step method for silencing a target gene in a plant, as described above under the heading "Methods For Silencing A Target Gene In A Plant Using Abrasives".

A Method For Introducing A Nucleic Acid Into A Whole Plant

Another aspect provides a method for introducing a nucleic acid into a whole plant, including: (a) applying a composition including a nucleic acid to a surface of a plant, and (b) contacting a matrix supporting an abrasive with the surface; whereby the nucleic acid is introduced into the plant. In embodiments, the composition including a nucleic acid is applied to the plant's surface and allowed to dry prior to contacting the plant's surface with a matrix supporting an abrasive. The method is especially useful on intact or whole, growing plants.

In embodiments of the method, the nucleic acid is DNA or RNA or a mixture of both. In embodiments the nucleic acid includes at least 19 consecutive nucleotides having a sequence that is complementary or identical to the sequence of a target gene in the plant. In embodiments the nucleic acid includes at least 19 consecutive nucleotides having a sequence that is complementary or identical to the sequence of a target gene of a pathogen or parasite of the plant. In embodiments, the nucleic acid is synthetic. In embodiments, the nucleic acid is provided in a microbial cell or as a microbial fermentation product. Embodiments of the method include those where the nucleic acid is single-stranded DNA or double-stranded DNA. Embodiments include those wherein the DNA includes coding sequence of the target gene, non-coding sequence of the target gene, or both. Embodiments include those wherein the DNA is contained in a plasmid, or in a viral vector. In embodiments, the DNA is non-transcribable, and is not self-replicating. Embodiments of the method include those where the nucleic acid is RNA. Embodiments include those wherein the RNA includes single-stranded RNA (ssRNA), double-stranded RNA (dsRNA), or a combination of ssRNA and dsRNA. Other details relevant to nucleic acids of use in the method are similar to those described above for RNAs used in the two-step method for silencing a target gene in a plant, as described above under the heading "METHODS FOR SILENCING A TARGET GENE IN A PLANT USING ABRASIVES".

In embodiments of the method, the composition including a nucleic acid is a liquid, a solid, a powder, a solution, an emulsion, or a suspension. In embodiments, the composition including a nucleic acid further includes one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. In specific embodiments, the composition including a nucleic acid further include one or more components selected from the group consisting of sucrose, mannitol, 2-(N-morpholino)ethanesulfonic acid, and Silwet L77.

In embodiments of the method, the composition including a nucleic acid further includes at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the composition further includes at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the composition further includes at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myo-inositol (inositol). Alternatively, any of these additional components or combinations thereof can be applied in a separate step.

Embodiments of the method include those wherein the matrix supports an abrasive that is permanently bonded to the matrix. In other embodiments, the matrix supports an abrasive that is not permanently bonded to the matrix. Embodiments include those wherein the matrix includes a fibrous, porous, non-porous, or adhesive support, and the abrasive includes discrete particles. In embodiments, the matrix includes cotton fiber or other natural fiber. In embodiments, the matrix supporting an abrasive is sandpaper or other solid material incorporating a particulate abrasive permanently bonded to the matrix. An example of the method includes applying the composition including a nucleic acid to a surface of a whole plant, optionally allowing the applied composition to dry, and then applying a matrix supporting an abrasive (such as a fibrous support carrying a particulate abrasive, or sandpaper, or other particulate-abrasive-bearing material) to the same surface to abrade the surface and allow the nucleic acid to be delivered into the plant.

Embodiments of the method include those where the abrasive includes a particulate selected from the group consisting of a mineral abrasive, a metal abrasive, a synthetic abrasive, and an organic abrasive. In embodiments, the abrasive includes particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell par In embodiments, the abrasive used in the method is a particulate abrasive of an average size range from about 2.5 micrometers to about 50 micrometers. In various embodiments, the abrasive used in the method is a particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers, as further illustrated in the working Examples.

The method preferably does minimal damage to the plant. In embodiments, the method results in disruption of cells only in the cuticle, or only in the cuticle and epidermis of the plant. In embodiments, cells deeper than the epidermis are essentially not damaged by the method. In embodiments, the method results in systemic silencing, wherein the target gene is silenced in at least one location of the plant that is not the location where the nucleic acid is applied.

Other details relevant to the method are similar to those described above for the two-step method for silencing a target gene in a plant, as described above under the heading "METHODS FOR SILENCING A TARGET GENE IN A PLANT USING ABRASIVES", and under the heading "AN APPARATUS FOR INTRODUCING A NUCLEIC ACID INTO A WHOLE PLANT".

In embodiments, these methods are useful for obtaining a phenotype (e. g., improved yield, improved resistance temperature, water, or nutrient stress, improved resistance to pathogens, improved herbicide susceptibility, improved herbicide resistance, and modified nutrient content or appearance) resulting from silencing of a target gene in a plant directly treated by these methods. In a related method, the effect of treatment is passed on to subsequent generations, for example where the nucleic acid is designed to target non-coding sequence such as 5' untranslated sequence or a promoter of the target gene, and thereby causing an epigenetic effect. For example, use of a silencing RNA targeting the promoter region of an endogenous phytoene desaturase (PDS) gene in a plant results in bleaching not only of the treated plant but in progeny plants that have not themselves been treated directly with the silencing RNA.

In many embodiments the nucleic acid employed in the methods is designed to silence a target gene. However, in related applications similar methods can be used to deliver any nucleic acid of interest, including nucleic acids designed for gene editing, e. g., using a CRISPR or Cas9 system.

A Method For Introducing A Nucleic Acid Into A Whole Plant

Another aspect provides a method for introducing a nucleic acid into a whole plant, including: (a) applying a composition including an abrasive and a nucleic acid to a surface of a whole plant, and (b) applying pressure to the surface; whereby the nucleic acid is introduced into the plant. The method is especially useful on intact or whole, growing plants. In embodiments, the composition including an abrasive and a nucleic acid is applied to the plant's surface and allowed to dry prior to applying pressure to the plant's surface. In embodiments, the pressure is positive pressure and is applied by mechanical or pneumatic or hydraulic force, e. g., by means of a pressurized gas or liquid or by means of a solid (such as a roller surface or a flat planar surface) applied to the plant's surface. In other embodiments, the pressure includes negative pressure applied by means of a vacuum, similar to vacuum-assisted *Agrobacterium* infiltration.

In embodiments of the method, the nucleic acid in the composition is DNA or RNA or a mixture of both. In embodiments the nucleic acid includes at least 19 consecutive nucleotides having a sequence that is complementary or identical to the sequence of a target gene in the plant. In embodiments the nucleic acid includes at least 19 consecutive nucleotides having a sequence that is complementary or identical to the sequence of a target gene of a pathogen or parasite of the plant. In embodiments, the nucleic acid is synthetic. In embodiments, the nucleic acid is provided in a microbial cell or as a microbial fermentation product. Embodiments of the method include those where the nucleic acid is single-stranded DNA or double-stranded DNA. Embodiments include those wherein the DNA includes coding sequence of the target gene, non-coding sequence of the target gene, or both. Embodiments include those wherein the DNA is contained in a plasmid, or in a viral vector. In embodiments, the DNA is non-transcribable, and is not self-replicating. Embodiments of the method include those where the nucleic acid is RNA. Embodiments include those wherein the RNA includes single-stranded RNA (ssRNA), double-stranded RNA (dsRNA), or a combination of ssRNA and dsRNA. Other details relevant to nucleic acids of use in the method are similar to those described above for RNAs used in the two-step method for silencing a target gene in a plant, as described above under the heading "Methods For Silencing A Target Gene In A Plant Using Abrasives".

In embodiments of the method, the composition including an abrasive and a nucleic acid is a liquid, a solid, a powder, a solution, an emulsion, or a suspension. In embodiments, the composition is a solid or a dry composition, such as a powder. In embodiments, the composition is a suspension of the particulate and the nucleic acid in a liquid or a gel. In embodiments, the composition is an emulsion. In embodiments the nucleic acid is physically closely associated with or in contact with the particulate, e. g., simply by drying the nucleic acid onto the particulate, or by bonding the nucleic acid to the particulate by ionic or electrostatic attraction, direct covalent bonding, covalent bonding using a linker, or by means of an adhesive or other affixing agent.

In embodiments, the composition further includes one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. In specific embodiments, the composition further includes one or more components selected from the group consisting of sucrose, mannitol, 2-(N-morpholino)ethanesulfonic acid, and Silwet L77.

In embodiments of the method, the composition including an abrasive and a nucleic acid further includes at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the composition further includes at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the composition further includes at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myo-inositol (inositol). Alternatively, any of these additional components or combinations thereof can be applied in a separate step.

Embodiments of the method include those where the abrasive includes a particulate selected from the group consisting of a mineral abrasive, a metal abrasive, a synthetic abrasive, and an organic abrasive. In embodiments, the abrasive includes particulate abrasives selected from the group consisting of aluminum oxide, silicon carbide ("carborundum", silicon dioxide, soda lime glass, diatomaceous silica ("diatomaceous earth"), flint, quartz, garnet, silicon dioxide, pumice, sand, feldspar, calcite, steel, tungsten, ceramic, boron carbide, tungsten carbide, an organic or biodegradable abrasive, or combinations of these. In embodiments, the particulate is composed of an organic or biodegradable material, such as, but not limited to wood particles, corn cob particles, grain or seed particles, or nut shell par In embodiments, the abrasive used in the method is a particulate abrasive of an average size range from about 2.5 micrometers to about 50 micrometers. In various embodiments, the abrasive used in the method is a particulate is of an average size range from 2.5-50, 2.5-40, 2.5-30, 2.5-20, 5-50, 5-40, 5-30, 5-20, 7-50, 7-40, 7-30, 7-20, 8-50, 8-40, 8-30, 8-20, 10-50, 10-40, 10-30, or 10-25 micrometers, as further illustrated in the working Examples. In embodiments, the abrasive includes discrete particles.

The method preferably does minimal damage to the plant. In embodiments, the method results in disruption of cells only in the cuticle, or only in the cuticle and epidermis of the plant. In embodiments, cells deeper than the epidermis are essentially not damaged by the method. In embodiments, the method results in systemic silencing, wherein the target gene is silenced in at least one location of the plant that is not the location where the nucleic acid is applied.

Other details relevant to the method are similar to those described above for the two-step method for silencing a target gene in a plant, as described above under the heading "Methods For Silencing A Target Gene In A Plant Using Abrasives" and for the one-step method for silencing a target gene in a plant, as described above under the heading "Single-Step Methods For Silencing A Target Gene In A Plant Using Abrasives".

In embodiments, these methods are useful for obtaining a phenotype (e. g., improved yield, improved resistance temperature, water, or nutrient stress, improved resistance to pathogens, improved herbicide susceptibility, improved herbicide resistance, and modified nutrient content or appearance) resulting from silencing of a target gene in a plant directly treated by these methods. In a related method, the effect of treatment is passed on to subsequent generations, for example where the nucleic acid is designed to target non-coding sequence such as 5' untranslated sequence or a promoter of the target gene, and thereby causing an epigenetic effect. For example, use of a silencing RNA targeting the promoter region of an endogenous phytoene desaturase (PDS) gene in a plant results in bleaching not only of the treated plant but in progeny plants that have not themselves been treated directly with the silencing RNA.

In many embodiments the nucleic acid employed in the methods is designed to silence a target gene. However, in related applications similar methods can be used to deliver any nucleic acid of interest, including nucleic acids designed for gene editing, e. g., using a CRISPR or Cas9 system.

A Method For Introducing A Nucleic Acid Into A Whole Plant

Another aspect provides a method for introducing a nucleic acid into a whole plant including, in any order, the steps of: (a) mechanical penetration of a surface of a whole plant with a non-particulate microstructure, and (b) contacting the surface of a whole plant with a nucleic acid. In embodiments, the non-particulate microstructure is removed after it has penetrated the plant, so that no part of the non-particulate microstructure remains within the plant. The method is especially useful on intact or whole, growing plants.

In embodiments, step (a) is followed by step (b). In other embodiments, step (b) is followed by step (a). In embodiments where the nucleic acid is applied prior to the abrasion step, the nucleic acid can be allowed to dry on the plant surface prior to abrasion. Additional treatments of the plant (for example, treatment with a surfactant, an nuclease inhibitor, a photoprotectant, or a rainfastness agent) are optionally performed, subsequent to either abrasion or application of nucleic acid, or concomitant with either or both steps. A related, one-step method includes the step of mechanically penetrating the a surface of a whole plant with a non-particulate microstructure bearing a nucleic acid, whereby the nucleic acid is delivered into the plant.

In embodiments of the method, the nucleic acid in the composition is DNA or RNA or a mixture of both. In embodiments the nucleic acid includes at least 19 consecutive nucleotides having a sequence that is complementary or identical to the sequence of a target gene in the plant. In embodiments the nucleic acid includes at least 19 consecutive nucleotides having a sequence that is complementary or identical to the sequence of a target gene of a pathogen or parasite of the plant. In embodiments, the nucleic acid is synthetic. In embodiments, the nucleic acid is provided in a microbial cell or as a microbial fermentation product. Embodiments of the method include those where the nucleic acid is single-stranded DNA or double-stranded DNA. Embodiments include those wherein the DNA includes coding sequence of the target gene, non-coding sequence of the target gene, or both. Embodiments include those wherein the DNA is contained in a plasmid, or in a viral vector. In embodiments, the DNA is non-transcribable, and is not self-replicating. Embodiments of the method include those where the nucleic acid is RNA. Embodiments include those wherein the RNA includes single-stranded RNA (ssRNA), double-stranded RNA (dsRNA), or a combination of ssRNA and dsRNA. Other details relevant to nucleic acids of use in the method are similar to those described above for RNAs used in the two-step method for silencing a target gene in a plant, as described above under the heading "Methods For Silencing A Target Gene In A Plant Using Abrasives".

In embodiments, the nucleic acid is ssRNA or dsRNA designed to silence a single target gene. In embodiments, the nucleic acid is ssRNA or dsRNA including multiple repeating segments for targeting a single target gene. Multiple target genes (which can be target genes of the plant, or of a pathogen or parasite of the plant, or a combination of both), or multiple regions of a single target gene, can be targeted by a chimeric nucleic acid, such as by a chimeric RNA. In an example, the nucleic acid is a chimeric dsRNA including dsRNA segments targeting a gene expressed in the plant and dsRNA segments targeting a gene of a pathogen or parasite of the plant.

In embodiments of the method, the nucleic acid is in the form of a liquid, a solid, a powder, a solution, an emulsion, or a suspension. In embodiments, the nucleic acid is in the form of a solid or a dry composition, such as a powder. In embodiments, the nucleic acid is in the form of a suspension of the nucleic acid in a liquid or a gel. In embodiments, the nucleic acid is in the form of an emulsion. In embodiments the nucleic acid is physically closely associated with or in contact with the non-particulate microstructure, e. g., simply by drying the nucleic acid onto the non-particulate microstructure, or by bonding the nucleic acid to the particulate by ionic or electrostatic attraction, or by means of an adhesive or other affixing agent. In embodiments the nucleic acid is bonded to the non-particulate microstructure by direct covalent bonding or by covalent bonding using a linker, wherein the covalent bond can be broken (e. g., by enzymatic action) in order to deliver the nucleic acid to the plant.

In embodiments, the nucleic acid is in the form of a composition wherein the composition further includes one or more components selected from the group consisting of a surfactant, a buffer, an osmoprotectant, a cryoprotectant, an RNase inhibitor (ideally compatible with RNAi activity), a nucleic acid condensing agent (e. g., a polyamine), a transfection agent, a wound-response inhibitor (e. g., callose, hydrogen peroxide inhibitors), a salt (e. g., a $Zn^{+2}$ or $Mg^{+2}$ salt), a plant hormone, a sugar, and a sugar alcohol. In specific embodiments, the nucleic acid is in the form of a composition wherein the composition further includes one or more components selected from the group consisting of sucrose, mannitol, 2-(N-morpholino)ethanesulfonic acid, and Silwet L77.

In embodiments of the method, the nucleic acid is in the form of a composition wherein the composition further includes at least one selected from the group consisting of water, a biocide, a chelator, a buffer, a nonionic surfactant, a zwitterionic surfactant, a zinc or magnesium salt, a defoamer, a rainfastness agent, and a photoprotectant. In embodiments, the composition further includes at least one selected from the group consisting of a carrier agent, a surfactant, an osmolyte, an organosilicone, a polynucleotide herbicidal molecule, a non-polynucleotide herbicidal molecule, a non-polynucleotide pesticide, a safener, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the composition further includes at least one osmolyte such as an amino acid osmolyte, a methylamine osmolyte, or a polyol or sugar or sugar alcohol osmolyte; non-limiting examples suitable osmolytes include sorbitol, mannitol, xylitol, erythrol, glycerol, glucose, sucrose, proline, valine, isoleucine, ectoine, aspartic acid, trehalose, glycine betaine (betaine), carnitine, taurine, sarcosine, myoinositol (inositol). Alternatively, any of these additional components or combinations thereof can be applied in a separate step.

Embodiments of the method include those where the non-particulate microstructure includes a matrix or apparatus on which is supported at least one selected from the group consisting of micro- or nano-needles, -whiskers, -fibers, and -wires.

The method preferably does minimal damage to the plant. In embodiments, the method results in disruption of cells only in the cuticle, or only in the cuticle and epidermis of the plant. In embodiments, cells deeper than the epidermis are essentially not damaged by the method. In embodiments, the method results in systemic silencing, wherein the target gene is silenced in at least one location of the plant that is not the location where the nucleic acid is applied.

Other details relevant to the method are similar to those described above for the two-step method for silencing a target gene in a plant, as described above under the heading "METHODS FOR SILENCING A TARGET GENE IN A PLANT USING ABRASIVES" and for the one-step method for silencing a target gene in a plant, as described above under the heading "Single-Step Methods For Silencing A Target Gene In A Plant Using Abrasives".

In embodiments, these methods are useful for obtaining a phenotype (e. g., improved yield, improved resistance temperature, water, or nutrient stress, improved resistance to pathogens, improved herbicide susceptibility, improved herbicide resistance, and modified nutrient content or appearance) resulting from silencing of a target gene in a plant directly treated by these methods. In a related method, the effect of treatment is passed on to subsequent generations, for example where the nucleic acid is designed to target non-coding sequence such as 5' untranslated sequence or a promoter of the target gene, and thereby causing an epigenetic effect. For example, use of a silencing RNA targeting the promoter region of an endogenous phytoene desaturase (PDS) gene in a plant results in bleaching not only of the treated plant but in progeny plants that have not themselves been treated directly with the silencing RNA.

In many embodiments the nucleic acid employed in the methods is designed to silence a target gene. However, in related applications similar methods can be used to deliver any nucleic acid of interest, including nucleic acids designed for gene editing, e. g., using a CRISPR or Cas9 system.

Regenerated Plants And Progeny Thereof

Another aspect provides for providing a plant exhibiting modification of a target gene in the plant, comprising directly regenerating a plant from a source plant, wherein the source plant has been contacted with a composition comprising an RNA that comprises at least 19 consecutive nucleotides having a sequence that is complementary or identical to the sequence of a target gene in the plant, wherein the directly regenerated plant exhibits modification of the target gene. Related aspects provide a plant exhibiting modification of a target gene in the plant, comprising directly regenerating a plant from a source plant, wherein the source plant has been contacted with a composition comprising at least one nucleic acid (an RNA or a DNA or a combination of RNA and DNA) that comprises at least 19 consecutive nucleotides having a sequence that is complementary or identical to the sequence of a target gene in the plant, wherein the directly regenerated plant exhibits modification of the target gene.

In embodiments, the source plant is a growing seedling or a growing plant in a post-seedling growth stage. In embodiments, the source plant is an intact plant. Embodiments include use of the various methods, compositions, and apparatuses described herein. In embodiments, the source plant is topically treated with the RNA.

In embodiments, the modification of the target gene is (1) non-heritable silencing of the target gene, (2) heritable or epigenetic silencing of the target gene, or (3) a change in the nucleotide sequence of the target gene. In embodiments, the directly regenerated plant exhibits partial silencing of the target gene, or the directly regenerated plant exhibits complete systemic silencing of the target gene, or the directly regenerated plant exhibits a homogeneous morphological or physiological phenotype resulting from modification of the target gene. In embodiments, the modification of the target gene is heritable to plants of subsequent generations grown from the directly regenerated plant. Thus, aspects include the directly regenerated plant exhibiting modification of the target gene as well as plants of subsequent generations exhibiting modification of the target gene.

Related Information And Techniques

Plants

The methods, apparatuses, and compositions described herein are useful across a broad range of plants. Suitable plants in which the methods apparatuses, and compositions disclosed herein can be used include, but are not limited to, cereals and forage grasses (rice, maize, wheat, barley, oat, *sorghum*, pearl millet, finger millet, cool-season forage grasses, and bahiagrass), oilseed crops (soybean, oilseed brassicas including canola and oilseed rape, sunflower, peanut, flax, sesame, and safflower), legume grains and forages (common bean, cowpea, pea, *faba* bean, lentil, tepary bean, Asiatic beans, pigeonpea, vetch, chickpea, lupine, alfalfa, and clovers), temperate fruits and nuts (apple, pear, peach, plums, berry crops, cherries, grapes, olive, almond, and Persian walnut), tropical and subtropical fruits and nuts (citrus including limes, oranges, and grapefruit; banana and plantain, pineapple, *papaya*, mango, avocado, kiwifruit, passionfruit, and persimmon), vegetable crops (solanaceous plants including tomato, eggplant, and peppers; vegetable brassicas; radish, carrot, cucurbits, alliums, asparagus, and leafy vegetables), sugar, tuber, and fiber crops (sugarcane, sugar beet, *stevia*, potato, sweet potato, cassava, and cotton), plantation crops, ornamentals, and turf grasses (tobacco, coffee, cocoa, tea, rubber tree, medicinal plants, ornamentals, and turf grasses), and forest tree species.

In certain embodiments, the plant is a weedy plant. Weedy plants are plants that compete with cultivated plants, those of particular importance include, but are not limited to important invasive and noxious weeds and herbicide resistant biotypes in crop production, such as, *Amaranthus* species—*A. albus, A. blitoides, A. hybridus, A. palmeri, A. powellii, A. retroflexus, A. spinosus, A. tuberculatus*, and *A. viridis; Ambrosia* species—*A. trifida, A. artemisifolia; Lolium* species—*L. multiflorum, L. rigidium, L perenne; Digitaria* species *D. insularis; Euphorbia* species—*E. heterophylla; Kochia* species—*K. scoparia; Sorghum* species—*S. halepense; Conyza* species—*C. bonariensis, C. canadensis, C. sumatrensis; Chloris* species—*C. truncate; Echinochola* species—*E. colona, E. crus-galli; Eleusine* species—*E. indica; Poa* species *P. annua; Plantago* species—*P. lanceolata; Avena* species—*A. fatua; Chenopodium* species—*C. album; Setaria* species—*S. viridis, Abutilon theophrasti, Ipomoea* species, *Sesbania*, species, *Cassia* species, *Sida* species, *Brachiaria*, species and *Solanum* species.

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridis* var, *robusta-alba schreiber, Setaria viridis* var, *robusta-purpurea, Snowdenia polystachea, Sorghum sudanese, Alisma plantago-aquatica, Amaranthus lividus, Amaranthus quitensis, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandra* var, *pedicellata, Euphorbia heterophylla, Fallopia convolvulus, Fimbristylis miliacea, Galeopsis tetrahit, Galium spurium, Helianthus annuus, Iva xanthifolia, Ixophorus unisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubia* var, *major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica* var, *uliginosa, Sagittaria guyanensis, Sagittaria montevidensis, Sagittaria pygmaea, Salsola iberica, Scirpus juncoides* var, *ohwianus, Scirpus mucronatus, Setaria lutescens, Sida spinosa, Sinapis arvensis, Sisymbrium orientale, Sisymbrium thellungii, Solanum ptycanthum, Sonchus aspen, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea*, and *Senecio vulgaris.*

Additional Nucleic Acid Elements

Embodiments of the nucleic acids useful in the compositions and methods described herein can include additional elements, such as promoters, small RNA recognition sites, aptamers or ribozymes, additional and additional expression cassettes for expressing coding sequences (e. g., to express a transgene such as an insecticidal protein or selectable marker) or non-coding sequences (e. g., to express additional suppression elements). In an embodiment, a nucleic acid useful in methods or compositions as described herein includes a recombinant DNA construct including a heterologous promoter operably linked to DNA encoding an RNA transcript including at least 19 consecutive nucleotides having a sequence that is complementary or identical to the sequence of a target gene in the plant or to the sequence of a target gene of a pathogen or parasite of the plant. In an embodiment, a nucleic acid useful in methods and compositions described herein is a DNA or RNA including an aptamer that serves to guide the nucleic acid to a desired location in the plant. In an embodiment, a nucleic acid useful in methods and compositions described herein is an RNA molecule including one or more recognition sites for binding and cleavage by a small RNA (e. g., by a miRNA or an siRNA that is expressed only in a particular cell or tissue), which allows for more precise control of the suppression of the target gene in the plant.

EXAMPLES

Example 1

This example illustrates non-limiting embodiments of methods, apparatuses, and compositions useful for delivering a nucleic acid into a plant or cells or tissues of a plant. More specifically, this example describes silencing a target gene by way of particulate-assisted delivery of a nucleic acid such as an RNA "trigger" or silencing element into a plant. The methods generally involve treatment of the surface of a plant (or of plant cells or tissues) with an abrasive or particulate, and with a nucleic acid.

Four dsRNA "triggers" (silencing elements) of 50, 78, 124, and 249 base-pairs (bp) (SEQ ID NOs:1, 2, 3, and 5, respectively), and targeting green fluorescent protein (GFP) were used to silence the GFP gene in a transgenic *Nicotiana benthamiana* line (16c) expressing GFP. For each trigger, 420 micrograms of total RNA were dissolved in 210 microliters; 10 microliters were removed for later analysis and the remaining 200 microliters was added to 200 milligrams of aluminum oxide (~220 mesh) particles in a 15 milliliter culture tube. The preparation was incubated overnight at 37 degrees Celsius, then centrifuged at 250 rpm with the cap off. One milliliter of 100% ethanol was added to transfer the RNA-coated aluminum oxide particles into a weighing tray; excess liquid was removed by pipette and the particles allowed to air-dry. Each preparation of the dry particles was loaded into the chamber of an airbrush and sprayed at 45-65 pounds per square inch (psi) onto a single leaf of each of six plants. Local silencing in the treated leaf was observed in 3 of the 6 plants sprayed with the 124 bp dsRNA trigger, but not in the plants treated with the 50 or 78 bp dsRNA triggers. No silencing was observed in plants treated with the 249 bp dsRNA trigger but these results were not considered based on subsequent analysis of trigger quality. Systemic GFP silencing (outside of the treated leaves) was not observed in this experiment.

Example 2

This example illustrates non-limiting embodiments of methods, apparatuses, and compositions useful for delivering a nucleic acid into a plant or cells or tissues of a plant. More specifically, this example describes silencing a target gene by way of particulate-assisted delivery of a nucleic acid such as an RNA "trigger" or silencing element into a plant.

In another example, 1500 micrograms of dsRNA trigger in 1 milliliter water was added to 200 milligrams of aluminum oxide (320 mesh (20.1-23.1 micrometers) or 400 mesh (15.5-17.5 micrometers)) in a 6-well plate and incubated overnight at room temperature on a shaker (150 rpm). One milliliter of 100% ethanol was added to transfer the RNA-coated aluminum oxide particles into a weighing tray; excess liquid was removed by pipette and the particles allowed to air-dry. Each preparation of the dry particles was loaded into the chamber of an airbrush and sprayed at 55 pounds per square inch (psi) onto leaves of nine transgenic *Nicotiana benthamiana* 16c plants. Results are provided in Table 3. Local silencing in the treated leaf was observed in nearly all plants treated with the GFP dsRNA trigger (SEQ ID NO:3), with less efficient GFP silencing observed in the plants treated with the GFP/PDS fusion dsRNA trigger (SEQ ID NO:7, which contains the intact sequence of SEQ ID NO:3 at its 3' end). The larger particle size (320 mesh) provided better silencing efficiency than the smaller particles (400 mesh). Systemic GFP silencing (outside of the treated leaves) was not observed in this experiment.

TABLE 3

| SEQ ID NO:* | dsRNA trigger size (base pairs) | Target gene | Aluminum oxide mesh size | Number of plants where GFP silencing was observed |
|---|---|---|---|---|
| 3 | 124 | GFP | 320 | 9/9 |
| 3 | 124 | GFP | 400 | 7/9 |
| 7 | 300 | GFP/PDS fusion | 320 | 5/9 |
| 7 | 300 | GFP/PDS fusion | 400 | 2/9 |

*sequence of anti-sense strand, 5'→3'

Example 3

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

In another example, 1.5 milligrams of total RNA (124 bp dsRNA, SEQ ID NOs:3) were coated onto aluminum oxide or silicon carbide particles and applied using an airbrush spray (65 psi) onto 9 two- to three-week-old transgenic *Nicotiana benthamiana* 16c plants. Phenotype was recorded 17 days after the treatment. Plants showing GFP silencing (red spots/sectors under ultraviolet light) on sprayed leaves only were scored as displaying local silencing. Plants additionally showing GFP silencing (red spots/sectors under ultraviolet light) in parts of the plants other than the sprayed leaves were scored as displaying systemic silencing; in this experiment the systemic silencing was observed as a vasculature-associated GFP silencing pattern in newly grown leaves. Results are provided in Table 4.

TABLE 4

| SEQ ID NO:* | Particulate type | Particulate mesh size | Number of plants displaying local silencing | Number of plants displaying systemic silencing | Number of plants displaying no silencing |
|---|---|---|---|---|---|
| 3 | $Al_2O_3$ | 320 | 8/9 | 1/9 | 0/9 |
| 3 | $Al_2O_3$ | 360 | 7/9 | 1/9 | 1/9 |
| 3 | SiC | 320 | 8/9 | 1/9 | 0/9 |
| 3 | SiC | 360 | 6/9 | 3/9 | 0/9 |

*sequence of anti-sense strand, 5'→3'

Example 4

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

In another example, different RNA triggers designed to silence GFP were compared. Several triggers were blunt-ended dsRNAs; one (SEQ ID NO:8) was a single-stranded miRNA precursor transcript designed to self-hybridize and be processed to produce a mature miRNA targeting GFP. For each RNA trigger, 1.5 milligrams of total RNA were coated onto SiC particles. Each individual RNA trigger was dissolved in water to make up 1 milliliter, added to 200 milligrams SiC (320 mesh) in a well of a 6-well plate. The plate was placed in a fume hood to air-dry with gentle shaking. After the plate was completely dry, 100% ethanol was added to transfer the RNA-coated SiC particles into a weighing tray; excess liquid was removed by pipette and the particles allowed to air-dry overnight. The dried RNA-coated particles were transferred to 2-milliliter microcentrifuge tubes, ground briefly in the tubes, and applied using an airbrush spray (60 psi) onto 9 three-week-old transgenic *Nicotiana benthamiana* 16c plants. Local silencing was observed beginning at 4-5 days after treatment. Phenotype was recorded at 9 days (for local silencing) and at 19 days (for systemic silencing) after treatment. In this experiment, systemic silencing was again observed as a vasculature-associated GFP silencing pattern in newly grown leaves. Results are provided in Table 5.

TABLE 5

| SEQ ID NO: | dsRNA trigger size (base pairs) | Target gene | Number of plants displaying local silencing | Number of plants displaying systemic silencing | Number of plants displaying no silencing |
|---|---|---|---|---|---|
| 1 | 50 | GFP | 4/9 | 0/9 | 5/9 |
| 2 | 78 | GFP | 8/9 | 2/9 | 1/9 |
| 3 | 124 | GFP | 9/9 | 5/9 | 0/9 |
| 4 | 125 | GFP | 4/9 | 0/9 | 5/9 |
| 5 | 249 | GFP | 3/9 | 0/9 | 6/9 |
| 8** | 355 | GFP | 1/9 | 0/9 | 8/9 |
| 6 | 258 | PDS | 0/9 | 0/9 | 9/9 |
| — | — | (none) | 0/9 | 0/9 | 9/9 |
| — | — | (none) | 0/9 | 0/9 | 9/9 |

*sequence of anti-sense strand, 5'→3'

**SEQ ID NO: 8 is a synthetic miRNA precursor; the sequence is of the complete transcript, 5'→3'

Example 5

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as DNA viral vector into a plant.

A viral vector was used to silence either a green fluorescent protein (GFP) transgene or an endogenous phytoene desaturase (PDS) target gene in treated plants. Plasmid A1 (SEQ ID NO:9) targeting PDS or plasmid A2 (SEQ ID NO:10) targeting GFP was combined with plasmid B (ToGMoV DNA-B in the pUC19 vector, SEQ ID NO:11) to produce a VIGS system. 250 micrograms of either plasmid A1 (SEQ ID NO:9) or plasmid A2 (SEQ ID NO:10) was added to 250 micrograms plasmid B (SEQ ID NO:11) in 600 microliters water. The DNA mixtures were each added to 150 milligrams of aluminum oxide particles (400 mesh or 600 mesh) in wells of a 6-well plate and incubated overnight at room temperature on a shaker (150 rpm) in a fume hood to air dry. After the plate was completely dry, 1 milliliter of 70% ethanol was added to transfer the RNA-coated aluminum oxide particles into a weighing tray; excess liquid was removed by pipette and the particles allowed to air-dry. Each preparation of the dried DNA-coated particles was applied using an airbrush spray (55 psi) onto six transgenic *Nicotiana benthamiana* 16c plants. Results are shown in Table 6. The results demonstrate that particle-assisted delivery of a viral vector results in systemic silencing of transgenes or endogenous genes expressed in a whole plant. This technique is useful in other applications, such as in virus resistance assays, as the method does not involve *Agrobacterium*-mediated infection.

TABLE 6

| Plasmid ID | SEQ ID NO: | Target gene | Aluminum oxide mesh size | Number of plants displaying systemic PDS silencing | Number of plants displaying systemic GFP silencing |
|---|---|---|---|---|---|
| A1 | 9 | PDS | 400 | 5/6 | — |
| A2 | 10 | GFP | 400 | — | 4/6 |
| A1 | 9 | PDS | 600 | 1/6 | — |
| A2 | 10 | GFP | 600 | — | 6/6 |

Example 6

This example illustrates non-limiting embodiments of methods, apparatuses, and compositions useful for delivering a nucleic acid into a plant or cells or tissues of a plant. More specifically, this example describes systemic silencing of a target gene by way of abrasion of a plant surface with particulates to disrupt the cuticle or epidermis, thereby delivering a nucleic acid such as an RNA "trigger" or silencing element into a plant.

Double-stranded RNA was labelled with Cy3 as a fluorescent marker and coated onto SiC particles (320 mesh) which were then sprayed onto a leaf. The leaf was imaged with confocal fluorescence microscopy 1 day after treatment. The images obtained showed that the fluorescently labelled particles were located at the bottom of "craters" formed by the particle impact some layers deep in the leaf epidermis and suggested that, while most of the fluorescence was still associated with the particles, some of the fluorescence diffused into adjacent undamaged cells. The images suggest that the nucleic acid on the particles is not delivered directly into cells in the manner seen with gene gun delivery using much smaller particles, but by diffusion into cells adjacent to the larger particles used here with relatively low-pressure delivery.

Example 7

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared varying distances between airbrush nozzle and plant surface. 1.5 milligrams of blunt-ended dsRNA targeting GFP (SEQ ID NO:3) was coated onto 100 milligrams of silicon carbide (360 mesh) and air dried overnight. After drying, the mixture was ground to singulate the particles, and loaded into a G78 airbrush mounted to a ring stand. Transgenic *Nicotiana benthamiana* 16c plants were each sprayed with three 1-second bursts at 3, 5, and 7 centimeters nozzle-to-leaf distance). Phenotype (GFP silencing) was visually assessed using blue light excitation 7 days after treatment. In addition, GFP expression was quantified in the red (silenced) and green (non-silenced) sectors using qPCR. Results: the 3-centimeter spray distance damaged the plants and resulted in little silencing; approximately equivalent silencing was observed with the 5- and 7-centimeter spray distances. The qPCR measurements demonstrated that GFP expression was correlated to visual phenotype (FIG. 1).

Example 8

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

An experiment to test sequential application of RNA and particulate abrasive was performed. Blunt-ended dsRNA targeting GFP (SEQ ID NO:3) was dissolved in water at 1, 5, and 10 milligrams/milliliter, with a silicone surfactant (0.1% Silwet L77) added to aid spreading on the leaf surface. 20 microliters of the RNA solution was applied to three leaves of transgenic *Nicotiana benthamiana* 16c plants and allowed to dry briefly. Dry uncoated silicon carbide (360 mesh) particles were sprayed onto the RNA-coated leaves at 60 psi using a G78 airbrush mounted to a ring stand at 5 centimeters nozzle-to-leaf distance from the plants. GFP silencing was assessed visually using blue light excitation at 7 days after treatment. Leaf damage prevented full interpretation of the dsRNA rate data, but GFP silencing was observed using this sequential method, where applying an RNA to the surface of the plant is followed by abrading the surface of a plant with a particulate of a size greater than about 2.5 micrometers.

Example 9

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of a single-step application of RNA-coated particulates and a two-step sequential application. The effects of mannitol and a surfactant were also examined.

For single-step application of dry, RNA-coated particulates, 1.5 milligrams of a blunt-ended dsRNA trigger targeting GUS (SEQ ID NO:12) or of a blunt-ended dsRNA trigger targeting GFP (SEQ ID NO:3) were dissolved in either water or 200 millimolar mannitol. 100 milligrams SiC particles (360 mesh) were added to the RNA solutions, and the mixture was air dried overnight. The dry RNA-coated particles were sprayed at 60 psi in three 1-second bursts onto the leaves of transgenic *Nicotiana benthamiana* 16c plants using a G78 airbrush mounted to a ring stand at 5 centimeters nozzle-to-leaf distance from the plants. For two-step sequential application, the dsRNA triggers were dissolved in water, with or without 0.2% Silwet L77, and with or without 200 millimolar mannitol. Twenty microliters of RNA solution was applied to each of three leaves of transgenic *Nicotiana benthamiana* 16c plants and allowed to dry briefly. Dry uncoated silicon carbide (360 mesh) particles were sprayed onto the RNA-coated leaves at 60 psi using a G78 airbrush mounted to a ring stand at 5 centimeters nozzle-to-leaf distance from the plants. GFP silencing was assessed visually using blue light excitation at 7 days after treatment. The silencing frequency of dry coated particles and sequential application was found to be approximately the same. The addition of mannitol had no effect in the single-step application of dry, RNA-coated but had a positive effect on the two-step sequential application, by apparent reduction in leaf damage.

Example 10

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of different particulate abrasives in a two-step sequential application method, where applying an RNA to the surface of the plant is followed by abrading the surface of a plant with a particulate of a size greater than about 2.5 micrometers.

Figure 2:
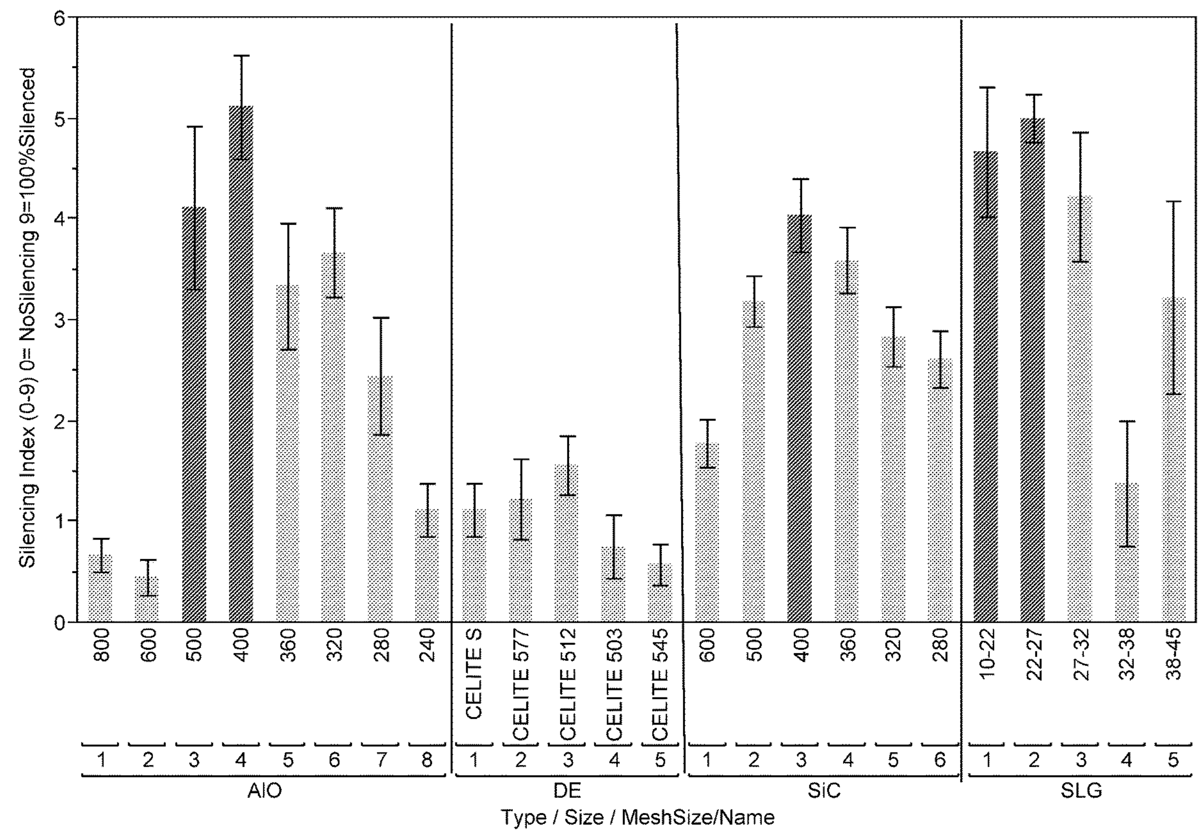
FIG. 2 depicts visual silencing efficacy for the different particulates tested, as described in Example 10. "AlO"=aluminum oxide (listed by mesh size), "DE"=diatomaceous earth (listed as Celite grades), "SiC"=silicon carbide (listed by mesh size), "SLG"=soda lime glass (listed by bead diameter range in micrometers).

Particulate abrasives tested included silicon carbide (SiC, angular), aluminum oxide ($Al_2O_3$, angular), soda lime glass ("SLG", round) and diatomaceous silica ("diatomaceous earth", "DE", angular) particles with the size ranges provided in Table 2 (see Example 1). Blunt-ended dsRNA triggers targeting GFP (SEQ ID NO:3) or magnesium chelatase (SEQ ID NO:13) were diluted to 5 milligrams/milliliter in 200 millimolar mannitol containing 0.05% Silwet L77. Fifteen microliters of RNA solution was hand applied using a pipette onto two leaves of transgenic *Nicotiana benthamiana* 16c plants and allowed to dry briefly. Dry uncoated particles were sprayed in three 1-second bursts onto the RNA-coated leaves at 60 psi using a G78 airbrush mounted to a ring stand at 7 centimeters nozzle-to-leaf distance from the plants. GFP silencing was assessed visually using blue light excitation at 7 days after treatment. The results comparing visual silencing efficacy for the different particulates is depicted in FIG. 2. Under the conditions in this experiment, the greatest silencing with lowest leaf damage generally resulted from use of particles of about 10 to about 25 micrometers in size. The use of larger particles also resulted in GFP silencing but also caused heavier leaf damage. The use of smaller particles resulted in less silencing and less leaf damage. Particulate shape (angular or round) had little effect on silencing efficiency. Density appeared to be an important factor as little silencing was observed with diatomaceous silica, the least dense particle tested.

Example 11

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of a single-step application of RNA-coated particulates and a two-step sequential application. The GFP silencing efficacy of a 124 bp dsRNA trigger (SEQ ID NO:3) and of a 22 bp dsRNA trigger (SEQ ID NO:14) was also compared.

In the single-step method, the dsRNA trigger was diluted in water and added to 200 milligrams SiC (400 mesh), air dried overnight with gentle agitation, ground gently and sieved through 270 mesh. Thirty microliters of an aqueous solution of 0.05% Silwet L77, 200 millimolar mannitol was applied by hand to the top two expanded leaves and terminal leaf of transgenic *Nicotiana benthamiana* 16c plants; the dry dsRNA-coated particles were sprayed in three 1-second bursts onto the Silwet L77/mannitol-coated leaves at 60 psi using a G78 airbrush mounted to a ring stand at 7 centimeters nozzle-to-leaf distance from the plants. To estimate the amount of dsRNA delivered, three 1-second bursts of the dry dsRNA-coated particles were sprayed into 100 microliters of water in a centrifuge tube which was then vortexed, and the dsRNA concentration estimated by UV spectrometry.

In the two-step method, the dsRNA trigger was diluted in water. Silwet L77 and mannitol was added to the dsRNA solution to final concentrations of 0.05% and 200 millimolar, respectively. Thirty microliters of the dsRNA solution was applied by hand to the top two expanded leaves and terminal leaf of transgenic *Nicotiana benthamiana* 16c plants; the treated leaves were allowed to air dry 10 minutes. SiC (400 mesh) particles were sprayed in three 1-second bursts onto the Silwet L77/mannitol-coated leaves at 60 psi using a G78 airbrush mounted to a ring stand at 7 centimeters nozzle-to-leaf distance from the plants.

GFP silencing was assessed visually using blue light excitation at 7 days after treatment. In this experiment, GFP silencing efficiency for the single-step and two-step application methods appeared to be similar, and, while on a mass basis the 22 bp dsRNA trigger was more efficient than the 124 bp dsRNA trigger, the efficiency was similar when compared on a mole basis.

Example 12

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as an RNA "trigger" or silencing element into a plant.

This experiment compared the silencing efficiency of a single-step application of RNA-coated particulates, a two-step sequential application, a single-step high-pressure spray application of RNA without particulates, and a single-step high-pressure spray application of an RNA/particulate suspension. A commercial spray tip fitted in a track sprayer was used.

Blunt-ended dsRNA triggers targeting GFP (SEQ ID NO:3) or magnesium chelatase (SEQ ID NO:13) were diluted to 5 milligrams/milliliter in 200 millimolar mannitol containing 0.05% Silwet L77. For the RNA/particulate suspensions, diatomaceous silica (Celite 512) or SiC (360 mesh) was added to the above RNA solutions at 20 milligrams/milliliter. The RNA preparations were sprayed onto transgenic *Nicotiana benthamiana* 16c plants at either 60 or 85 psi using a canister sprayer fitted with a TeeJet 40005E flat fan nozzle positioned 7 centimeters from the plants. The plants sprayed at 60 psi were sprayed a second time with dry uncoated particles applied at 80 psi with a canister sprayer fitted with a TeeJet DG110015 nozzle 10 centimeters from the plants. GFP silencing was assessed visually using blue light excitation at 7 days after treatment. Silencing efficiency was very low in the plants sprayed only with RNA solutions (no particulates). Silencing using either the RNA/Celite or RNA/SiC suspensions was observed for both GFP and magnesium chelatase; for GFP the silencing efficacy was less than that resulting from a two-step sequential application, but for magnesium chelatase the silencing efficacy was comparable. These results indicate that a single-step application of an RNA/particulate suspension is efficacious and can be advantageously used with commercial spraying equipment.

Example 13

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of an RNA "trigger" into maize plants.

This experiment demonstrates silencing of a GFP transgene in maize (*Zea mays*). A 121 bp dsRNA targeting GFP (SEQ ID NO:15) was diluted to 5 milligrams/milliliter in water containing 0.05% Silwet L77. Thirty microliters of the RNA solution was applied to a single corn (*Zea mays*) leaf and allowed to dry briefly. Dry uncoated silicon carbide particles (280, 320, 360, and 400 mesh) were sprayed at 60 psi on the dsRNA-coated leaves using a G78 airbrush mounted to a ring stand 5 centimeters from the plants. GFP silencing was assessed visually using blue light excitation at 7 days after treatment. GFP silencing was observed in plants sprayed with 280, 320, and 360 mesh SiC. The silenced sectors manifested as a long stripe (in one plant treated with 360 mesh SiC) or multiple small spots (in two plants treated respectively with 280 and 320 mesh SiC). Silenced and non-silenced sectors were sampled in the leaves and GFP expression was measured. GFP expression was reduced by about 30 to about 50 percent in silenced sectors compared to non-silenced sectors was observed in both silenced sector types (stripe and spots).

Example 14

This example illustrates non-limiting embodiments of methods, apparatuses, and compositions useful for delivering a nucleic acid into a plant or cells or tissues of a plant. More specifically, this example describes systemic silencing of a target gene by various methods including contacting a plant surface with a matrix supporting an abrasive. In these experiments, cotton swabs supporting a particulate abrasive, uncoated or coated with dsRNA trigger, are used to abrade a plant surface and deliver a dsRNA trigger to the plant.

In a first experiment, dry dsRNA-coated particles were prepared by mixing 100 milligrams of silicon carbide (360 mesh) particles per 1 milliliter of formulations containing 1.5 milligrams/milliliter 78 bp dsRNA against GFP (SEQ ID NO:2) in: a) water, b) 4 millimolar MES buffer, c) 200 millimolar mannitol, or, d) 4 millimolar MES buffer and 200 millimolar mannitol. The dsRNA-SiC mixtures were air dried overnight on a rotational shaker. A cotton swab was loaded with the dry, dsRNA-coated SiC particles by pressing the swab into the prepared SiC particles, and then used to gently abrade the upper leaf surface of approximately 4-week old transgenic *Nicotiana benthamiana* 16c plants by gently rolling the swab along the leaf surface with the leaf supported from below by the worker's finger. GFP silencing was assessed visually using blue light excitation at 7 days after treatment. In this experiment, addition of 200 millimolar mannitol to the dsRNA formulation prevented leaf dehydration after abrasion using cotton-swab rolling with dsRNA coated SiC particles. Addition of 4 millimolar MES and 200 millimolar mannitol to the dsRNA formulation enhanced frequency of GFP silencing foci in the treated leaves.

In a second experiment, dry dsRNA-coated SiC particles were manufactured by prepared by mixing 100 milligrams of silicon carbide (360 mesh) particles per 1 milliliter of an aqueous dsRNA solution at the following trigger concentrations: a) 1.5 milligrams/milliliter of a 78 bp dsRNA trigger against GFP (SEQ ID NO:2), b) 1.5 milligrams/milliliter of a 76 bp dsRNA trigger against the *N. benthamiana* 16C magnesium chelatase (SEQ ID NO:16), and c) a mix of both triggers at 0.75 milligrams/milliliter each. The dsRNA-SiC mixtures were air dried overnight on a rotational shaker. A cotton swab was loaded with the dry, dsRNA-coated SiC particles by pressing the swab into the prepared SiC particles, and then used to gently abrade the upper leaf surface of approximately 4-week old transgenic *Nicotiana benthamiana* 16c plants by gently rolling the swab along the leaf surface with the leaf supported from below by the worker's finger. The same dry, dsRNA-coated SiC particle preparations were delivered to a second set of plants using an airbrush. Silencing was assessed visually using ambient light or blue light excitation at 7 days after treatment. In this experiment, GFP and magnesium chelatase silencing foci were observed in treated leaves with all particle coating protocols and delivery methods. The expected gene-target-specific phenotypes were observed in plants treated with a single dsRNA trigger, and phenotype co-localization was observed in plants treated with both dsRNA triggers.

In a third experiment, efficacy of three different two-step sequential delivery methods using the cotton-swab rolling technique was tested in *N. benthamiana* 16C seedlings. In these methods, the dsRNA trigger is applied to the plant surface prior to abrasion of the plant surface with uncoated particulates supported on a cotton swab.

The two-step sequential delivery methods tested were:

(a) Method 1: the dsRNA formulation was pipetted onto the leaf surface and spread with a pipette tip to ensure uniform coverage, followed by abrasion by rolling a cotton-swab carrying uncoated SiC particles;

(b) Method 2: leaves were abraded by rolling a cotton-swab carrying uncoated SiC particles, followed by pipette delivery and spreading of the dsRNA formulation; and (c) Method 3: the cotton swab was first submerged in the dsRNA formulation, and then rolled over uncoated SiC particles, and finally gently rolled on the leaf surface.

Three liquid formulations of a 78 bp dsRNA trigger against GFP (SEQ ID NO:2) were tested: 2 milligrams/milliliter dsRNA in water; 2 milligrams/milliliter dsRNA in 200 millimolar mannitol and 20 millimolar MES; and 0.0125 milligrams/milliliter dsRNA in a Lipofectamine® formulation. For each treatment, a total of 20 microliters dsRNA formulation was applied per treated leaf of approximately 4-week old transgenic *Nicotiana benthamiana* 16c plants (three plants per treatment). Silencing was assessed visually using blue light excitation at 4 and 7 days after treatment. In this experiment, all three delivery methods and all dsRNA formulations produced GFP silencing foci in treated leaves. Plants treated by Method 1 maintained normal leaf growth and displayed a higher frequency of GFP silencing foci per treated leaf. The frequency of GFP silencing foci was significantly greater in plants treated with a dsRNA concentration of 2 milligrams/milliliter, compared to plants treated with dsRNA of 0.0125 milligrams/milliliter in the Lipofectamine® formulation. Addition of 200 millimolar mannitol and 20 millimolar MES increased frequency of GFP silencing foci across delivery treatment types.

Example 15

This example illustrates non-limiting embodiments of methods, apparatuses, and compositions useful for delivering a nucleic acid into a plant or cells or tissues of a plant. More specifically, this example describes systemic silencing of a target gene by various methods including contacting a plant surface with a matrix supporting an abrasive. In these examples, sandpaper serves as a matrix supporting a particulate abrasive, and is used to abrade a plant surface and deliver a dsRNA trigger to the plant.

Sandpapers for wet sanding were used to deliver a 78 bp dsRNA trigger against GFP (SEQ ID NO:2) into approximately 3-week old transgenic *Nicotiana benthamiana* 16c plants. Three different grit sizes were used: P180, P600, and P2500, which have an average particle size diameter of 82, 25.8, and 8.4 micrometers, respectively. The sandpaper was supported by a ¾-inch diameter PVC tube to facilitate gentle rolling on the surface of the treated leaves. Formulations of the dsRNA at a final concentration of 2 milligrams/milliliter were prepared in water or in aqueous 0.05% Silwet L77. Ten or 20 microliters of dsRNA formulation were pipetted onto the surface of two leaves per plant, and spread with a pipette tip to ensure uniform coverage, followed by abrasion by gently rolling the sandpaper over the treated leaf surface. For comparison, additional plants were treated only with the dsRNA formulation (no abrasion), or with the dsRNA formulation followed by abrasion with a cotton swab supporting SiC particles (360 mesh). Silencing was assessed visually using blue light excitation at 4 and 7 days after treatment.

The results are summarized as follows. No signs of leaf damage or turgor loss was observed in treated *Nicotiana benthamiana* leaves. Treated plants showed no signs of wilting or severe leaf damage immediately after treatment or 1 day after treatment. The observed frequency of GFP silencing foci depended on sandpaper grit size; plants abraded with the 600 sandpaper roller had greater frequency of GFP silencing foci than plants abraded with other sandpaper grit sizes with the cotton swab supporting uncoated SiC particles. In a two-step sequential application (dsRNA applied first, followed by abrasion), abrasion with sandpaper was found to be more efficient in inducing GFP silencing foci than abrasion with a cotton swab supporting uncoated SiC particles, independently of the dsRNA formulation or timing of abrasive treatment.

Results from these and similar experiments provided further inferences. Silencing activity was observed to be retained in plants where the dsRNA-treated leaf was left for a day prior to abrasion; a stronger phenotype and more frequent GFP silencing foci were observed when the dsRNA formulation was left to dry on the surface of the leaf for at least 20 minutes prior to abrasion. Experiments with a "flat" roller, which gave reduced silencing efficacy, suggested that leaf surface abrasion and not pressure alone is the mechanism for dsRNA delivery. Sequential abrasive methods have shown consistently high efficacy levels and success rate. Systemic GFP silencing was observed in sandpaper-abraded *N. benthamiana* 16C plants grown under different conditions and in different locations, approximately 10-13 days after treatment, independent of the dsRNA trigger size used. Efficacy of mechanical abrasion methods was also demonstrated against endogenous gene targets including magnesium chelatase, PAT1, and PDS.

Similar experiments demonstrating localized target gene silencing induced by particle-assisted nucleic acid delivery were carried out in *Arabidopsis thaliana*. The sandpaper abrasion method was modified for developing *Arabidopsis thaliana* leaves from small plants grown in 24-well blocks. Round-tip tweezers were modified by wrapping one end with a paper pad and laboratory film (Parafilm M® Bemis NA, Neenah, Wis.) (to support the leaf and prevent leaf damage), and attaching sandpaper to the other end with double-sided sticky tape. Similarly, methods using a cotton-swab rolling technique for abrasion can also be used on *Arabidopsis thaliana* seedlings.

Similar experiments were also carried out in a transgenic tomato line expressing GFP. GFP and magnesium chelatase silencing foci were observed in tomato seedlings treated with a two-step sequential method including dsRNA application followed by sandpaper abrasion. The frequency of putative GFP silencing foci was low (1-2 foci per treated leaves) but was present in 6 to 7 of 10 treated tomato seedlings. Magnesium chelatase silencing foci was observed with low frequency in treated tomato seedlings, tomato seedlings treated with mixed dsRNA triggers displayed the expected co-localized GFP and magnesium chelatase silencing foci.

Example 16

This example illustrates non-limiting embodiments of methods, apparatuses, and compositions useful for delivering a nucleic acid into a plant or cells or tissues of a plant. More specifically, this example describes systemic silencing of a target gene by applying a relatively small (22 base-pair) dsRNA trigger to a plant surface, followed by abrasion with a matrix supporting particulate abrasives.

This example describes systemic silencing of GFP in transgenic *Nicotiana benthamiana* 16c plants by a 22 bp dsRNA trigger (SEQ ID NO:14) in combination with sandpaper abrasion. Non-specific dsRNA was used as a control in the experiment. The dsRNA was dissolved in water to 1 milligram/milliliter final concentration and a total of 20 microliters dsRNA was applied to 2 young leaves on individual transgenic *Nicotiana benthamiana* 16c plants. The treated leaves were abraded with a 600 sandpaper roller. Samples for Northern blot analysis of GFP mRNA levels were collected at 24 and 48 hours after treatment. Silencing was assessed visually using blue light excitation at 2, 5, 8, and 13 days after treatment. A reduction of GFP mRNA expression in T52623 dsRNA-treated plants was observed at 1 day after treatment, and strong GFP expression reduction observed at 2 days after treatment. Localized GFP silencing was observed on treated leaves at 2 days after treatment, and the localized silencing phenotype became much clearer and stronger from 5 days after treatment onward. Systemic GFP silencing was observed on untreated young leaves at 10 to 13 days after treatment.

In a similar experiment, 22 bp dsRNA trigger (SEQ ID NO:17) targeting an endogenous gene, magnesium chelatase. The dsRNA was dissolved in water to 1 milligram/milliliter final concentration and a total of 20 microliters dsRNA was applied to 2 young leaves on individual transgenic *Nicotiana benthamiana* 16c plants. The treated leaves were abraded with a 600 sandpaper roller. Silencing was assessed visually under visible light at 2, 5, 8, and 13 days after treatment. Localized silencing was observed as the expected chlorophyll-deficient phenotype in leaves treated with SEQ ID NO:17.

Example 17

This example illustrates non-limiting embodiments of methods, apparatuses, and compositions useful for delivering a nucleic acid into a plant or cells or tissues of a plant. More specifically, this example describes systemic silencing of a target gene by treatment with a dsRNA targeting the promoter region of the target gene, followed by abrasion with a matrix supporting particulate abrasives.

The region upstream of the transgenic GFP insert from *Nicotiana benthamiana* 16c was cloned and sequenced. The size of the sequenced region is 2278 bp and contains an 835 bp region encoding the cauliflower mosaic virus (CaMV) 35S promoter. An upstream expression cassette containing a nos terminator is located 698 bp from the 5' end of the CaMV 35S promoter. Three dsRNA triggers, ranging in size from 122-127 bp, were designed to match the DNA sequence from 3' end of the CaMV 35S promoter region: CaMV.35S-1 (SEQ ID NO:18), CaMV.35S-2 (SEQ ID NO:19), CaMV.35S-3 (SEQ ID NO:20), and (as a control) a 124 bp dsRNA targeting the coding region of GFP (T41817, SEQ ID NO:3). The dsRNA was dissolved in water to 4 milligram/milliliter final concentration and a total of 10-20 microliters dsRNA was applied to leaves 3 and 4 from 2 week-old plants transgenic *Nicotiana benthamiana* 16c plants. After the RNA was aliquoted on the leaves, a pipette tip was used to evenly spread the RNA over the surface of the adaxial side of each leaf. The RNA solution was allowed to dry for 30 minutes and then the top of the leaf was abraded once with P600 sandpaper glued to a dowel that was rolled over the leaf. The plants were then placed in a growth chamber set for 263 micromoles of light set for 14 hour/10 hour (light/dark cycle) with a temperature setting of 23 degrees Celsius/18 degrees Celsius (day/night). Silencing was assessed visually using blue light excitation at 7 days after treatment. The first 2 triggers closest to the end of the promoter, CaMV.35S-1 (SEQ ID NO:18) and CaMV.35S-2 (SEQ ID NO:19), produced a strong silencing phenotype with many small silencing foci on the treated leaves. CaMV.35S-3 (SEQ ID NO:20) produced the weakest phenotype with only slight levels of silencing in only a few areas. The control dsRNA targeting the coding region of GFP (SEQ ID NO:3) gave the strongest phenotype with many large silencing spots that merge to cover most of the treated leaves.

Example 18

This example illustrates non-limiting embodiments of methods, apparatuses, and compositions useful for delivering a nucleic acid into a plant or cells or tissues of a plant. More specifically, this example describes systemic silencing of a target gene by treatment with a nucleic acid, followed by abrasion with a particulate that disrupts cells in the cuticle or epidermis or both cuticle and epidermis of the plant.

Double-stranded RNA was fluorescently labelled with Cy3 and coated onto SiC particles (320 mesh) or soda lime glass beads of three size ranges (10-22, 22-27, and 35-45 micrometer). Control particles were made in the same way but without Cy3 labelling. The dry dsRNA-coated SiC or glass beads were sprayed onto leaves and central axis of 3-week old *Nicotiana benthamiana* 16c plants at 65 psi using a G78 airbrush mounted to a ring stand at 5-7 centimeters nozzle-to-leaf distance from the plants. Equipment was cleaned with ethanol between treatments to minimize cross-contamination.

For live imaging studies regions of interest (silenced spots identified as red areas under UV light) were removed with 4-5 millimeter biopsy punches and the live tissues were imaged with confocal fluorescence microscopy. In addition, tissue samples were fixed with paraformaldehyde, cryoprotected with sucrose, mounted in OCT medium, and cryosectioned for epifluorescent and bright-field imaging. These microscopic studies demonstrated that the sprayed particles primarily impacted epidermal cells.

Similar microscopic studies were performed on tomato leaves treated with a two-step sequential method including dsRNA application followed by abrasion with sandpapers of different grit sizes. The results demonstrated that silencing efficiency increased in the grit size order P200<P400<P2000 (i. e., from coarser to finer grits), indicating that the most efficacious sandpapers have grit sizes that can disrupt the leaf cuticle and only compromise or partially compromise the epidermal cell layer but do not cause deeper damage.

Example 19

This example illustrates non-limiting embodiments of methods, apparatuses, and compositions useful for delivering a nucleic acid into a plant or cells or tissues of a plant. More specifically, this example describes systemic silencing of a target gene by treatment with a dsRNA, followed by abrasion with a matrix supporting particulate abrasives.

This experiment compared the silencing efficiency of sandpapers of different grit sizes in a two-step sequential application. The effects of nuclease inhibitors were also examined.

Three dsRNA formulations were prepared. The base formulation contained 124 bp dsRNA trigger (SEQ ID NO:3) at 2 milligram/milliliter, 200 millimolar mannose, 4 millimolar MES buffer final concentration in water. A second formulation was identical to the base formulation but included 4.8 millimolar $Zn_2SO_4$ as an RNase inhibitor. A third formulation was identical to the base formulation but included 3.7% RNasin® Ribonuclease Inhibitor (Promega Corporation, Madison, Wis.) as an RNase inhibitor. A total of 10 or 20 microliters dsRNA was applied to two leaves of 3-week old plants transgenic *Nicotiana benthamiana* 16c plants. After the RNA was aliquoted on the leaves, a pipette tip was used to evenly spread the RNA over the surface of the adaxial side of each leaf. The RNA solution was allowed to dry for 30 minutes and then the top of the leaf was abraded once with sandpaper of two different grit sizes (P180 or P600) attached to a ¾-inch PVC tube that was rolled over the leaf. Silencing was assessed visually using blue light excitation at 7 days after treatment. Results are provided in Table 7.

TABLE 7

| Sandpaper grit | RNase inhibitor | Average number of GFP silencing loci per leaf | Standard error |
|---|---|---|---|
| P600 | None | 50 | 15 |
| P600 | $Zn_2SO_4$ | 78 | 13 |
| P600 | RNasin ® | 66 | 12 |
| P180 | None | 4 | 2 |
| P180 | $Zn_2SO_4$ | 9 | 3 |
| P180 | RNasin ® | 6 | 2 |

These results show that across all formulations, P600 abraded leaves had ~10× more GFP silencing foci per leaf than those abraded with a coarser P180 sandpaper. Independently of the sandpaper grit used, formulations including an RNase inhibitor had more GFP silencing foci per leaf. The effect of nuclease inhibitor on increasing number of GFP silencing foci per leaf was relatively stronger for the coarser P180 sandpaper abraded leaves than for the P600 abraded leaves. At the concentrations used, $Zn_2SO_4$ had the strongest effect on increasing the number of GFP silencing foci per leaf.

Example 20

This example illustrates non-limiting embodiments of methods, apparatuses, and compositions useful for delivering a nucleic acid into a plant or cells or tissues of a plant. More specifically, this example describes systemic silencing of a target gene by way of particulate-assisted delivery of a nucleic acid such as DNA viral vector into a plant. This example demonstrates the effect of directly applied dsRNA triggers in preventing systemic infection of TSWV.

An experiment was conducted to assess the capacity of dsRNA triggers applied without bacterial lysate to prevent infection with tomato spotted wilt virus (TSWV) in *Nicotiana benthamiana*. GFP silencing served as a tracer for trigger delivery and processing. Two 298 bp chimeric dsRNA triggers were produced; the first trigger TSWV-GFP-TSWV (SEQ ID NO:21) included two dsRNA regions targeting GFP flanking a dsRNA region targeting the TSWV N-gene, and the second trigger GFP-TSWV-GFP (SEQ ID NO:22) included two dsRNA regions targeting the TSWV N-gene flanking a dsRNA region targeting GFP. The blunt-ended 141 bp dsRNA trigger (SEQ ID NO:23) targeting GFP was used as a control.

The chimeric and control dsRNA triggers were applied directly to *N. benthamiana* 16c plants showing 3 true leaves (approximately 26 days after germination), followed by abrasion with 600 grit sandpaper. Local silencing of GFP was observed on the treated leaves in all treatments 4 days after treatment; at this time, TSWV was rub-inoculated onto the leaves showing local GFP silencing. Fourteen days after TSWV challenge, plants were assessed for development of TSWV symptoms. All plants treated with the GFP trigger alone were strongly symptomatic for TSWV. Less than 20% of plants treated with the chimeric GFP/TSWV dsRNA triggers were obviously infected with TSWV. Similar results occurred in a similar experiment where plants were inoculated with TSWV 7 days after treatment, demonstrating that direct application of the chimeric dsRNA triggers protected plants from TSWV infection for at least 7 days after treatment.

Example 21

This example illustrates non-limiting embodiments of methods, apparatuses, and compositions useful for delivering a nucleic acid into a plant or cells or tissues of a plant. More specifically, this example describes systemic silencing of a target gene using a dsRNA trigger targeting a non-coding regulatory region of the gene to be silenced, and heritability of the phenotype in a progeny plant.

The sequence of the promoter region of the chalcone synthase chs (A) gene in *Petunia hybrida* was published by Van der Meer et al. (1990) *Plant Mol. Biol.,* 15:95-190. A 258 bp blunt-ended dsRNA trigger (anti-sense strand having SEQ ID NO:24) targeting the upstream promoter region was produced. The dsRNA trigger is applied to *Petunia hybrida* leaves with abrasion, using any of the single-step or two-step methods described in the preceding working Examples. The treated leaves are regenerated into RO plants. RO plants displaying the expected phenotype of white flowers are selected. The white flower phenotype is heritable by an epigenetic effect in plants of the subsequent generation.

Additional experiments were carried out to test for silencing in plants regenerated directly from treated tissue. *Nicotiana benthamiana*) plants (line 16c) transgenically expressing green fluorescent protein (GFP) driven by the 35S promoter were topically treated using any of the single-step or two-step methods described in the preceding working Examples; a 127 bp blunt-ended dsRNA trigger with the anti-sense (i. e., anti-sense relative to the direction of the GFP gene's coding sequence) strand having SEQ ID NO:29 targeting the 35S promoter was applied with abrasion to either the second or the third true leaves on 3-week-old plants. Both local silencing and systemic silencing of the target gene GFP were observed in the treated 16c plants. Samples of leaf tissue displaying local silencing were taken from the topically treated leaves and cultured on solid media (using a protocol similar to that described in Horsch et al. (1984) *Science,* 223:496-498). Sixteen RO 16c plants were regenerated; fifteen of the sixteen RO plants exhibited a homogenous phenotype with complete silencing of the target gene GFP throughout the entire RO life cycle.

In additional experiments, *Nicotiana benthamiana*) plants (line 16c) transgenically expressing green fluorescent protein (GFP) driven by the 35S promoter are topically treated using any of the single-step or two-step methods described in the preceding working Examples; a 311 bp blunt-ended dsRNA trigger with the anti-sense (i. e., anti-sense relative to the direction of the GFP gene's coding sequence) strand having SEQ ID NO:30 targeting the 35S promoter is applied with abrasion to two leaves of each plant. Both local silencing and systemic silencing of the target gene GFP are observed in the treated 16c plants. Samples of leaf tissue from the topically treated leaves displaying local silencing are taken for culture on solid media and R0 plants regenerated. The R0 plants include 16c plants that exhibited a homogenous phenotype with complete silencing of the target gene GFP. R0 plants displaying the expected phenotype of GFP silencing are selected. The silenced GFP phenotype is heritable by an epigenetic effect in plants of the subsequent generation.

Example 22

This example illustrates non-limiting embodiments of methods, apparatuses, and compositions useful for delivering a nucleic acid into a plant or cells or tissues of a plant. More specifically, this example describes use of a method including application of nucleic acids to the surface of a plant, followed by abrasion with a particulate, whereby the nucleic acids are delivered to the plant and result in in vivo editing or sequence replacement of a gene in the plant.

Methods for in vivo editing or sequence replacement of a gene are known in the art, for example through the used of zinc-finger nucleases, CRISPR, and Cas9. See, for example, Townsend et al. (2009) *Nature,* 459:442-446; Qi et al. (2012) *Nature Biotechnol.,* 30:1002-1007; Cong et al. (2013) *Science,* 339:819-823; and Hsu et al. (2013) *Nature Biotechnol.,* 31:827-834. In this example, nucleic acids for in vivo editing are used with methods similar to those described herein in the preceding Examples to modify the sequences of an endogenous gene in a plant.

Specific amino acid point mutations of the endogenous acetolactate synthase genes (ALS SuRA and SuRB) in tobacco (*Nicotiana tabacum*), which share highly conserved coding regions, result in resistance to certain herbicides. Three such amino acid point mutations are P191A (conferring resistance to chlorsulphuron), W568L (conferring resistance to both chlorsulphuron and imazaquin), and S647T (conferring resistance to imazaquin), for which the corresponding nucleotide mutations have been reported (depicted in FIG. 1*b* of Townsend et al. (2009) *Nature,* 459:442-446).

Three nucleic acids are prepared: (1) a CAS9 expression DNA plasmid; (2) a synthetic ssRNA containing a fused target sequence/guide RNA, wherein the target RNA includes about 20 nucleotides of the selected region to be edited in vivo, fused to a guide RNA having the sequence SEQ ID NO:25; and (3) a donor DNA (provided as either a plasmid or as a dsDNA fragment) including a replacement sequence selected from P191A (SEQ ID NO:26), W568L (SEQ ID NO:27), and S647T (SEQ ID NO:28), plus additional 5' and 3' flanking sequence as needed. The three nucleic acids are applied to *Nicotiana tabacum* leaves with abrasion, using any of the single-step or two-step methods described in the preceding working Examples. Herbicide-resistant RO tobacco plants are regenerated from treated leaves on selective media containing the appropriate herbicide.

A separate series of experiments employed a commercially available CRISPR-Cas9 genome editing system ("Alt-R™ CRISPR-Cas9 System", Integrated DNA Technologies (IDT, 1710 Commercial Park, Coralville, Iowa 52241, USA). Nucleic acids were obtained from Integrated DNA Technologies (IDT, 1710 Commercial Park, Coralville, Iowa 52241, USA): (1) a crRNA having the sequence of SEQ ID NO:31, designed to target a region near the 5' end of the GFP mRNA; and (2) a "universal tracrRNA oligonucleotide" with the primary nucleotide sequence of SEQ ID NO:32, modified to improve RNase resistance using an IDT proprietary modification. The two nucleic acids are applied with abrasion, together with a source of Cas9 or a modified Cas9, to leaves of hemizygous *Nicotiana benthamiana* plants (line 16c) transgenically expressing green fluorescent protein (GFP) driven by the 35S promoter, using any of the single-step or two-step methods described in the preceding working Examples. The Cas9 or modified Cas9 is provided in a convenient from, e. g., as a CAS9 expression DNA plasmid or as a commercially available Cas9 nuclease (e. g., purified, codon-optimized, recombinant *S. pyogenes* Cas9 nuclease catalogue number 1074181, Integrated DNA Technologies (IDT, 1710 Commercial Park, Coralville, Iowa 52241, USA). The nucleic acids and Cas9 source are applied with abrasion to either the second or the third true leaves on 3-week-old plants. Both local silencing and systemic silencing of the target gene GFP are observed in the treated 16c plants. Samples of leaf tissue from the topically treated leaves displaying local silencing are taken for culture on solid media and RO plants regenerated. The RO plants include 16c plants that exhibited a homogenous phenotype with complete silencing of the target gene GFP.

All of the materials and methods disclosed and claimed herein can be made and used without undue experimentation as instructed by the above disclosure. Although the methods and compositions as described herein have been described in terms of preferred embodiments and illustrative examples, it will be apparent to those of skill in the art that variations can be applied to the materials and methods described herein without departing from the concept, spirit and scope of this disclosure. All such similar substitutes and modifications apparent to those skilled in the art are deemed to be within the spirit, scope and concept of this disclosure as defined by the appended claims.

What is claimed is:

1. A method for silencing a target gene in a plant, comprising, in any order, the steps of:

(a) abrading a surface of a plant with a particulate of a size greater than about 2.5 micrometers;

(b) applying an RNA to the surface of the plant, wherein the RNA comprises a sequence that is complementary or identical to 21 or more contiguous nucleotides in the sequence of a target gene in the plant;

wherein the particulate, the RNA, or both, are further applied with an osmolyte, and whereby the target gene is silenced.

2. The method of claim 1, wherein (a) the target gene is an endogenous gene of the plant or a transgene expressed in the plant, (b) the target gene in the plant is a gene of a parasitic plant, fungus, or bacterium that is a pathogen or parasite of the plant, (c) the target gene is multiple target genes, or (d) the target gene is multiple target genes from more than one species.

3. The method of claim 1, wherein (a) the RNA is single-stranded RNA, (b) the RNA is double-stranded RNA, (c) the RNA is a miRNA precursor or a small RNA, (d) the RNA is non-transcribable, (e) the RNA is not self-replicating, (f) the RNA comprises 21-500 nucleotides or base pairs, or (g) the RNA is not contained in a viral vector nor encoded by a plasmid.

4. The method of claim 1, wherein (a) the particulate is selected from the group consisting of a mineral abrasive, a metal abrasive, a synthetic abrasive, and an organic abrasive, (b) the particulate is selected from the group consisting of aluminum oxide, silicon carbide, silicon dioxide, soda lime glass, diatomaceous silica (diatomaceous earth), flint, quartz, garnet, silicon dioxide, pumice, sand, feldspar, calcite, steel, tungsten, ceramic, boron carbide, tungsten carbide, (c) the particulate is of an average size range from about 2.5 micrometers to about 50 micrometers, or (d) the particulate is supported by, attached to, or embedded in a matrix.

5. The method of claim 1, wherein the particulate, the RNA, or both, are further applied with (a) at least one selected from the group consisting of water, a biocide, a chelator, a buffer, a nonionic surfactant, a zwitterionic surfactant, a defoamer, a rainfastness agent, and a photoprotectant, (b) at least one selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator, or (c) at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

6. A method for introducing a nucleic acid into a plant, comprising:

(a) in any order, the steps of (i) applying a composition comprising a nucleic acid to a surface of a plant, and (ii) contacting a matrix supporting an abrasive with the surface; or, (b) in any order, the steps of (i) abrading a surface of a plant with a particulate of a size greater than about 2.5 micrometers, and (ii) applying a composition comprising a nucleic acid to the surface of the plant, wherein the nucleic acid comprises a sequence that is complementary or identical to 21 or more contiguous nucleotides in the sequence of a target gene in the plant;

wherein the abrasive or the particulate, or the composition comprising a nucleic acid, or both, are further applied with an osmolyte, and whereby the nucleic acid is introduced into the plant.

7. The method of claim 6, wherein (a) the nucleic acid is DNA, (b) the nucleic acid is DNA in the form of a plasmid or viral vector, (c) the nucleic acid is single-stranded RNA, (d) the nucleic acid is double -stranded RNA, (e) the nucleic acid is a combination of DNA and RNA, (f) the nucleic acid is a miRNA precursor or a small RNA, (g) the nucleic acid is a non-transcribable RNA, (h) the nucleic acid is a non-self-replicating DNA or RNA, (i) the nucleic acid is a DNA that comprises 21-500 nucleotides or base pairs, (j) the nucleic acid is an RNA that comprises 21-500 nucleotides or base pairs, (k) the nucleic acid is an RNA that is not contained in a viral vector nor encoded by a plasmid, (l) the nucleic acid is provided in a microbial cell or as a microbial fermentation product, or (m) the nucleic acid comprises at least 19 consecutive nucleotides having a sequence that is complementary or identical to the sequence of a target gene in the plant.

8. The method of claim 6, wherein (a) the target gene is an endogenous gene of the plant or a transgene expressed in the plant, (b) the target gene in the plant is a gene of a parasitic plant, fungus, or bacterium that is a pathogen or parasite of the plant, (c) the target gene is multiple target genes, or (d) the target gene is multiple target genes from more than one species.

9. The method of claim 6, wherein (a) the abrasive or the particulate is selected from the group consisting of a mineral abrasive, a metal abrasive, a synthetic abrasive, and an organic abrasive, (b) the abrasive or the particulate is selected from the group consisting of aluminum oxide, silicon carbide, silicon dioxide, soda lime glass, diatomaceous silica (diatomaceous earth), flint, quartz, garnet, silicon dioxide, pumice, sand, feldspar, calcite, steel, tungsten, ceramic, boron carbide, tungsten carbide, (c) the abrasive or the particulate is of an average size range from about 2.5 micrometers to about 50 micrometers, or (d) the abrasive or the particulate is supported by, attached to, or embedded in a matrix.

10. The method of claim 6, wherein the abrasive or the particulate, or the composition comprising a nucleic acid, or both, are further applied with (a) at least one selected from the group consisting of water, a biocide, a chelator, a buffer, a nonionic surfactant, a zwitterionic surfactant, a defoamer, a rainfastness agent, and a photoprotectant, (b) at least one selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator, or (c) at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

* * * * *